(12) United States Patent
Chae et al.

(10) Patent No.: US 12,727,791 B2
(45) Date of Patent: Sep. 8, 2026

(54) CONTINUOUS BLOOD GLUCOSE MEASUREMENT APPARATUS

(71) Applicant: I-SENS, INC., Seoul (KR)

(72) Inventors: Kyung Chul Chae, Seoul (KR); Hyun Ho Choi, Seoul (KR); Goang Yel Ryu, Seoul (KR); Ji Hoon Wang, Seoul (KR); Young Jea Kang, Seoul (KR)

(73) Assignee: I-SENS, INC., Seoul (KR)

(*) Notice: Subject to any disclaimer, the term of this patent is extended or adjusted under 35 U.S.C. 154(b) by 0 days.

(21) Appl. No.: 18/396,726

(22) Filed: Dec. 27, 2023

(65) Prior Publication Data

US 2024/0130643 A1 Apr. 25, 2024
US 2024/0225489 A9 Jul. 11, 2024

Related U.S. Application Data

(63) Continuation of application No. 17/261,176, filed as application No. PCT/KR2019/006739 on Jun. 4, 2019.

(30) Foreign Application Priority Data

Jul. 31, 2018 (KR) ........................ 10-2018-0089330
Sep. 27, 2018 (KR) ........................ 10-2018-0114773

(51) Int. Cl.
*A61B 5/145* (2006.01)
*A61B 5/00* (2006.01)

(52) U.S. Cl.
CPC ...... *A61B 5/14532* (2013.01); *A61B 5/14503* (2013.01); *A61B 5/68335* (2017.08)

(58) Field of Classification Search
CPC ............ A61B 5/14532; A61B 5/14503; A61B 5/68335; A61B 5/4839; A61B 5/150206; A61B 5/0024; A61B 5/6846
See application file for complete search history.

(56) References Cited

U.S. PATENT DOCUMENTS

2005/0101912 A1 5/2005 Faust et al.
2010/0198034 A1 8/2010 Thomas et al.
(Continued)

FOREIGN PATENT DOCUMENTS

JP 2009-82631 4/2009
JP 2009-519045 5/2009
(Continued)

OTHER PUBLICATIONS

Intension to Grant dated Aug. 14, 2023 for European Patent Application No. 19 843 611.5.
(Continued)

*Primary Examiner* — Abid A Mustansir
(74) *Attorney, Agent, or Firm* — WOMBLE BOND DICKINSON (US) LLP

(57) ABSTRACT

The present disclosure relates to a continuous glucose monitoring device, in which a body attachment unit is manufactured so as to be assembled in an applicator, thereby minimizing additional work for a user in attaching the body attachment unit to a body, and allowing attachment of the body attachment unit to the body simply by operation of the applicator. In particular, a wireless communication chip is provided in the body attachment unit to enable communication with an external terminal, thereby enabling simple and convenient use without additional work of connecting a separate transmitter, and allowing easier maintenance. In addition, the continuous glucose monitoring device is activated by a user's operation after the body attachment unit is attached to the body, such that an activation start time can be adjusted to a time appropriate to the user's needs, and the continuous glucose monitoring device can be activated in a stabilized state, and thereby can monitor blood glucose more accurately.

9 Claims, 48 Drawing Sheets

(56) References Cited

U.S. PATENT DOCUMENTS

| | | | |
|---|---|---|---|
| 2012/0095488 A1 | 4/2012 | Saeki et al. |
| 2013/0267813 A1 | 10/2013 | Pryor et al. |
| 2013/0267814 A1 | 10/2013 | Schraga |
| 2016/0030078 A1 | 2/2016 | Lee et al. |
| 2016/0157759 A1 | 6/2016 | Yang |
| 2017/0188912 A1 | 7/2017 | Halac et al. |
| 2017/0290546 A1 | 10/2017 | Antonio et al. |
| 2020/0297258 A1 | 9/2020 | Chae et al. |
| 2021/0275066 A1 | 9/2021 | Chae et al. |

FOREIGN PATENT DOCUMENTS

| | | |
|---|---|---|
| JP | 2012-85686 | 5/2012 |
| JP | 2013-524872 | 6/2013 |
| JP | 5624984 | 11/2014 |
| JP | 2016-128031 | 7/2016 |
| JP | 2019-507613 | 3/2019 |
| KR | 10-1071657 | 10/2011 |
| KR | 10-2012-0025912 | 3/2012 |
| KR | 10-2017-0038351 | 4/2017 |
| KR | 10-2017-0045236 | 4/2017 |
| KR | 10-2017-0051134 | 5/2017 |
| KR | 10-1773583 | 9/2017 |
| WO | 2011/119898 | 9/2011 |
| WO | 2017/116915 | 7/2017 |
| WO | 2018/081749 | 5/2018 |
| WO | 2018/222009 | 12/2018 |
| WO | 2018/222011 | 12/2018 |
| WO | 2018/222012 | 12/2018 |

OTHER PUBLICATIONS

Notice of Acceptance dated Sep. 26, 2022 for Australian Patent Application No. 2019314012.

Patent Examination Report 2 dated Feb. 28, 2023 for New Zealand Patent Application No. 772735.

Notice of Acceptance dated Sep. 4, 2023 for New Zealand Patent Application No. 772735.

Office Action dated Oct. 3, 2023 for Japanese Patent Application No. 2022-164548 and its English translation provided by Applicant's foreign counsel.

Office Action dated Mar. 12, 2024 for Japanese Patent Application No. 2022-164548 and its English translation provided by Applicant's foreign counsel.

Notice of Allowance dated Sep. 24, 2024 for Japanese Patent Application No. 2022-164548 and its English translation provided by Applicant's foreign counsel.

Notice of Allowance dated Sep. 3, 2024 for U.S. Appl. No. 17/261,176.

Supplemental Notice of Allowance dated Sep. 19, 2024 for U.S. Appl. No. 17/261,176.

Extended European Search Report dated Apr. 12, 2024 for European Patent Application No. 23215400.5.

International Search Report for PCT/KR2019/006739 mailed on Sep. 3, 2019 and its English translation from WIPO (now published as WO2020/027420).

Written Opinion of the International Searching Authority for PCT/KR2019/006739 mailed on Sep. 3, 2019 and its English translation by Google Translate (now published as WO2020/027420).

Office Action dated Jan. 11, 2022 for Japanese Patent Application No. 2021-503127 and its English translation from Global Dossier.

Office Action dated Apr. 29, 2020 for Korean Patent Application No. 10-2018-0114773 and its English translation from Global Dossier.

Office Action mailed on Oct. 14, 2021 for Australian Patent Application No. 2019314012.

Extended European Search Report dated Aug. 13, 2021 for European Patent Application No. 19843611.5.

International Preliminary Report on Patentability (Chapter I) for PCT/KR2019/006739 issued on Feb. 2, 2021 and its English translation from WIPO.

Examination Report No. 2 dated Jun. 28, 2022 for Australian Patent Application No. 2019314012.

Office Action dated May 17, 2022 for Japanese Patent Application No. 2021-503127 and its English translation from Global Dossier.

Examination Report 1 dated Oct. 7, 2022 for New Zealand Patent Application No. 772735.

Notice of Allowance dated Nov. 25, 2020 for Korean Patent Application No. 10-2018-0114773 and its English translation from Global Dossier.

Notice of Allowance dated Sep. 13, 2022 for Japanese Patent Application No. 2021-503127 and its English translation from Global Dossier.

Office Action dated Jul. 19, 2022 for Japanese Patent Application No. 2021-503127 and its English translation from Global Dossier.

Office Action dated Nov. 21, 2023 for U.S. Appl. No. 17/261,176 (now published as U.S. 2021/0275066).

Office Action dated Nov. 21, 2023 for U.S. Appl. No. 17/261,176.

Final Office Action dated May 23, 2024 for U.S. Appl. No. 17/261,176.

Examination Report No. 1 dated Mar. 27, 2024 for Australian Patent Application No. 2023200010.

Notice of Allowance dated Feb. 18, 2025 for Japanese Patent Application No. 2024-000098 and its English translation provided by Applicant's foreign counsel.

Office Action dated Nov. 12, 2024 for Japanese Patent Application No. 2024-000098 and its English translation from Global Dossier provided by Applicant's foreign counsel.

Notice of Allowance dated Oct. 9, 2024 for U.S. Appl. No. 17/261,176.

Office Action dated Sep. 16, 2025 for Japanese Patent Application No. 2025-045628 and its English translation provided by Applicant's foreign counsel.

Examination Report 3 dated Sep. 29, 2025 for New Zealand Patent Application No. 803295.

Examination Report 2 dated Jul. 3, 2025 for New Zealand Patent Application No. 803295.

Extended European search report dated May 7, 2026 for European Patent Application No. 26153441.6.

CONTINUOUS BLOOD GLUCOSE MEASUREMENT APPARATUS

CROSS-REFERENCE TO RELATED APPLICATIONS

The present application is a continuation of U.S. patent application Ser. No. 17/261,176 filed on Jan. 19, 2021, which is the U.S. National Phase of PCT Application No. PCT/KR2019/006739 filed on Jun. 4, 2019, which claims the priority to Korean Patent Application No. 10-2018-0089330 filed on Jul. 31, 2018, and Korean Patent Application No. 10-2018-0114773 filed on Sep. 27, 2018, the entire contents of which are incorporated herein by reference.

TECHNICAL FIELD

The present disclosure is related to an apparatus for continuously measuring blood glucose. In more detail, the present disclosure is related to a continuous blood glucose measurement apparatus in which, by manufacturing the continuous blood glucose measurement apparatus in a state that the body attachable unit is assembled in an applicator, the body attachable unit can be attached to a human body by simply operating the applicator by minimizing additional work of a user for attaching the body attachable unit to the human body, specially, by including a wireless communication chip in the body attachable unit in order to provide telecommunication with an external terminal, it is possible that the use can be more simple and convenient without additional work for connecting a separate transmitter and the maintenance can also be more easily performed, and by initiating the operation according to the manipulation of the user after the body attachable unit is attached to the human body, the operation start time can be adjusted to a proper time depending on the need of the user, the operation can be started in a stable status and more precise blood glucose measurement can be provided.

BACKGROUND

Diabetes is a chronic medical condition that is common in modern people, and in the Republic of Korea, there are 2 million diabetes patients, about 5% of the total population.

Diabetes occurs when the absolute level of the sugar level in blood is high due to the absolute deficiency or relative insufficiency of insulin, produced by the pancreas, caused by various reasons such as obesity, stress, poor eating habits, and inherited hereditary factors and imbalance regarding glucose in the blood.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people, and as excessive blood glucose passes through the tissues and is discharged into the urine, it results in deficiency of glucose, which is absolutely necessary for all tissues of the body, thereby causing abnormalities in respective body tissues.

Diabetes is characterized by substantial absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown, and further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels at home.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately measure blood glucose levels.

Recently, to overcome such a drawback, continuous glucose monitoring systems (CGMSs) inserted into the human body to measure a blood glucose level every few minutes have been developed, and therefore easily perform the management of diabetics and responses to an emergency situation.

Additionally, the blood-collecting glucose monitoring system performs the glucose measurement by collecting blood by pricking a pain-sensitive fingertip with a needle by the diabetes patients themselves, and therefore, the blood collecting process may cause pain and aversion. To minimize such pain and aversion, research and development regarding the CGMSs, which can continuously measure glucose levels by inserting a needle-shaped sensor into a portion of the human body, such as the belly or an arm, which is less pain sensitive, have been undertaken, and furthermore, research and development of non-invasive glucose monitoring systems for measuring glucose without collecting blood have been actively undertaken.

Over the past 40 years, non-invasive glucose monitoring systems have been studied regarding various methods of measuring glucose without collecting blood, for example, optical methods, electrical methods, exhalation measurement methods, and the like. Cygnus Corporation, Redwoo City, Calif., U.S.A, has developed and launched the Glucowatch® G2 Biographer, a wrist watch type, using reverse iontophoresis, but the sales of this product were stopped in 2007, because of many problems, such as skin stimulation issues and qualification approval issues, malfunction caused by sweating, and low reliability in measurement of hypoglycemia comparing with hyperglycemia. Although a variety of non-invasive glucose monitoring techniques have been introduced and reported to date, there have been no practical uses due to low reliability or accuracy.

A continuous glucose monitoring system includes a sensor module attached to the skin of the human body and measuring a blood glucose level by extracting body fluid, a transmitter transmitting the blood glucose level measured by the sensor module to a terminal, the terminal outputting the received blood glucose level, and any other appropriate component. The sensor module includes a needle-shaped sensor probe for insertion into subcutaneous fat to extract interstitial fluid and any other appropriate component. A separate applicator for attaching the sensor module to the body is used.

Those continuous glucose monitoring systems are manufactured to have a wide variety of types depending on their manufacturers, and are used in a variety of methods. However, the most of the continuous glucose monitoring systems are manufactured and distributed as a type that a one-time use sensor module is attached to the human body using an applicator, the user should perform multistage operations/manipulation to operate the applicator to attach the one-time use sensor module to the human body, and after the sensor module is attached to the human body, the user should perform various follow-up operations, such as a procedure of withdrawing a needle by the user.

For example, many operations of unpacking the one-time use sensor module, accurately inserting the one-time use sensor module into the applicator, operating the applicator and inserting the sensor module into the skin in a state that the sensor module is inserted to the applicator, after the insertion, withdrawing the needle of the sensor module from the skin using a separate device, and so on should be performed, and in order to transmit the measurement results regarding glucose to a user terminal, the operation of connecting a separate transmitter to the sensor module and any other appropriate operation should be performed.

Accordingly, the operations of measuring glucose using the continuous glucose monitoring systems may be significantly difficult and inconvenient, which are problematic. Additionally, because the operations of the sensor module and the transmitter is not initiated by the user, there may be problems, for example, low accuracy of the blood glucose measurement result and short device lifespan.

SUMMARY

Technical Problem

The present disclosure is invented to solve problems in conventional technique, and the purpose of the present disclosure is for providing a continuous blood glucose measurement apparatus in which, by manufacturing the continuous blood glucose measurement apparatus in a state that the body attachable unit is assembled in an applicator, the body attachable unit can be attached to a human body by simply operating the applicator by minimizing additional operation of a user for attaching the body attachable unit to the human body, specially, by including a wireless communication chip in the body attachable unit in order to provide telecommunication with an external terminal, it is possible that the use can be more simple and convenient without additional operation for connecting a separate transmitter and the maintenance can also be more easily performed.

Another purpose of the present disclosure is for providing a continuous blood glucose measurement apparatus in which, by initiating the operation according to the manipulation of the user after the body attachable unit is attached to the human body, the operation start time can be adjusted to a proper time depending on the need of the user, and the operation can be started in a stable status and more precise blood glucose measurement can be provided.

Solution to Problem

According to an embodiment of the present disclosure, a continuous glucose measurement apparatus may comprise a body attachable unit configured to be insertedly attachable to a body to extract body fluid and periodically measure blood glucose; and an applicator in which the body attachable unit is coupled, the applicator configured to outwardly discharge the body attachable unit according to manipulation of a user so that the body attachable unit is insertedly attached to the body, wherein the body attachable unit is inserted to an inside of the applicator so that the body attachable unit and the applicator are assembled as one product unit, and wherein the body attachable unit comprises a sensor unit, wherein one end portion of the sensor unit is insertable into the body, and a wireless communication chip configured to wireless communicate with an external terminal.

In this embodiment, the body attachable unit may be configured to initiate operation of the sensor unit and the wireless communication chip by a switch configured to be manipulated by the user.

Additionally, the applicator may comprise a main case, wherein a pressure button is installed at one side of the main case; a plunger body configured to be fixed at a first location inside the main case, and be released from fixation at the first location and linearly move to a second location in an outward discharge direction according to manipulation of the pressure button; and a plunger elastic spring configured to apply an elastic force to the plunger body so that the plunger body linearly moves from the first location to the second location, wherein the body attachable unit is coupled with one end of the plunger body and the body attachable unit is configured to be movable together with the plunger body from the first location to the second location.

Further, a shooting plate configured to be movable according to the manipulation of the pressure button may be coupled in the main case, and the plunger body may be configured to be fixed at the first location by being interlocked with the shooting plate, and be released from interlock with the shooting plate according to movement of the shooting plate.

Additionally, the main case may comprise an outer case, wherein the pressure button is installed to one side of the outer case, and an inner case coupled to an inside of the outer case, the inner case configured to guide a linear movement path of the plunger body, and the shooting plate may be configured to move by being supported by the inner case.

Further, the outer case may comprise a hanging raised part positioned at a portion of the outer case where the pressure button is disposed, and the pressure button may be slidably mounted along an outer surface of the outer case so that a mode is changeable between a safe mode, in which the pressure button is interlocked with the hanging raised part to prevent pressurizing movement caused by pressurizing manipulation of the user, and a pressure standby mode, in which interlock with the hanging raised part is released to be capable of performing the pressurizing movement caused by the pressurizing manipulation of the user.

Additionally, the body attachable unit may comprise a housing configured to be outwardly discharged by the applicator so that a bottom surface of the housing is attachable to the body, wherein the sensor unit is included in the housing in a structure that the one end portion of the sensor unit outwardly protrudes from the housing, and the wireless communication chip is included in the housing; and a needle unit configured to be separably coupled to the housing, covering the one end portion of the sensor unit so that the needle unit is movable together with the sensor unit and the one end portion of the sensor unit is inserted into the body according to outwardly discharging movement of the housing, and the applicator may comprise a needle extracting unit configured to extract and remove the needle unit from the body by moving the needle unit toward the first location when movement of the plunger body from the first location to the second location is completed.

Further, a protection cap may be separably coupled to the applicator to block exposure of the body attachable unit from an outside of the applicator in a state that the body attachable unit is inserted into the inside of the applicator, an adhesive tape and a release paper may be attached to a surface of the body attachable unit which is to be contacted with the body so that the body attachable unit is attachable to the body, and the release paper may be configured to be separated and removed from the adhesive tape together with the protection cap when the protection cap is separated from the applicator.

Additionally, the main case may comprise a return prevention unit configured to block returning movement of the plunger body returning toward the first location after the plunger body is moved to the second location.

Further, the return prevention unit may comprise an interlocking body formed at one side of the plunger body; and a return prevention hook formed at the inner case to prevent the returning movement of the plunger body by being interlocked with the interlocking body when movement of the plunger body from the first location to the second location is completed, wherein an elastic restoration force causes the return prevention hook to be interlocked with the interlocking body.

Additionally, the plunger body may be configured so that an end of the plunger body further protrudes than an end of the main case in a state that the plunger body is moved from the first location to the second location according to the manipulation of the pressure button.

Further, the body attachable unit may be configured so that an end of the body attachable unit further protrudes than the end of the main case in a state that the body attachable unit is moved to the second location together with the plunger body.

Advantageous Effects of Invention

According to an embodiment of the present disclosure, by manufacturing the continuous blood glucose measurement apparatus in a state that the body attachable unit is assembled in an applicator, the body attachable unit can be attached to a human body by simply operating the applicator by minimizing additional operation of a user for attaching the body attachable unit to the human body, specially, by including a wireless communication chip in the body attachable unit in order to provide telecommunication with an external terminal, it is possible that the use can be more simple and convenient without additional operation for connecting a separate transmitter and the maintenance can also be more easily performed.

Additionally, by initiating the operation according to the manipulation of the user after the body attachable unit is attached to the human body, the operation start time can be adjusted to a proper time depending on the need of the user, and the operation can be started in a stable status and more precise blood glucose measurement can be provided.

BRIEF DESCRIPTION OF THE DRAWINGS

FIG. 3 is an exploded perspective view of the continuous blood glucose measurement apparatus according to an embodiment of the present disclosure.

DETAILED DESCRIPTION OF EMBODIMENTS

Figure 1:
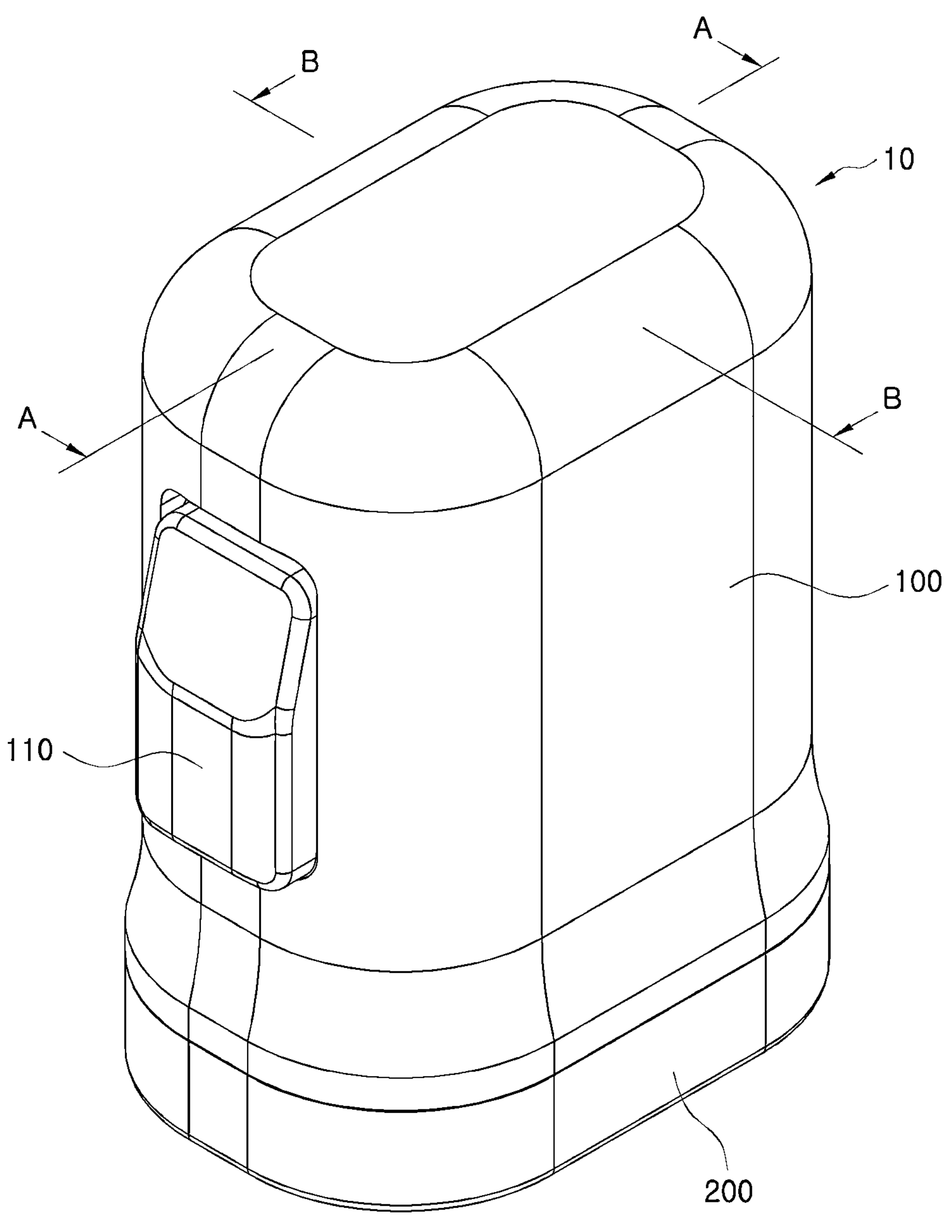
FIG. 1 is a perspective view of schematically illustrating an outer structure of a continuous blood glucose measurement apparatus according to an embodiment of the present disclosure.

Hereinafter, embodiments of the present disclosure will be described in detail with reference to the accompanying drawings. Throughout this document, reference should be made to the drawings, in which the same reference numerals and symbols will be used to designate the same or like components. Additionally, in the following description of the present disclosure, detailed descriptions of known functions and components incorporated herein will be omitted in the case that the subject matter of the present disclosure may be rendered unclear thereby.

Figure 2:
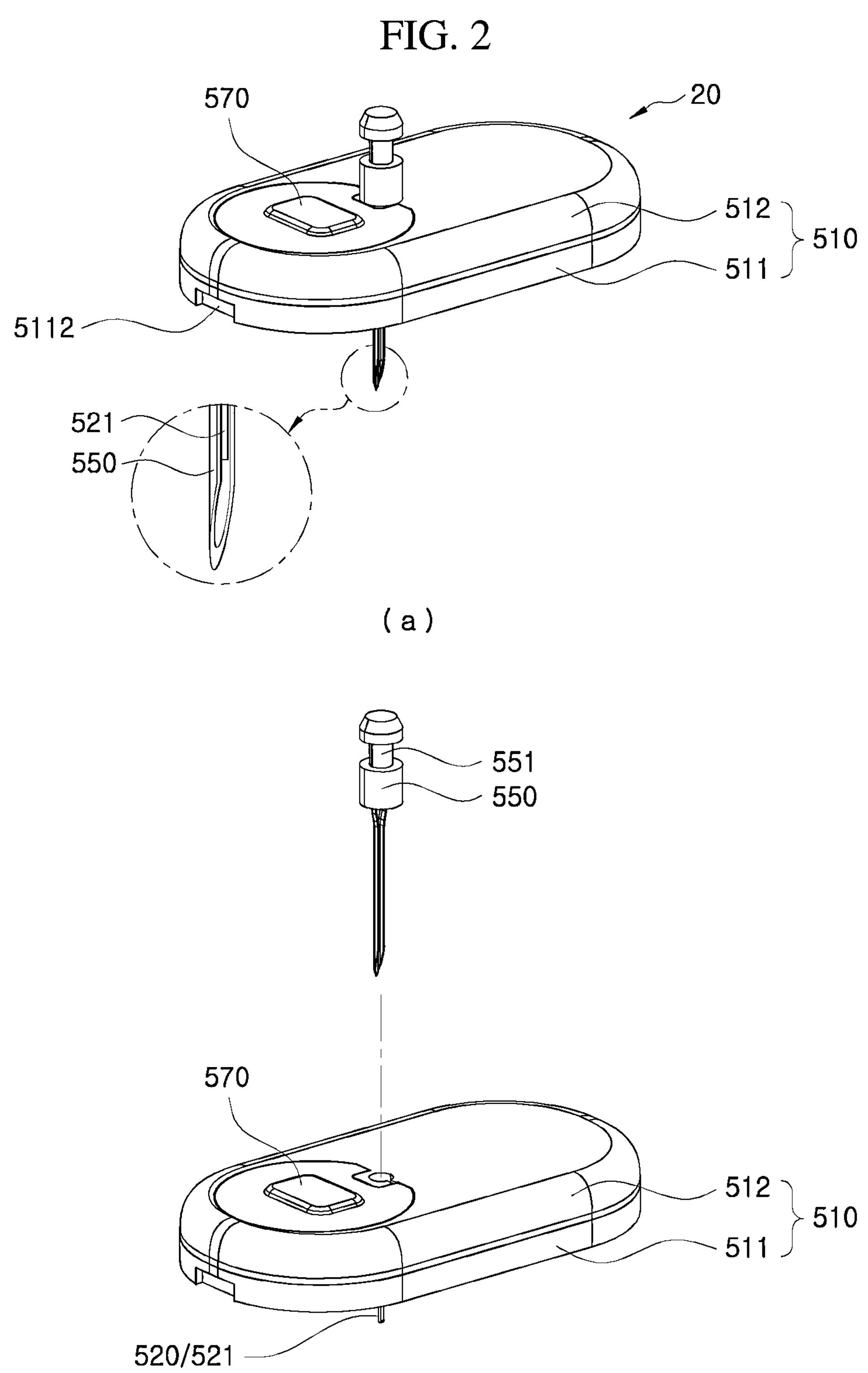
FIG. 2 is a perspective view of schematically illustrating an outer structure of a body attachable unit according to an embodiment of the present disclosure.
Figure 3:
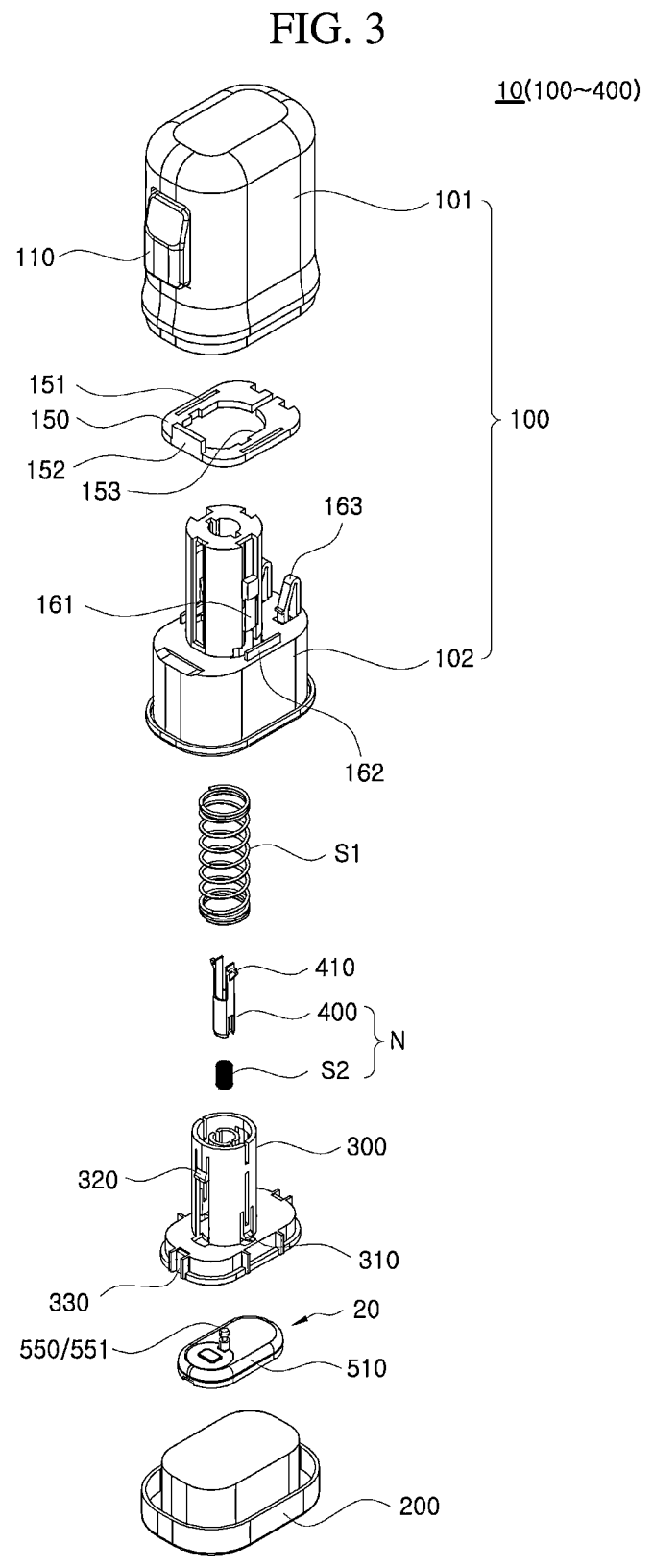
Figure 4:
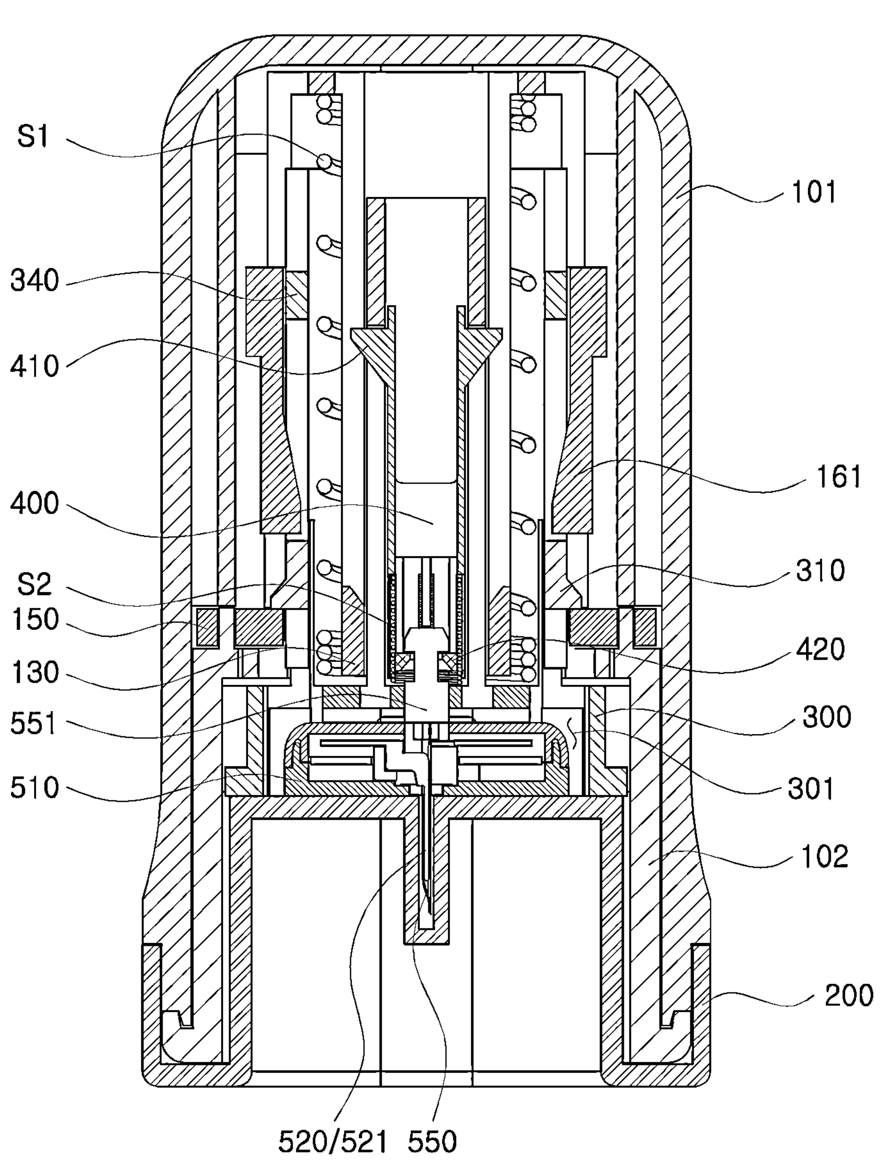
FIG. 4 is a cross-section view taken along line "B-B" of FIG. 1.
Figure 5:
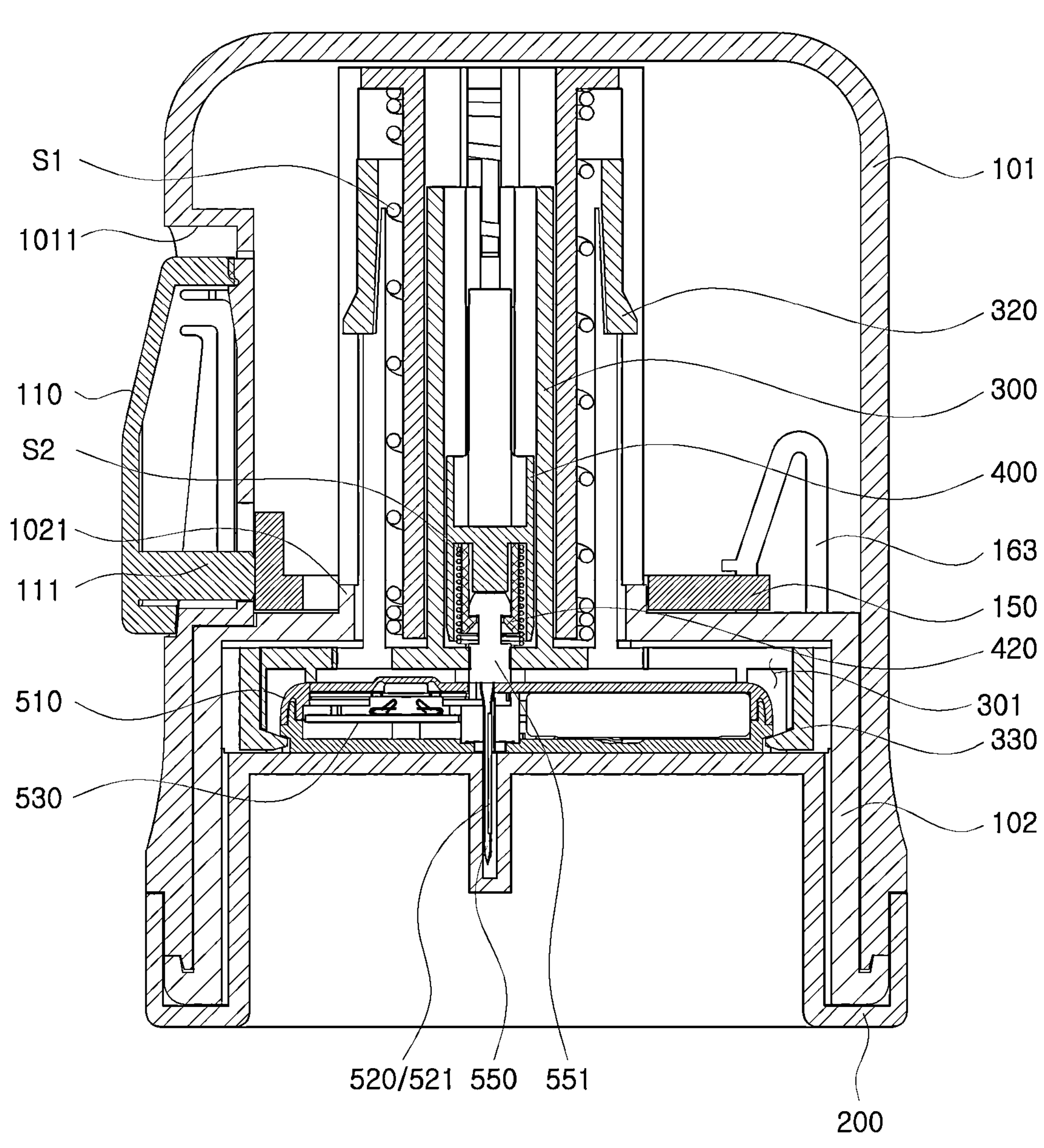
FIG. 5 is a cross-section view taken along line "A-A" of FIG. 1.

FIG. 1 is a perspective view schematically illustrating an outer structure of a continuous blood glucose measurement apparatus according to an embodiment of the present disclosure, and FIG. 2 is a perspective view schematically illustrating an outer structure of a body attachable unit according to an embodiment of the present disclosure, FIG. 3 is an exploded perspective view of the continuous blood glucose measurement apparatus according to an embodiment of the present disclosure, FIG. 4 is a cross-section view taken along line "B-B" of FIG. 1, and FIG. 5 is a cross-section view taken along line "A-A" of FIG. 1.

According to an embodiment of the present disclosure, a continuous blood glucose measurement apparatus may be manufactured as one single unit product that a body attachable unit (20) is assembled inside an applicator (10), and has a simpler structure which can be easily used by minimizing additional work of a user when using the continuous blood glucose measurement apparatus.

The body attachable unit (20) may be configured to be attachable to a human body to periodically measure blood sugar level or glucose by extracting body fluid, and transmit the blood glucose measurement result to an external device such as an external terminal (not shown) and so on. A sensor unit (520) of which one end portion can be inserted into the human body and a wireless communication chip (540) (see FIG. 27) configured to wirelessly communicate with the external terminal can be disposed inside the body attachable unit (20), and therefore, the body attachable unit (20) can be used without additional connection of a separate transmitter.

The applicator (10) is formed such that the body attachable unit (20) is fixedly coupled to inside of the applicator (10), and the applicator (10) is configured to outwardly discharge the body attachable unit (20) according to the manipulation of the user.

In this embodiment, the body attachable unit (20) is assembled and produced in a state that the body attachable unit (20) is inserted into the inside of the applicator (10), and is configured to move in an outward discharge direction pursuant to the operation of the applicator (10) by the manipulation of the user and be attached to the human body.

Therefore, the sensor applicator assembly (1) according to an embodiment of the present disclosure is assembled and manufactured in a state that the body attachable unit (20) is inserted in the inside of the applicator (10) at the manufacturing stage and the body attachable unit (20) can be attached to a skin by only the operation of the applicator (10), and because the sensor applicator assembly (1) is suppled to the user in this state, the user can easily attach the body attachable unit (20) to the skin by only the manipulation simply activating the applicator (10) without extra additional operation for attaching the body attachable unit (20) to the skin. Specifically, since the body attachable unit (20) has the wireless communication chip (540), no connection with an extra transmitter is needed and therefore it can be used more conveniently.

In a conventional continuous blood glucose measurement apparatus, after removing a body attachable unit, which is separately packaged, precisely inserting it into an applicator, and then operating the applicator, the body attachable unit is attached to a skin, but the work precisely inserting the body attachable unit into the applicator is cumbersome as well as difficult and there is a problem in lowering the accuracy of blood glucose measurement because of contaminating the body attachable unit when young children or elderly adults perform this procedure.

In an embodiment of the present disclosure, at the manufacturing stage, it is manufactured and distributed in a state that the body attachable unit (20) is inserted in the applicator (10), and therefore the step that the user removes the body attachable unit (20) from the package and inserts it into the applicator (10) may be omitted, because the body attachable unit (20) can be attached to the skin by simply manipulating the applicator (10), the usability may be significantly improved, and specifically, the accuracy of blood glucose measurement may be improved by preventing the contamination of the body attachable unit (20).

Since it is manufactured in a state that the body attachable unit (20) is inserted in the applicator (10), the body attachable unit (20) and the applicator (10) can be preferably used one time only, not reusable. For this impossibility of the reusable structure, according to an embodiment of the present disclosure, the body attachable unit (2) is configured not to be re-insertable after the body attachable unit (20) inserted in the inside of the applicator (10) is externally discharged.

Therefore, the applicator (10) is formed to be open at one side and the body attachable unit (20) is outwardly discharged through the open side of the applicator (10) to the outside of the applicator (10), and if the body attachable unit (20) is externally discharged by a first one time operation of the applicator (10), it is configured that the body attachable unit (20) cannot be inserted by the user so that another body attachable unit (20) cannot be inserted into the applicator (10) and used after that.

Meanwhile, a separate and additional protection cap (200) can be separably coupled to the applicator (10) in order to block external exposure in a state that the applicator (10) is inserted in the inside of the applicator (10), and it may be configured that the user can attach the body attachable unit (20) to the human body by operating the applicator (10) only after the protection cap (200) is separated.

In the embodiment of the present disclosure, an adhesive tape (560) is provided at a side of the body attachable unit (20) contacting the human body to be attached to the body, to protect the adhesive tape (560) a release paper (561) is attached to a surface of the adhesive tape (560) contacting the human body, and the release paper (561) of the adhesive tape (560) may be configured to be separated and removed from the adhesive tape (560) during the operation of separating the protection cap (200) from the applicator (10).

For example, the release paper (561) may be configured to adhere one side of the release paper (561) to the protection cap (200), and therefore, if the user separates the protection cap (200) from the applicator (10), the release paper (560) may be separated and removed from the adhesive tape (560) together with the protection cap (200). Accordingly, if the user separates the protection cap (200), the release paper (561) of the adhesive tape (560) is separated and removed, and therefore in this status the body attachable unit (20) can be attached to the human body by the operation of the applicator (10).

Additionally, in a state that the body attachable unit (20) is inserted in the inside, the applicator (10) fixes the body the attachable unit (20), and in a state that the body attachable unit (20) is outwardly discharged and moved, the applicator (10) is configured to release the fixed state of the body attachable unit (20). Accordingly, in a state that the body attachable unit (20) is assembled to be inserted in the inside of the applicator (10), the body attachable unit (20) maintains the fixed state, and when the body attachable unit (20) is externally discharged and attached to the skin by actuating the applicator (10), the state fixed between the applicator (10) and the body attachable unit (20) is released, and therefore if the applicator (10) is separated in this state the applicator (10) is separated from the body attachable unit (20) and only the body attachable unit (20) remains on the skin.

Meanwhile, the body attachable unit (20) according to an embodiment of the present disclosure is configured to cause the sensor unit (520) and the wireless communication chip (540) to initiate their operations through a separate switching means controlled by the user. Accordingly, after inserting and attaching the body attachable unit (20) to the human body by using the applicator (10), the user may initiate to operate the body attachable unit (20) through the switching means or other appropriate means included in the body attachable unit (20), and from the time of the initiation of the operation the sensor unit (520) and the wireless communication chip (540) may be operated, the blood glucose of the human body may be measured, and the measurement result may be transmitted to the external terminal. In this embodiment, the switching means operated by the user may be implemented in various ways, and the detailed description of such a switching means and the body attachable unit (20) will be described later with reference to FIGS. 26 to 37.

Additionally, in the body attachable unit (20), the sensor unit (520) is disposed in a housing (510) which is formed to be capable of separating into an upper housing (512) and a lower housing (511), and one end portion of the sensor unit (520) outwardly protrudes from the housing (510) so that it can be inserted and attached to the human body. The sensor unit (520) may comprise a sensor probe unit (521) to be inserted into the human body, and a sensor body unit (522) disposed inside the housing (510), and the sensor probe (521) and the sensor body unit (522) are formed as one end portion and another end portion of the sensor unit (520), respectively, and in a bent shape.

In this embodiment, to smoothly perform the body insertion process of the sensor unit (520), a separate needle unit (550) may be separatably coupled to the housing (510). The needle unit (550) may surround one end portion of the sensor unit (520) and be configured to be inserted together with the sensor unit (520) so that one end portion of the sensor unit (520) can be stably inserted into the human body.

As shown in FIG. 2, the needle unit (550) may be separatably coupled to the housing (510) in a direction penetrating the top and bottom of the housing (510) of the body attachable unit (20), the needle unit (550) may be formed to have a structure covering the outside of the sensor unit (520), and a need head (551) is formed at the upper end portion of the needle unit (550). If the body attachable unit (20) is moved in the direction outwardly discharged by the applicator (10), the needle unit (550) is inserted into the human body first before the sensor unit (520) is inserted into the human body and the needle unit (550) may support the sensor unit (520) such that the sensor unit (520) can be stably inserted in the skin. The needle unit (550) may be coupled with a needle extracting body (400) of the applicator (10) through the needle head (551), and after the body attachable unit (20) is inserted and attached to the human body by the operation of the applicator (10), the needle unit (550) may be configured to be withdrew and removed from the human body by the needle extracting body (400) of the applicator (10).

Next, the details of components of the applicator (10) according to an embodiment of the present disclosure will be followed.

The applicator (10) according to an embodiment of the present disclosure may comprise a main case (100), wherein a pressure button (110) configured to perform pressure operation by the user is installed at one side of the main case (100), a plunger body (300) coupled to a first location of the inside of the main case (100) and configured to be decoupled from the first location by the operation of the pressure button (110) and linearly move from the first location to a second location in an outward discharge direction, and a plunger elastic spring (S1) configured to apply an elastic force to the plunger body (300) so that the plunger body (300) can linearly move from the first location and the second location, and the body attachable unit (20) is coupled with one side of the plunger body (300) and the body attachable unit (20) is configured to be moved together with the plunger body (300) from the first location to the second location.

As discussed above, the protection cap (200) as a separate element may be separatably coupled to the lower end portion of the main case (100) to protect the inside of the body attachable unit (20).

Figure 6:
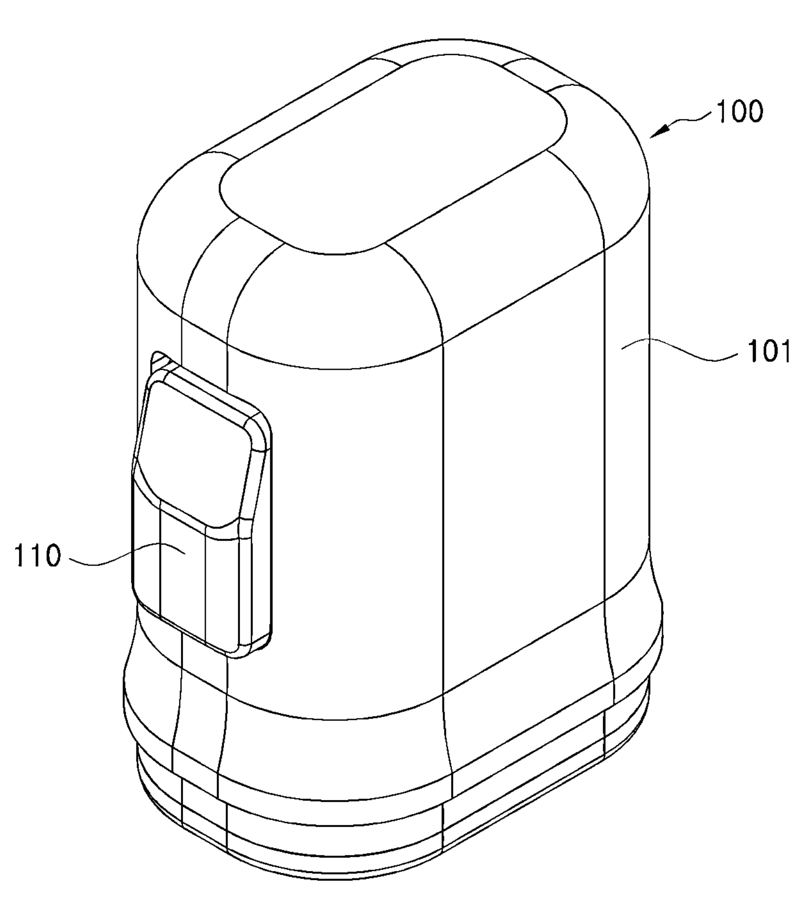
FIG. 6 is an exploded perspective view of schematically illustrating configuration of a protection cap according to an embodiment of the present disclosure.
Figure 6:
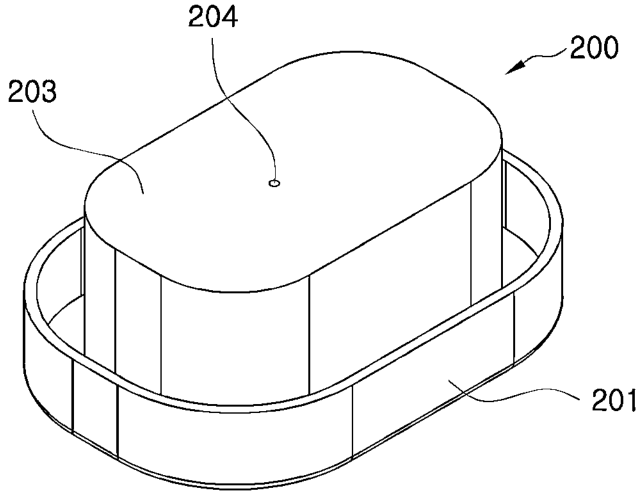
Figure 7:
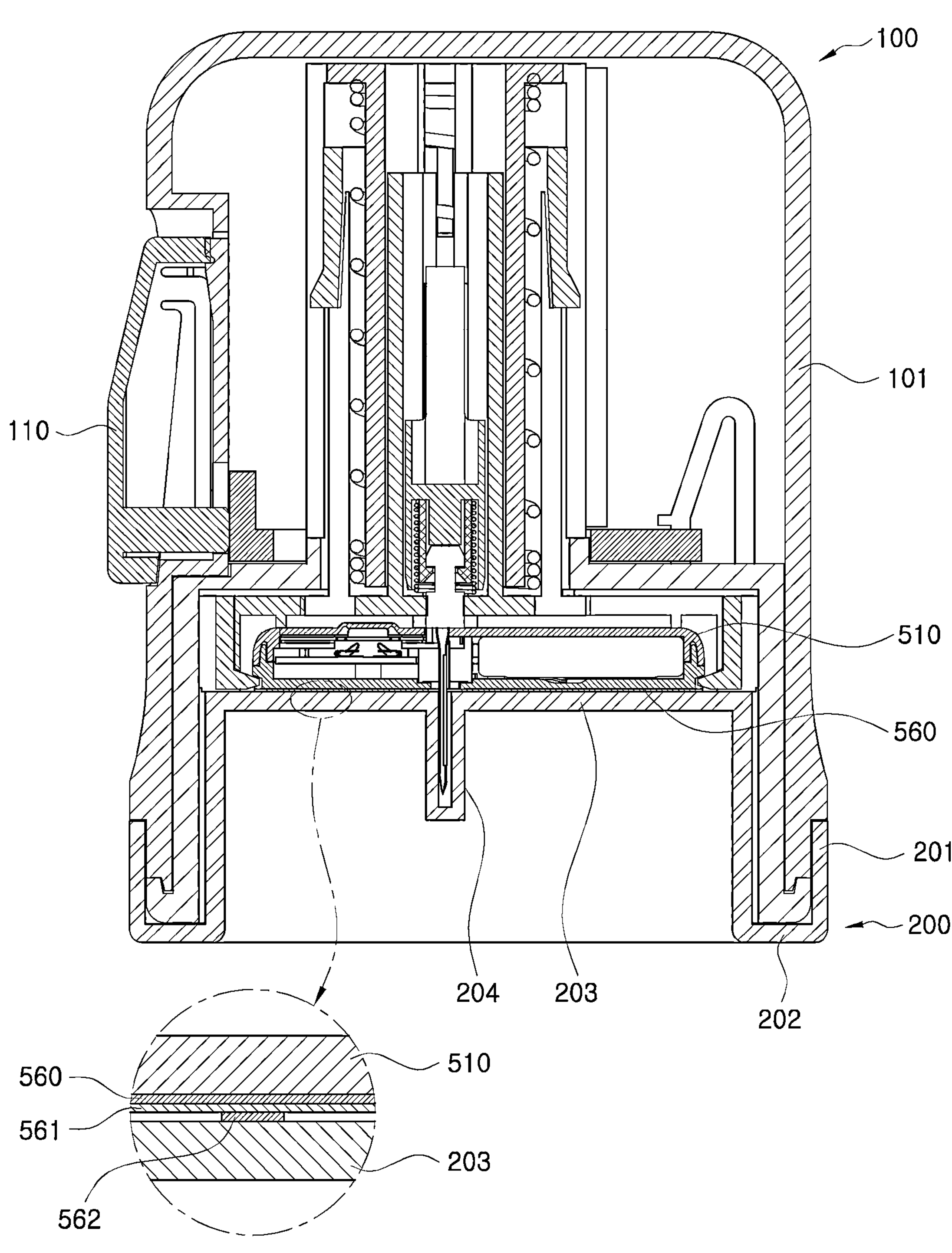
FIGS. 7 and 8 are views of illustrating operations for removing and separating a release paper as well as a protection cap according to an embodiment of the present disclosure.
Figure 8:
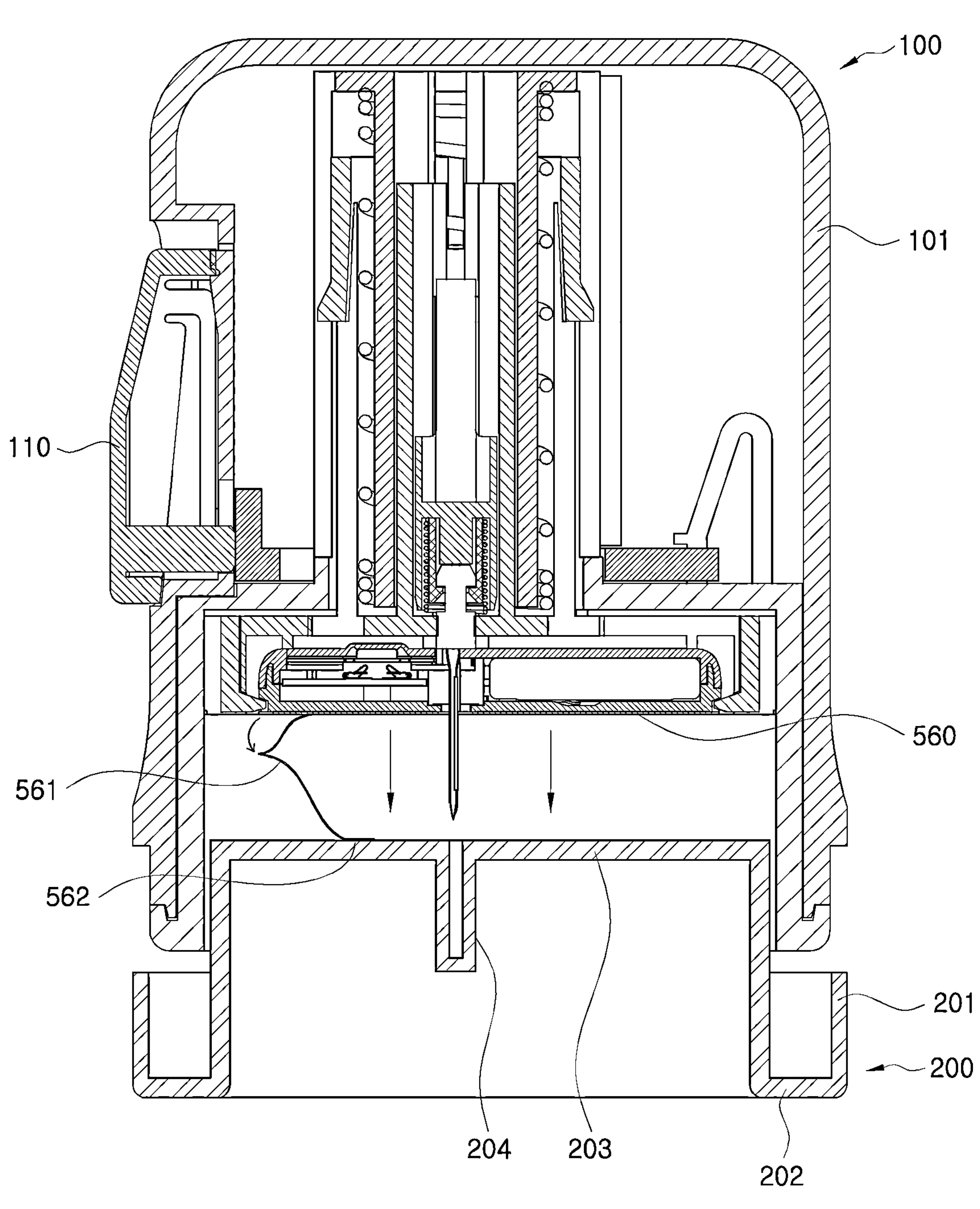

As illustrated in FIGS. 6 to 8, the protection cap (200) may comprise an outer side cover unit (201) covering and contacting an outer circumferential surface of the applicator (10) and formed to be coupled with one end portion of the applicator (10), an extension unit (202) extending from one end of the outer side cover unit (201) in a direction toward the inner center of the applicator (10), and an inner side supporting unit (203) upwardly extending from the extension unit (202) and configured to support a surface of the body attachable unit (20) contacting the human body inserted in the inside of the applicator (10). In this embodiment, at the center portion of the inner side supporting unit (203), the sensor protection unit (204) may be formed to partially downward-protrude to surround a sensor probe (521) downwardly protruding from a surface of the body attachable unit (20) contacting the human body and the needle unit (550).

Accordingly, the protection cap (200) can block the outside exposure of the body attachable unit (20) inserted in the inside of the applicator (10) as well as perform the function of supporting the body attachable unit (20), and may improve the overall structural stability of the applicator.

Meanwhile, as shown in FIGS. 7 and 8, the adhesive tape (560) and the release paper (561) are attached to a surface of the body attachable unit (20) which is to be contacted with the human body, and the release paper (561) of the adhesive tape (560) is configured to be separated and removed from the adhesive tape (560) together with the protection cap (200) in the process of separating the protection cap (200) from the applicator (10).

In this embodiment, the release paper (560) may be applied to the upper surface of the inner side supporting unit (203) of the protection cap (200), and may be attached to the inner side supporting unit (203) of the protection cap (200) through separate adhesive material (562). Accordingly, as illustrated in FIG. 7, the separate adhesive material (562) is adhered to one side of the lower surface of the release paper (561), and this adhesive material (562) is disposed between the upper surface of the inner side supporting unit (203) of the protection cap (200) and the release paper (561) and the lower surface of the adhesive material (562) is adhered to the upper surface of the inner side supporting unit (203). The adhesive strength of the adhesive material (562) may be greater than the adhesive strength between the release paper (561) and the adhesive tape (560). Accordingly, if the protection cap (200) is separated from the applicator (10), the release paper (561) adhered to the inner side supporting unit (203) of the protection cap (200) is also separated together with the protection cap (200) through the adhesive material (562) and separated and removed from the adhesive tape (560).

In this embodiment, at the release paper (561), two cutting lines (not shown) separated with a separation distance identical to a width of the adhesive material (562) are formed to be parallel to each other at some sections, and therefore, as illustrated in FIG. 8, in the process of separating the protection cap (200), the release paper (562) is separated and removed away from the adhesive tape (560) along the cutting lines together with the adhesive material (562) first and then as the separation operation of the protection cap (200) is being performed, i.e., the protection cap (200) keeps being downwardly moved with reference to a direction shown in FIG. 8, a portion of the release paper (562) except the cutting lines is pulled and separated and removed from the adhesive tape (560). By this operation of separating and removing the release paper, the separation-removal operation of the release paper (561) may be smoothly and stably performed.

The pressure button (110) is installed at the main case (100) for pressure operation the user, and a shooting plate (150) configured to be movable according to the pressure operation of the pressure button (110) may be movably coupled to the inside of the main case (100).

The plunger body (300) may be configured to be coupled and interlocked with the shooting plate (150) and fixed at the first location, and to be released from the interlock with the shooting plate (150) according to the movement of the shooting plate (150) and be moved to the second location by the elastic force of the plunger elastic spring (S1).

The main case (100) may comprise an outer case (101), wherein the pressure button (110) is installed to one side of the outer case (101), and an inner case (102) coupled at the inside of the outer case (101) and configured to guide a linear movement path of the plunger body (300), and the shooting plate (150) may be configured to be movable while being supported in the inner case (102).

Figure 9:
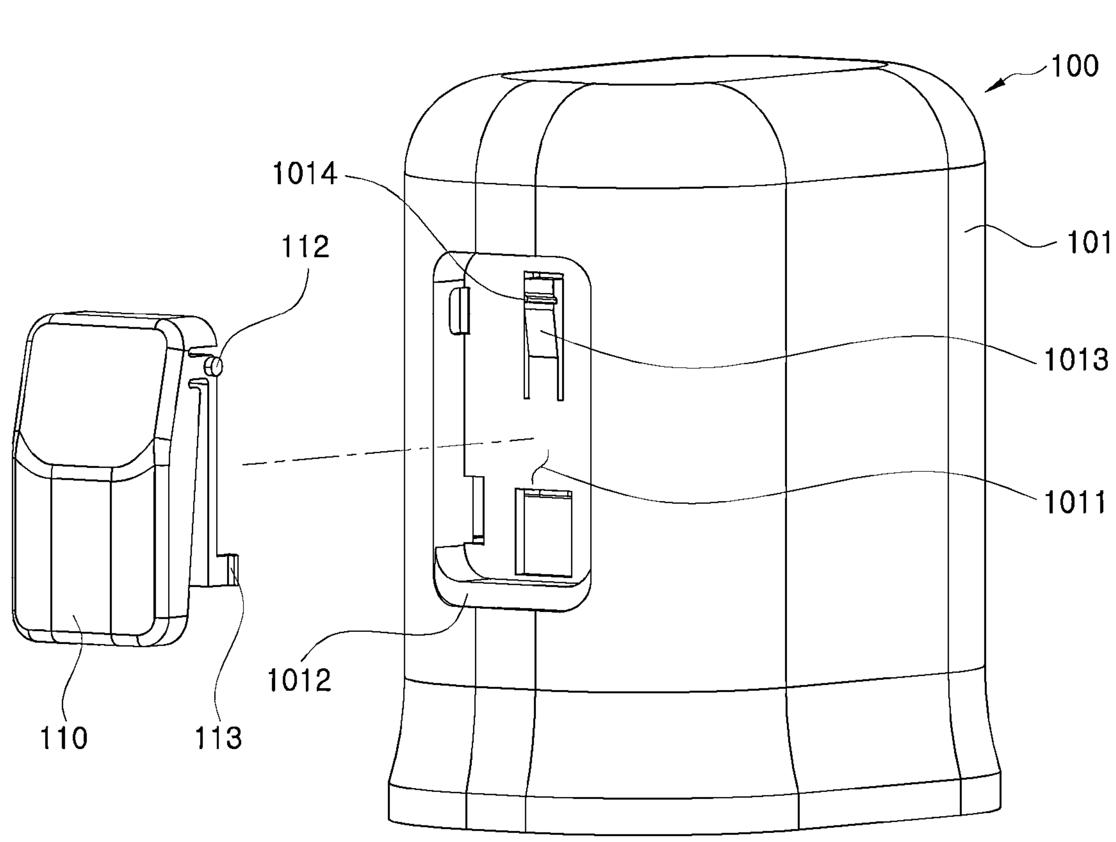
FIG. 9 is a perspective view of schematically illustrating a coupling structure of a pressure button according to an embodiment of the present disclosure.

The pressure button (110) is coupled to the outer case (101) in order to be capable of performing the operation of applying pressure, and as shown in FIG. 9, a button guide groove (1011) is formed at the outer case (101) so that the pressure button (110) can be coupled in order to be capable of performing the operation of applying pressure. The pressure button (110) is configured to be capable of the pressure operation by a structure that a portion of the pressure button (110) is configured to be rotatable around a hinge axis (112) formed at an upper end portion of the pressure button (110), a pressure rod (111) is formed at a lower end portion of the pressure button (110) to apply the pressure to the shooting plate (150), and a separate fixing hook (113) is formed at one side of the pressure button (110) to prevent separation and removal of the pressure button (110).

The pressure button (110) is installed to be configured to provide mode change between a safe mode blocking the pressure movement performed according to the pressure operation and a pressure standby mode capable of performing the pressure movement performed according to the pressure operation.

The pressure button (11) may be configured to, in a safe mode state, slidingly move along an exterior surface of the main case (100) for a certain section to change to a standby mode state. A hanging raised part (1012) is formed at a portion of the main case (100) where the pressure button (110) is coupled, in the safe mode state, the pressure button (110) is interlocked with the hanging raised part (1012) to block the pressuring movement, and as the sliding movement is from the safe mode state to the pressure standby mode state performed, the interlock from the hanging raised part (1012) is released to make the pressuring movement possible.

Figure 10:
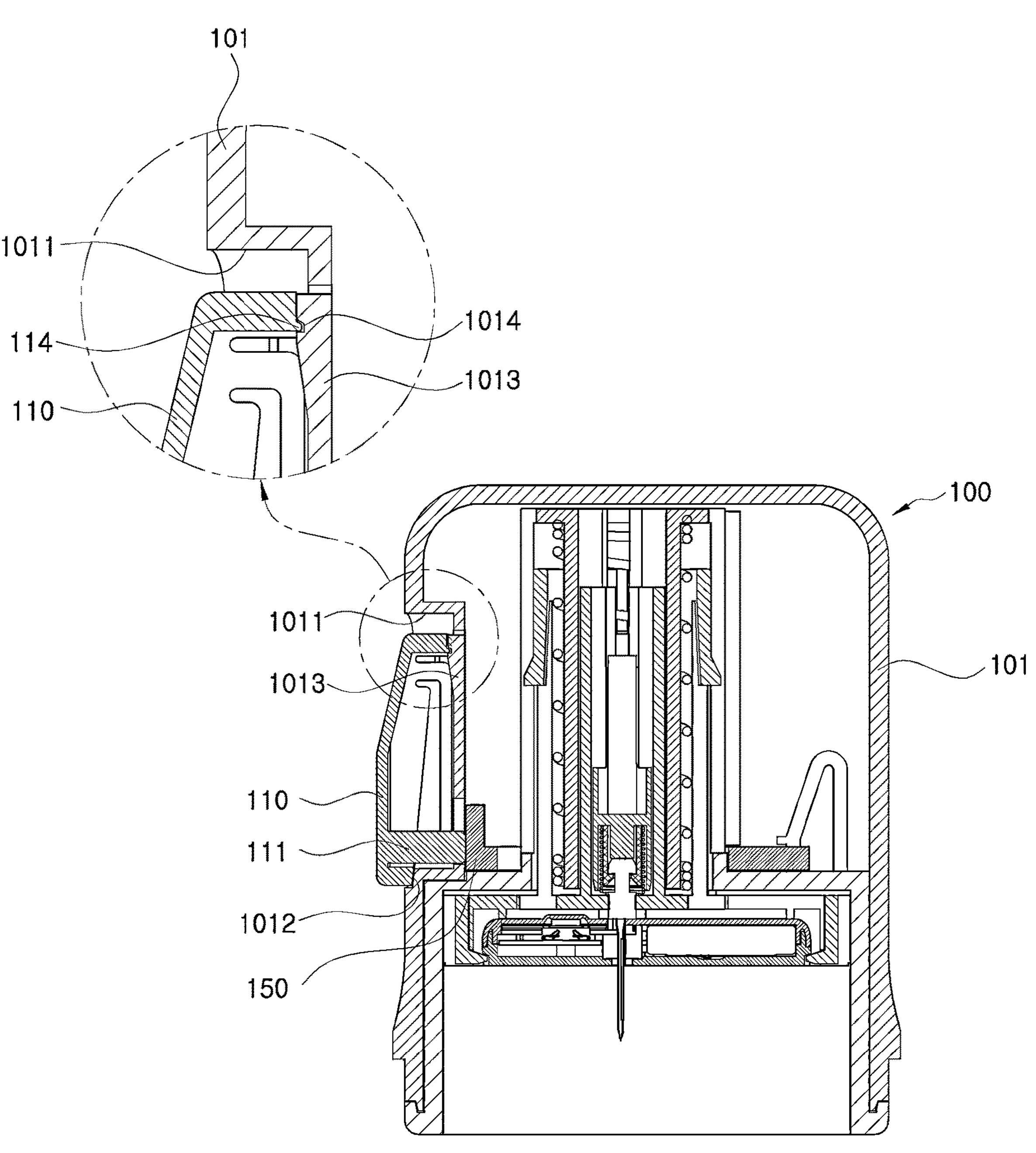
FIGS. 10 and 11 are views of schematically illustrating mode change structures of a pressure button according to an embodiment of the present disclosure.
Figure 11:
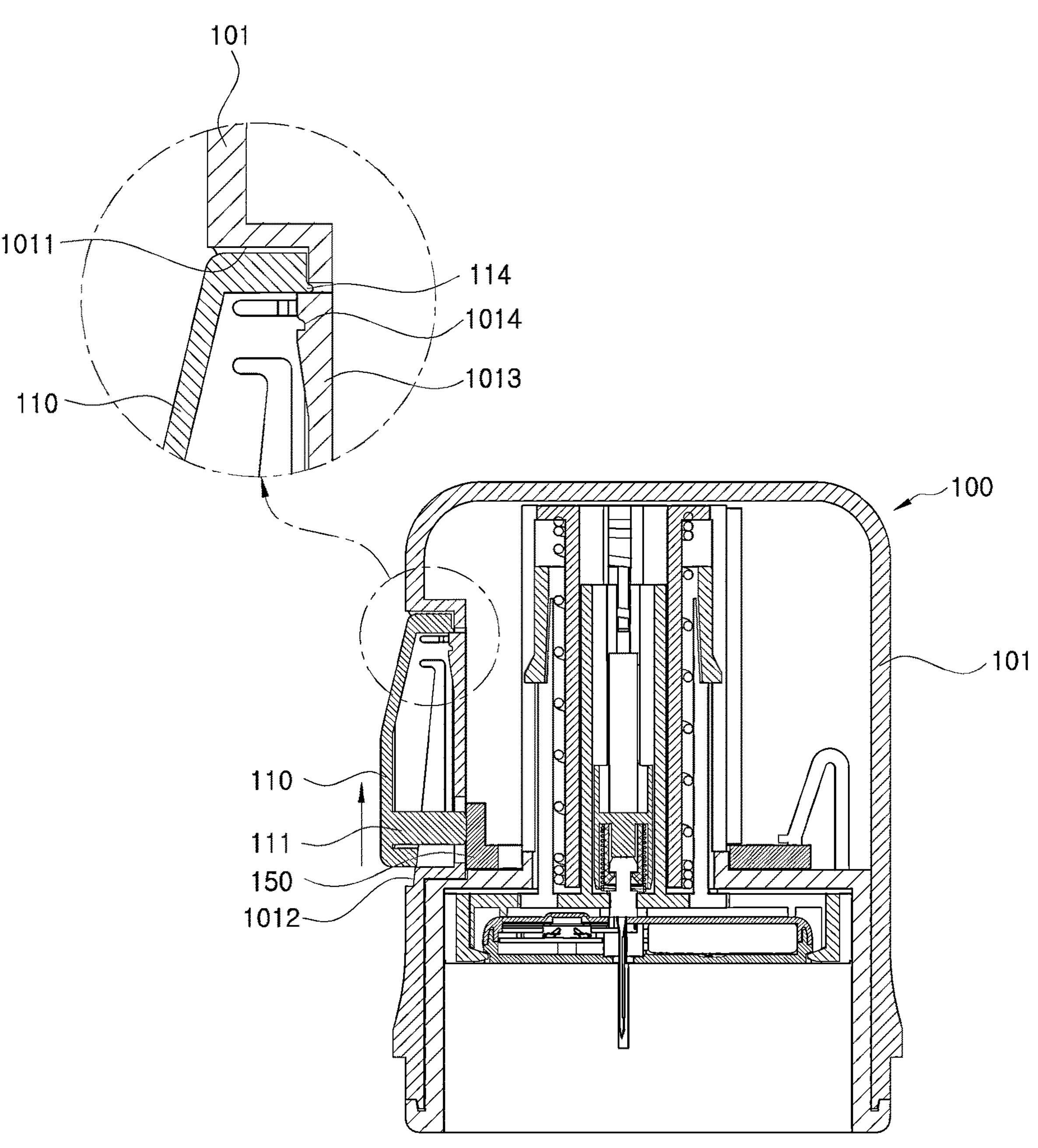

Accordingly, as illustrated in FIG. 10, in the safe mode state, the pressure button (110) is interlocked at the hanging raised part (1012) of the outer case (101) so that the pressurizing operation cannot be performed, and as illustrated in FIG. 11, when the pressure button (110) is upwardly moved to the pressure standby mode state, the interlock with the hanging raised part (1012) of the outer case (101) is released and it is possible to perform the pressurizing operation.

If the pressure button (110) in the safe mode state is slidingly moved to the pressure standby mode, the position of the pressure button (110) may be fixed not to return to the safe mode state.

For this, a fixing protrusion (114) is formed at one side of the pressure button (110), a transformable cut portion (1013) is formed at the bottom surface of the button guide groove (1011) of the outer case (101) and in a structure that a certain section is cut to be elastically transformable, the transformable cut portion (1013) comprises a receivable groove (1014) configured to be insertedly receive the fixing protrusion (114) when the pressure button (110) is positioned at the safe mode, and in a state that the movement of the pressure button (110) to the pressure standby mode is completed, an end portion of the pressure button (110) is interlocked with the fixing protrusion (114) to block the returning movement of the pressure button (110).

In such a structure, the pressure button (110) can perform pressurizing operation by manipulated by the user only in a state that it is slidingly moved to the pressure standard mode state, and therefore the pressure operation caused by the user's mistake can be prevented and it is possible to use safely.

Figure 12:
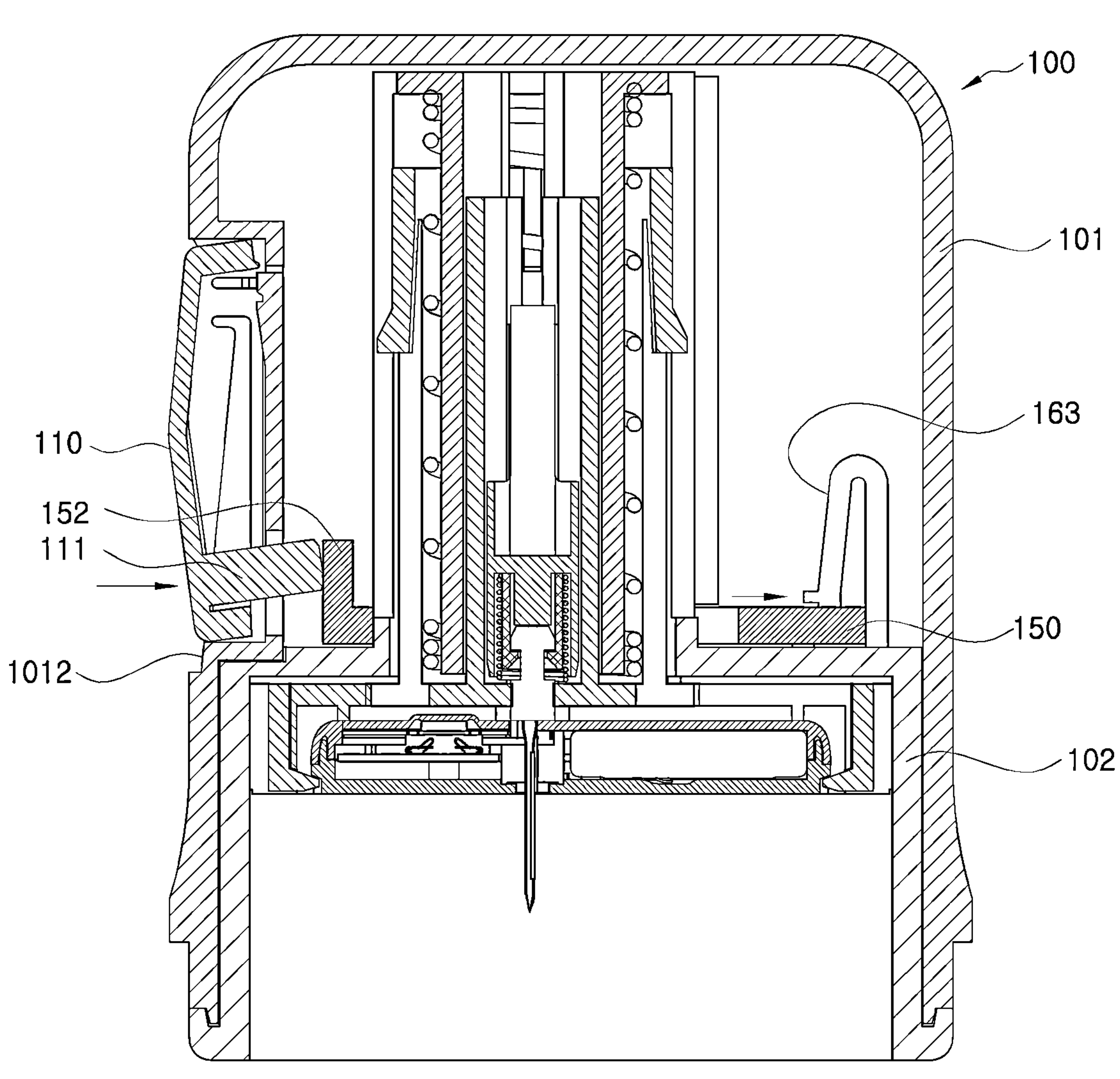
FIG. 12 is a view of schematically illustrating a pressurizing operation state of a pressure button according to an embodiment of the present disclosure.

If the pressure button (110) is changed to the pressure standby mode state and the pressurizing operation is performed as shown in FIG. 12, the pressure button (110) the pressure rod (111) of the pressure button (110) applies pressure to and moves the shooting plate (150).

The shooting plate (150) is supported in the inner case (102) and slidably movably coupled according to the pressurizing operation of the pressure button (110), and the plunger body (300) is interlocked with the shooting plate (150) at the first location and according to the movement of the shooting plate (150) the interlock with the shooting plate (150) is released and the plunger body (300) is moved to the second location by the elastic force of the plunger elastic spring (S1).

Figure 13:
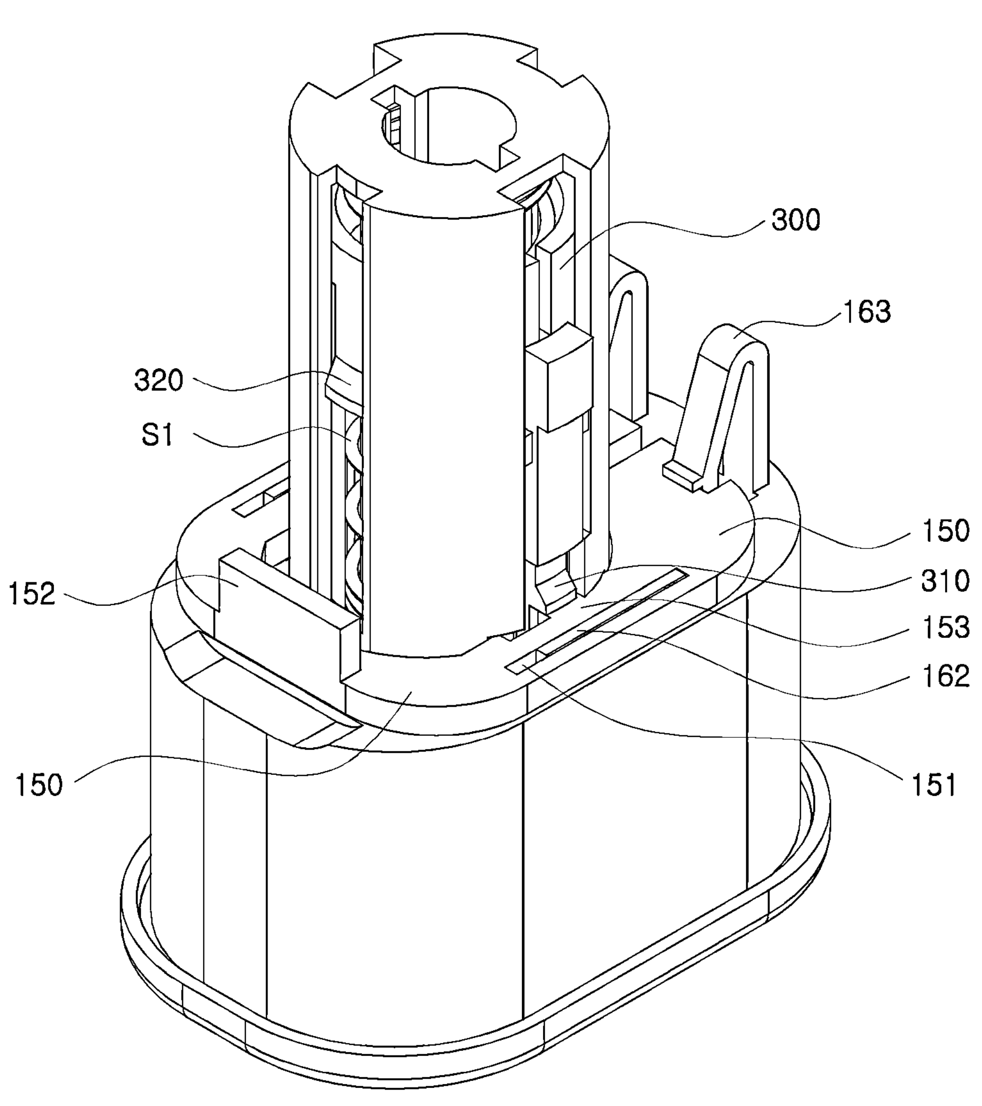
FIGS. 13 and 14 are perspective views of schematically illustrating movement states of a shooting plate caused by operations of a pressure button unit according to an embodiment of the present disclosure.
Figure 14:
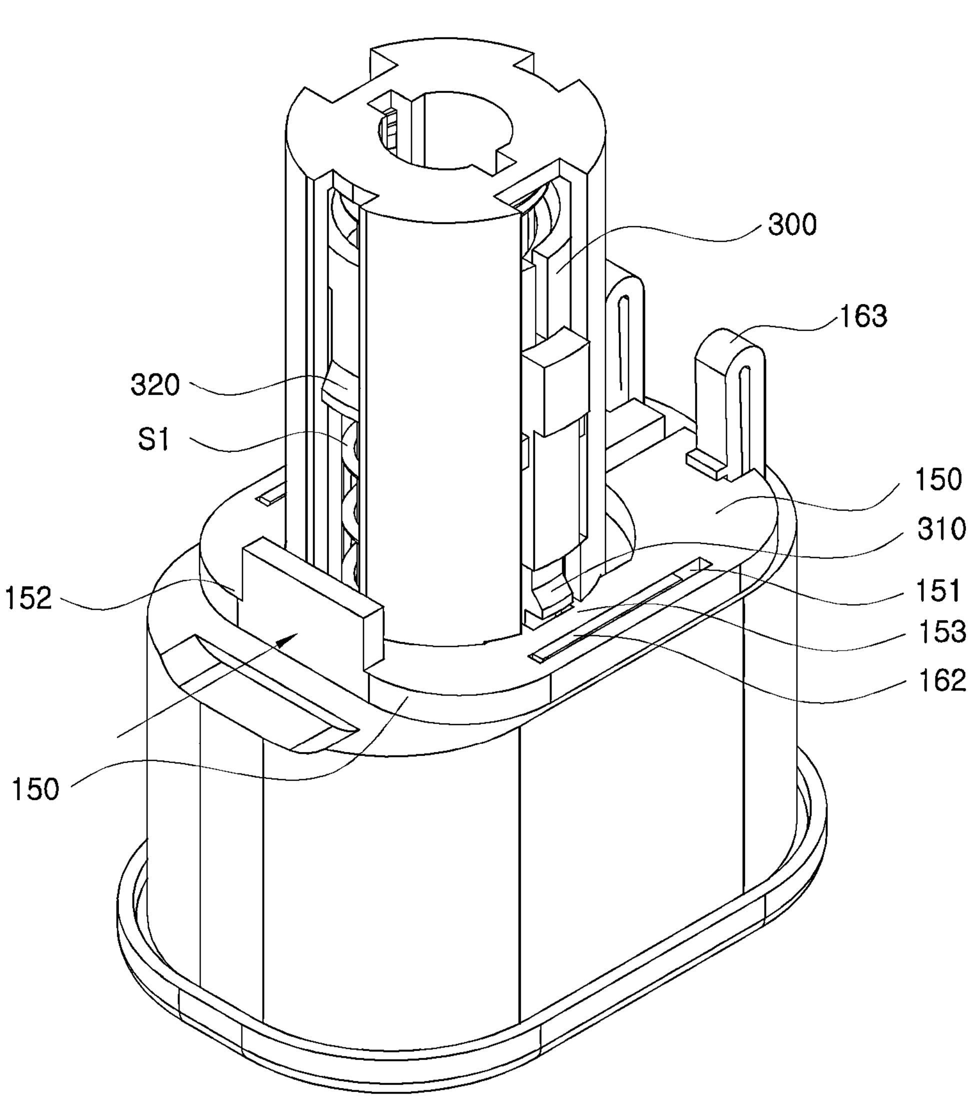

An interlock hook (310) is formed at the plunger body (300) to interlock with the shooting plate (150) as illustrated in FIGS. 12 and 13, the hanging protrusion part (153) interlockable with the interlock hook (310) of the plunger body (300) is formed at one side of the shooting plate (150), and the hanging protrusion part (153) may be configured to be released from the state interlocking with the interlock hook (310) as the shooting plate (150) is slidingly moved.

At the inner case (102), the guide rail (162) is formed to protrude to guide the slide movement path of the shooting plate (150), and the guide slot (151) is formed at the shooting plate (150) to insertedly guide the guide rail (162). And, an elastic structure (163) elastically supporting the shooting plate (150) in a direction opposite to a slide movement direction by the operation of the pressure button (110) is installed at the inner case (102). Accordingly, the shooting plate (150) is elastically supported by the pressure button (110) by the elastic force of the elastic structure (163), and therefore unless the pressure button (110) is manipulated for pressurization, the interlocking status of the plunger body (300) with the interlock hook (310) can be stably maintained.

Figure 15:
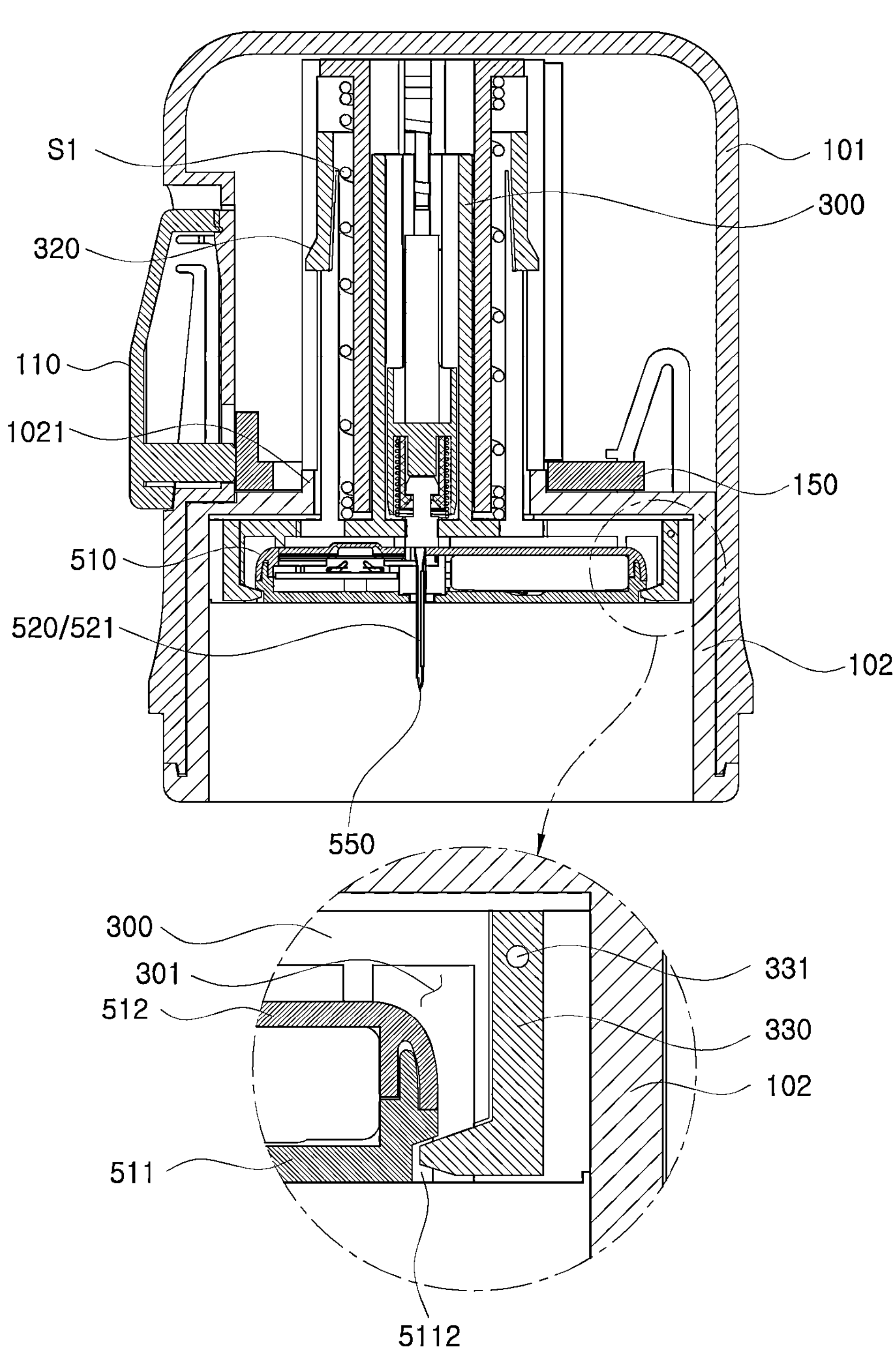
FIGS. 15 and 16 are views illustrating separation structures of an applicator and a body attachable unit according to an embodiment of the present disclosure.
Figure 16:
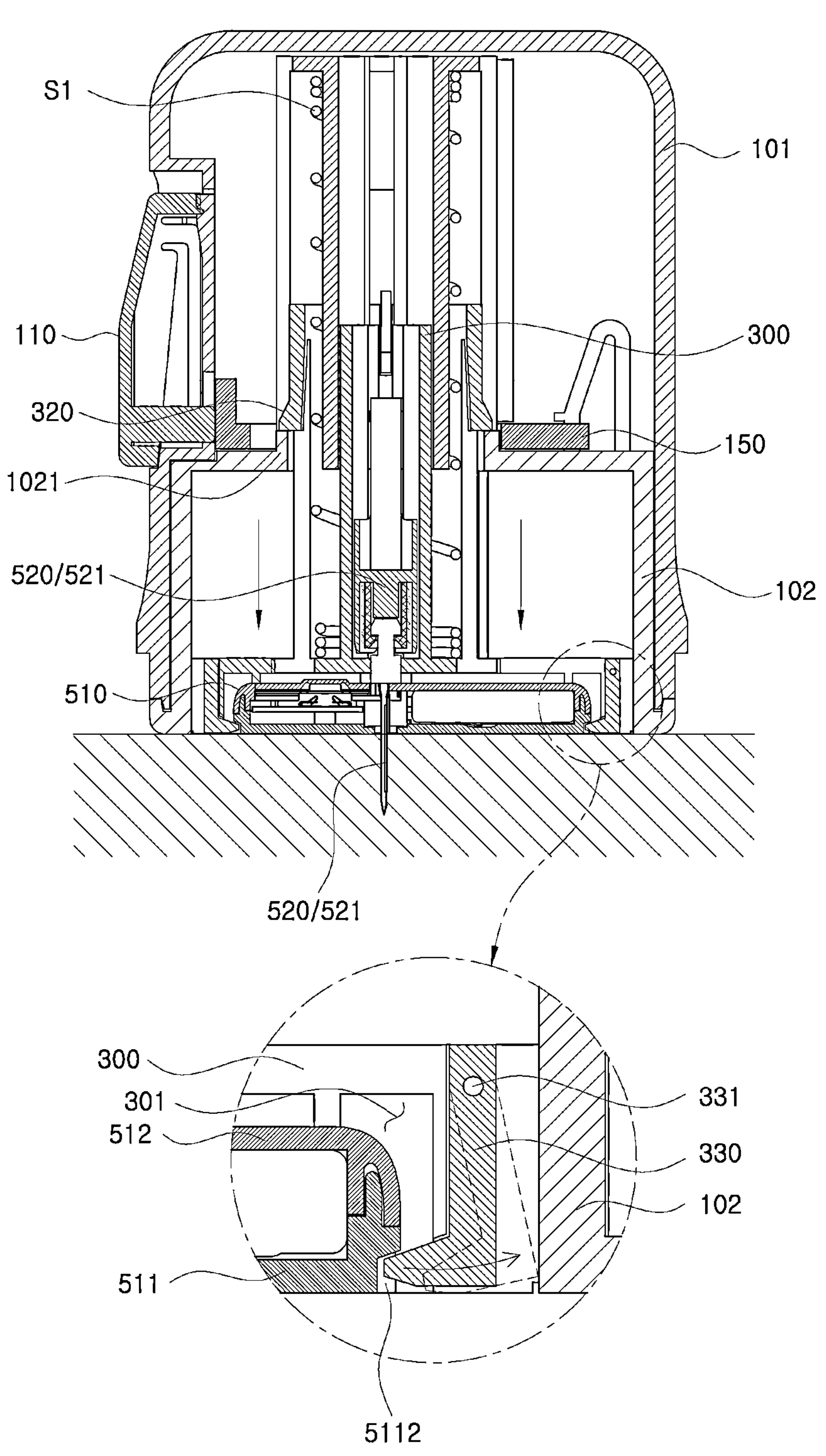

According to such a structure, when the user operates to pressurize the pressure button (110), the shooting plate (150) is slidingly moved, and this may result in releasing the interlocked state of the plunger body (300) and the shooting plate (150) and the plunger body (300) is outwardly discharged from the first location to the second location as shown in FIGS. 15 and 16.

A stopper protrusion (320) may be formed at the plunger body (300) to limit a range movable to the second location, and as the plunger body (300) is moved to the second location, the stopper protrusion (320) can limit the movement of the plunger body (300) by a way of being interlocked with one side of the inner case (102). Accordingly, the plunger body (300) can be moved up to the second location by the stopper protrusion (320), and the plunger body (300) cannot be outwardly discharged from the main case (100) over that range. In this embodiment, at the inner case (102), the plunger body (300) is interlocked with the stopper protrusion (320) in a state that the plunger body (300) is moved to the second location and a stopper fixing unit (1021) may be formed to limit the movement of the stopper protrusion (320).

Additionally, a sensor receiving unit (301) is formed at one end portion of the plunger body (300) so that the body attachable unit (20) is insertedly received, and the body attachable unit (20) is insertedly received by the sensor receiving unit (301) and linearly move together with the plunger body (300) from the first location to the second location. As the plunger body (300) and the body attachable unit (20) are linearly moved to the second location, the sensor probe (512) and the needle unit (550) of the body attachable unit (20) are inserted into the human body.

In this embodiment, a sensor fixing hook (330) fixedly coupling the body attachable unit (20) by being interlockedly coupled with the body attachable unit (20) inserted to the sensor receiving unit (301) is installed at an edge of the sensor receiving unit (301). An interlock coupling groove (5112) is formed at both end portions of the body attachable unit (20) to be interlocked with the sensor fixing hook (330) in a state that the body attachable unit (20) is inserted into the sensor receiving unit (301).

The sensor fixing hook (330) is coupled elastically rotatable around a rotary axis (331), in a state that the plunger body (300) is positioned at the first location as shown in FIG. 15 the sensor fixing hook (33) is elastically supported and pressurized in an inward direction so that the sensor fixing hook (330) is interlockedly coupled with the interlock coupling groove (5112) of the body attachable unit (20), and in a state that the plunger body (300) is positioned at the second location as illustrated in FIG. 16 the sensor fixing hook (330) is configured to be released from the interlock with the interlock coupling groove (5112) of the body attachable unit (20) in the operation of separating the applicator (10) from the body attachable unit (20). The operation of releasing the sensor fixing hook (330) from the interlock with the body attachable unit (20) can be performed in a way that the rotary shaft (331) twistingly and elastically rotates.

Although not illustrated, a hook guide unit (not shown) is formed on the inner surface of the inner case (102) and the hook guide unit pressurizes the sensor fixing hook (330) in an inward direction to be interlocked with the body attachable unit (20) and has a cross-sectional shape having a structure that the sensor fixing hook (330) is released from the pressurization in the state of the plunger body (300) moved to the second location. Therefore, the hook guide unit may have a structure with convex and concave surfaces on the inner surface of the inner case (102), the convex surface applies pressure to the sensor fixing hook (330) and the concave surface releases the sensor fixing hook (330) from the pressure application, and the concave is formed to release the sensor fixing hook (330) from the pressure application in a state that the sensor fixing hook (330) is moved together with the plunger body (300) to the second location.

Meanwhile, because the embodiment of the present disclosure is manufactured in a state that the body attachable unit (20) is inserted in the applicator (10), the reuse of the body attachable unit (20) by inserting again another body attachable unit (20) to the applicator (10) may be prevented as described above.

For this purpose, the main case (100) includes return prevention means for preventing the plunger body (300) returning to the first location after the plunger body (300) is moved to the second location.

Figure 17:
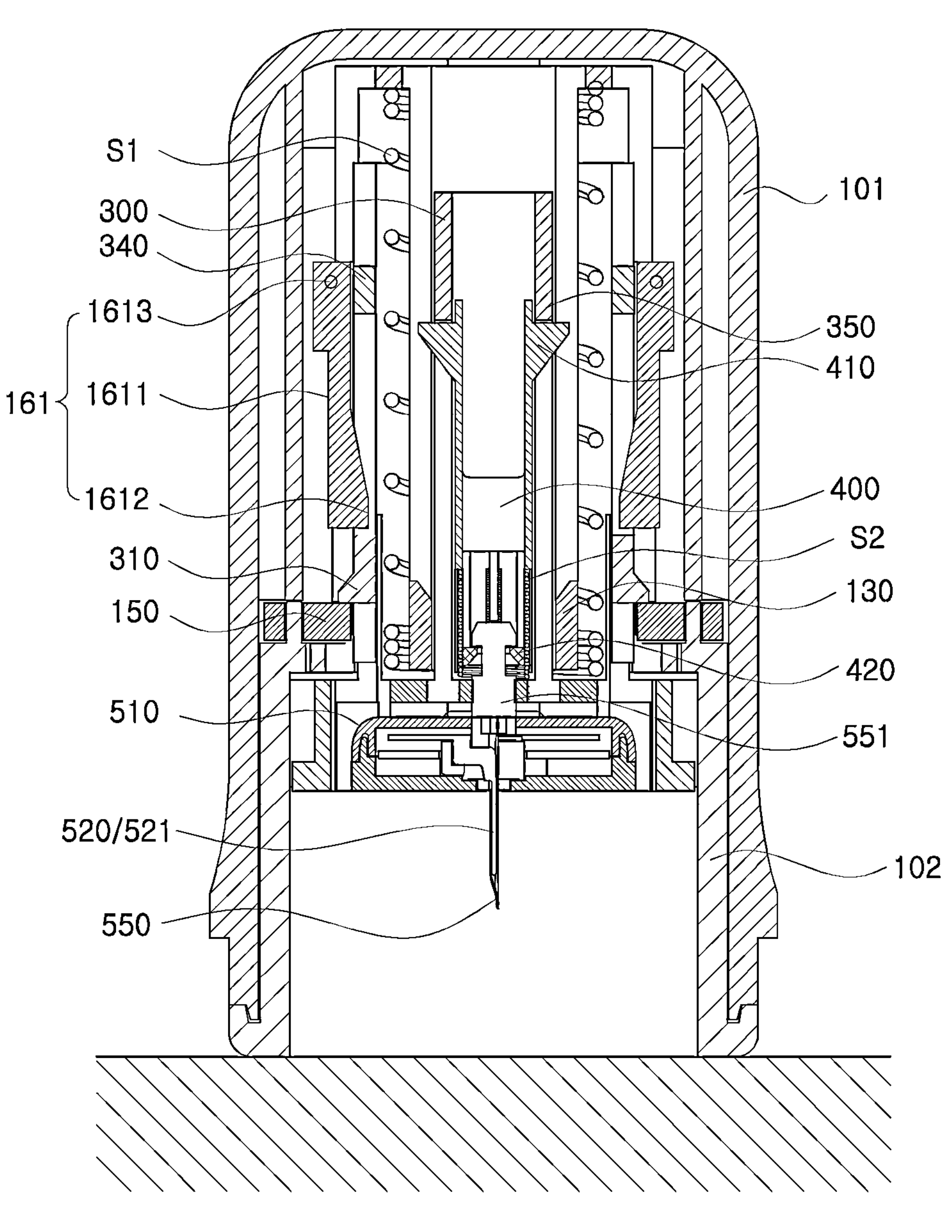
FIGS. 17 to 19 are views illustrating structures for preventing reuse of an applicator according to an embodiment of the present disclosure.
Figure 18:
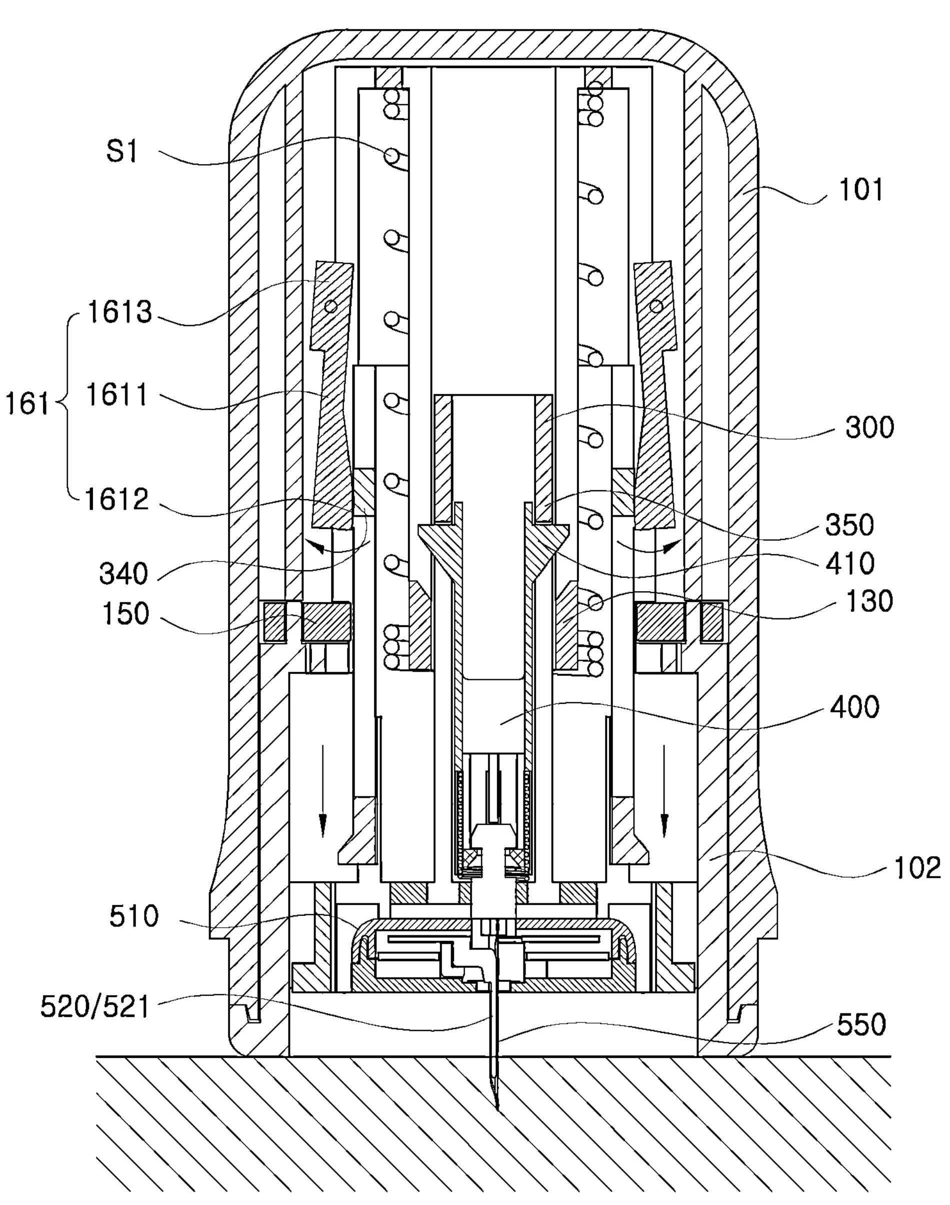
Figure 19:
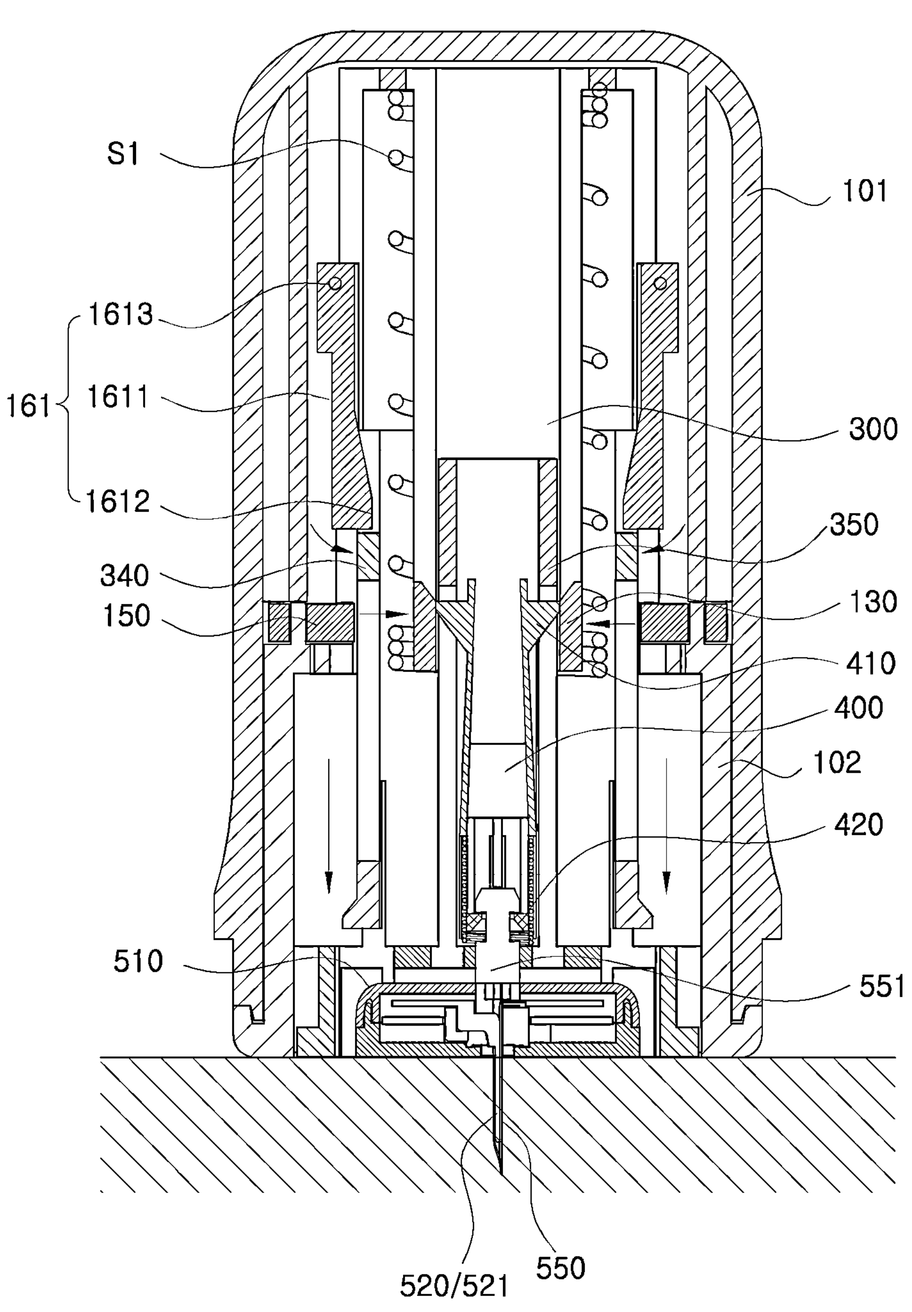

As illustrated in FIGS. 17 to 19, the return prevention means may be configured to comprise a interlocking body (340) formed on one side of the plunger body (300), and a return prevention hook (161) formed at the inner case (102)

and configured to prevent the returning movement of the plunger body (300) by being interlockedly coupled with the interlocking body (340) of the plunger body (300) when the downward movement of the plunger body (300) from the first location to the second location is completed.

The return prevention hook (161) is configured to be interlocked with the interlocking body (340) by elastic restoring force in the operation of be interlocked with the interlocking body (340). Specifically, the return prevention hook (161) may be configured to have a structure comprising a rotatable body (1611) elastically rotatably coupled around a rotary shaft (1613) and at one side of the inner case (102), and a hook body (1612) slantly protruding from the inner side surface of the rotatable body (1611) in a downward and inward direction. In this embodiment, the rotary axis (1613) is configured to elastically support the rotatable body (1611) in a inward and protruding direction of the hook body (1612) by applying elastic force according to a material character of elastic material.

By this return prevention hook (161), the returning movement of the plunger body (300) to the first location after the movement from the first location to the second location is completed is prevented, and therefore, the user's inserting and using another body attachable unit (20) again at the user's discretion may be prevented.

The state of the operation of the return prevention hook (161) will be described in detail, and if the plunger body (300) is moved to the second location by the operation of the pressure button (110) in a state that the plunger body (300) is positioned at the first location as shown in FIG. 17, the hook body (1612) is pressurized by the interlocking body (340) of the plunger body (200) during the movement of the plunger body (300) to the second location as illustrated in FIG. 18, and then the return prevention hook (161) is elastically rotated in a clockwise direction (an outward direction) around the rotary axis (1613). After that, if the movement of the plunger body (300) to the second location is completed as shown in FIG. 19, the return prevention hook (161) is returned by being elastically rotated around the rotary shaft (1613) in a count-clockwise direction (an inward direction). Likewise, as the return prevention hook (161) is elastically return-rotated, the lower portion of the return prevention hook (161) is interlocked with the upper portion of the interlocking body (340) of the plunger body (300), and therefore the returning movement of the plunger body (300) to the first location in a state interlocking with the return prevention hook (161) and the interlocking body (340) is prevented.

Meanwhile, the applicator (10) is configured to extract and remove the needle unit (550) of the body attachable unit (20) from the human body at a time of the completion of outward discharge movement of the body attachable unit (20) from the first location to the second location, and for this purpose, the applicator (10) may comprise a needle extracting means (N) configured to upwardly move the needle unit (550) and extract and remove the needle unit (550) from the human body at a time of the completion of the movement of the plunger body (300) from the first location to the second location.

The needle extracting means (N) may comprise a needle extracting body (400) coupled with the needle head (551) of the needle unit (550) and linearly move along the inner case (102) from the first location to the second location together with the plunger body (300) by being interlocked with the plunger body (300), and a needle extracting elastic spring (S2) applying elastic force to the needle extracting body (400) in a direction that the needle extracting body (400) upwardly moves toward the first location.

The needle extracting body (400) is interlockedly coupled to the plunger body (300), and for this purpose, a separate elastic hook (410) configured to be elastically transformable is provided at the needle discharge body (400), and the elastic hook (410) is elastically biased in a direction interlockedly coupled to the hook interlocking unit (350) of the plunger body (300). Accordingly, if the plunger body (300) is linearly moved from the first location to the second location according to the operation of the pressure button (110), the needle extracting body (400) is also linearly moved to the second location together with the plunger body (300).

In this embodiment, a needle extracting pressurizing unit (130) configured to pressurize the elastic hook (410) in an inward direction so that the elastic hook (410) is released from the interlock with the hook interlocking unit (350) of the plunger body (300) according to the movement of the needle extracting body (400) to the second location is included in the inner case (102).

Figure 20:
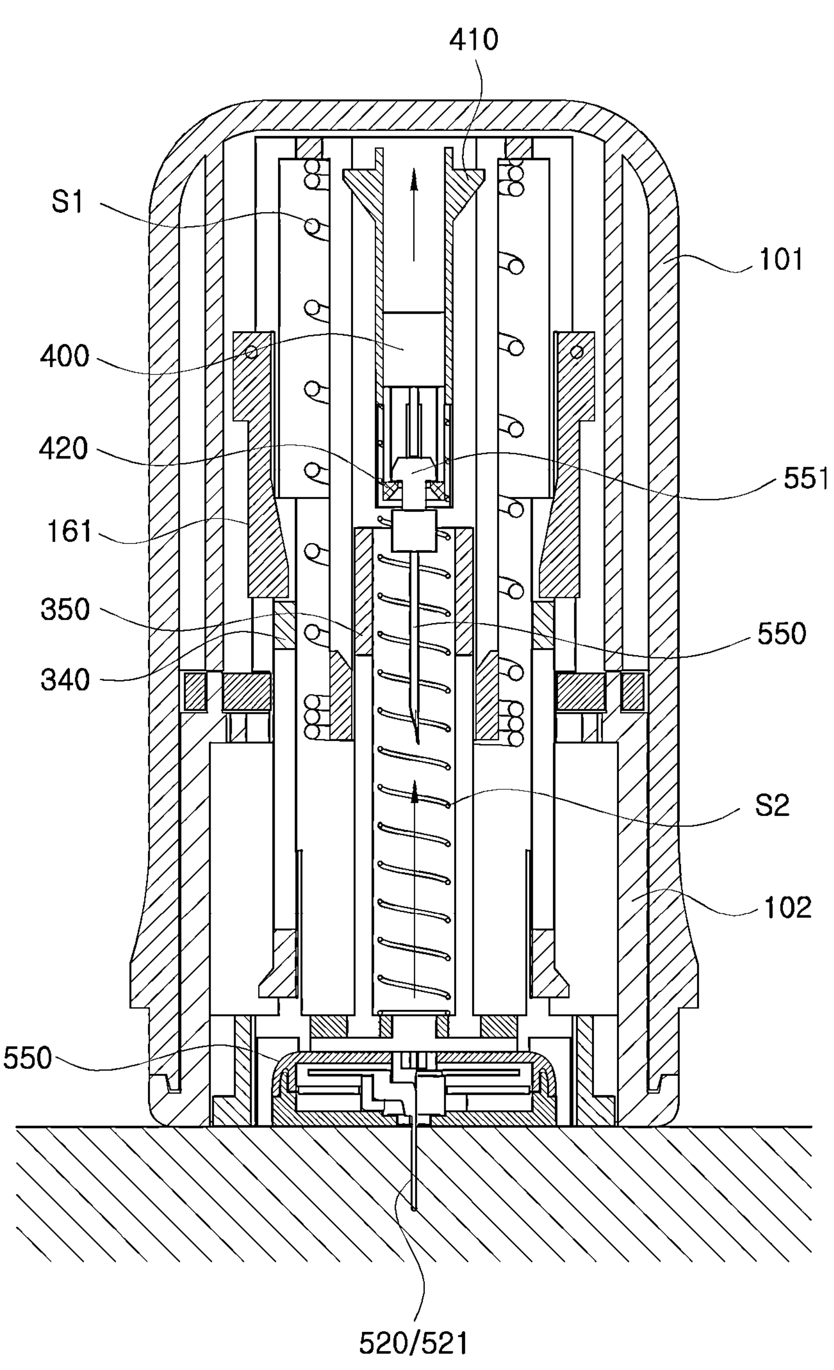
FIG. 20 is a view illustrating an operation structure of needle extracting means according to an embodiment of the present disclosure.

If the pressure is applied to the pressure button (110) according the structures described above, the needle extracting body (400) linearly moves from the first location to the second location together with the plunger body (300) as illustrated in FIG. 19, at the same time the elastic hook (410) of the needle extracting body (400) is pressurized by the needle extracting pressurizing unit (130) and is released from the state interlocked with the hook interlocking unit (350), and therefore the needle extracting body (400) is upwardly return-moved toward the first location by the elastic force of the needle extracting elastic spring (S2) as shown in FIG. 20.

In this embodiment, because the needle extracting body (400) is coupled with the needle head (551) of the needle unit (550) through an end of a needle head coupling unit (420), during the operation that the needle extracting body (400) is upwardly return-moved, the needle unit (550) is moved together and removed from the human body. The needle head coupling unit (420) is formed at the lower end portion of the needle extracting body (400) by a form of being interlockedly coupled to the coupling groove (552) formed at the needle head (551).

Meanwhile, according to the movement of the plunger body (300) to the second location by the elastic force of the plunger elastic spring (S1) the sensor probe (521) and the needle unit (550) of the body attachable unit (20) is inserted into the human body, but the needle unit (550) may be slightly retracted in a direction opposite to a human body insertion direction by reaction force generated by insertion resistance during the process of inserting the needle unit (550) to the human body. In this case, because the sensor probe (521) is not inserted into the human body to a proper depth, the retraction of the needle unit (550) needs to be prevented. For this, a needle supporting block may be coupled to the needle attachable body (400), and the needle supporting block is configured to downwardly support an upper end of the needle unit (550) so that the needle unit (550) cannot be upwardly moved with respect to the needle extracting body (400).

Next, use states of the assembly of the sensor applicator described above will be described with respect to FIGS. 21 to 25.

FIGS. 21 to 25 are views illustrating use states of a continuous blood glucose measurement apparatus according to operation order step by step according to an embodiment of the present disclosure.

Figure 21:
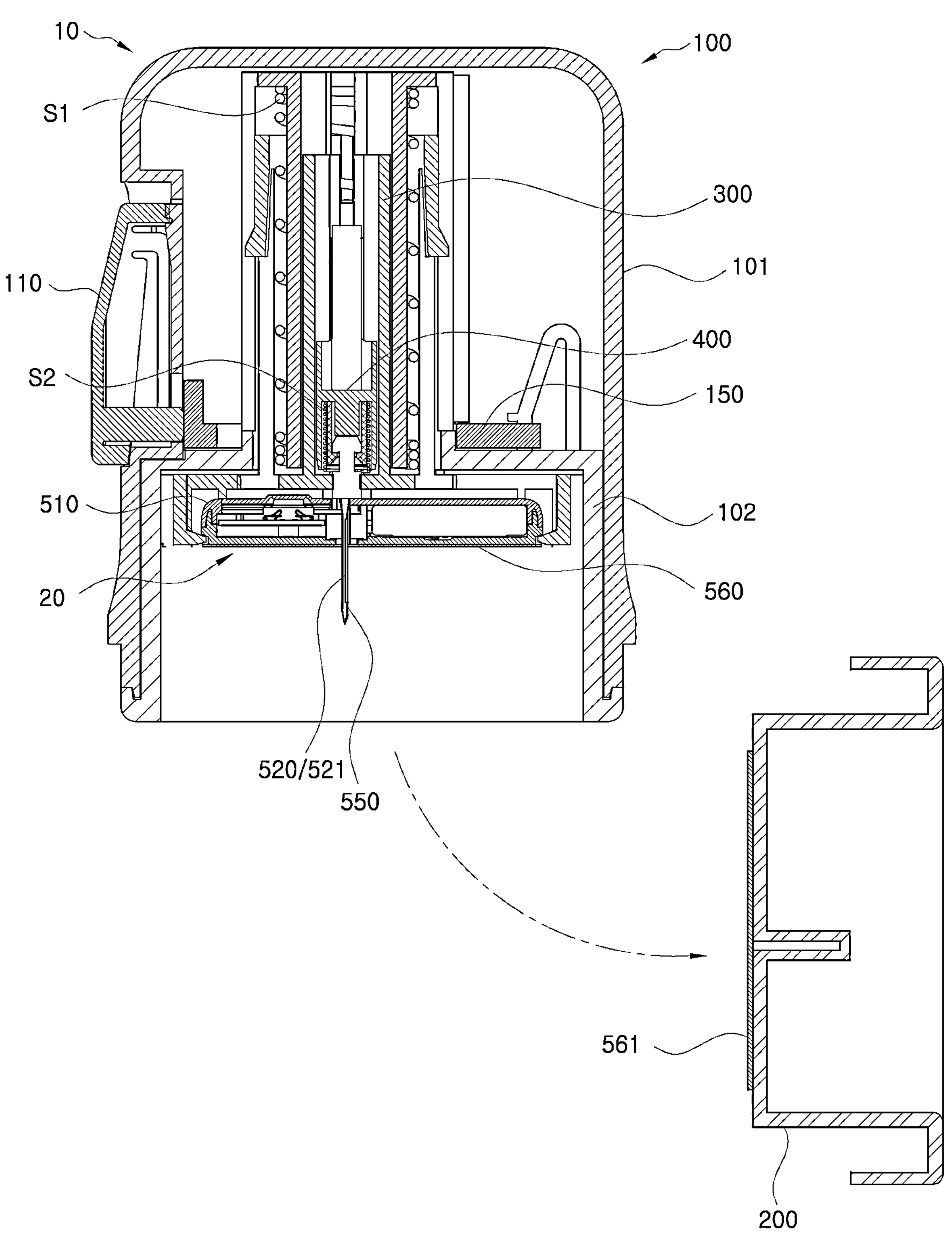
FIGS. 21 to 25 are views illustrating use states of a continuous blood glucose measurement apparatus according to operation order step by step according to an embodiment of the present disclosure.

First, as illustrated in FIG. 21, the protection cap (200) of the applicator (10) is separated. In the operation of separating the protection cap (200), the release paper (561) of the adhesive tape (560) of the body attachable unit (20) is separated together with the protection cap (200) and removed from the adhesive tape (560). After that, the sensor applicator assembly is located on a position of the human body to attach the body attachable unit (20), and in this state, after changing a mode of the pressure button (110) from the safe mode to the pressurization standby mode, the pressure button (110) is operated to be pressurized.

Figure 22:
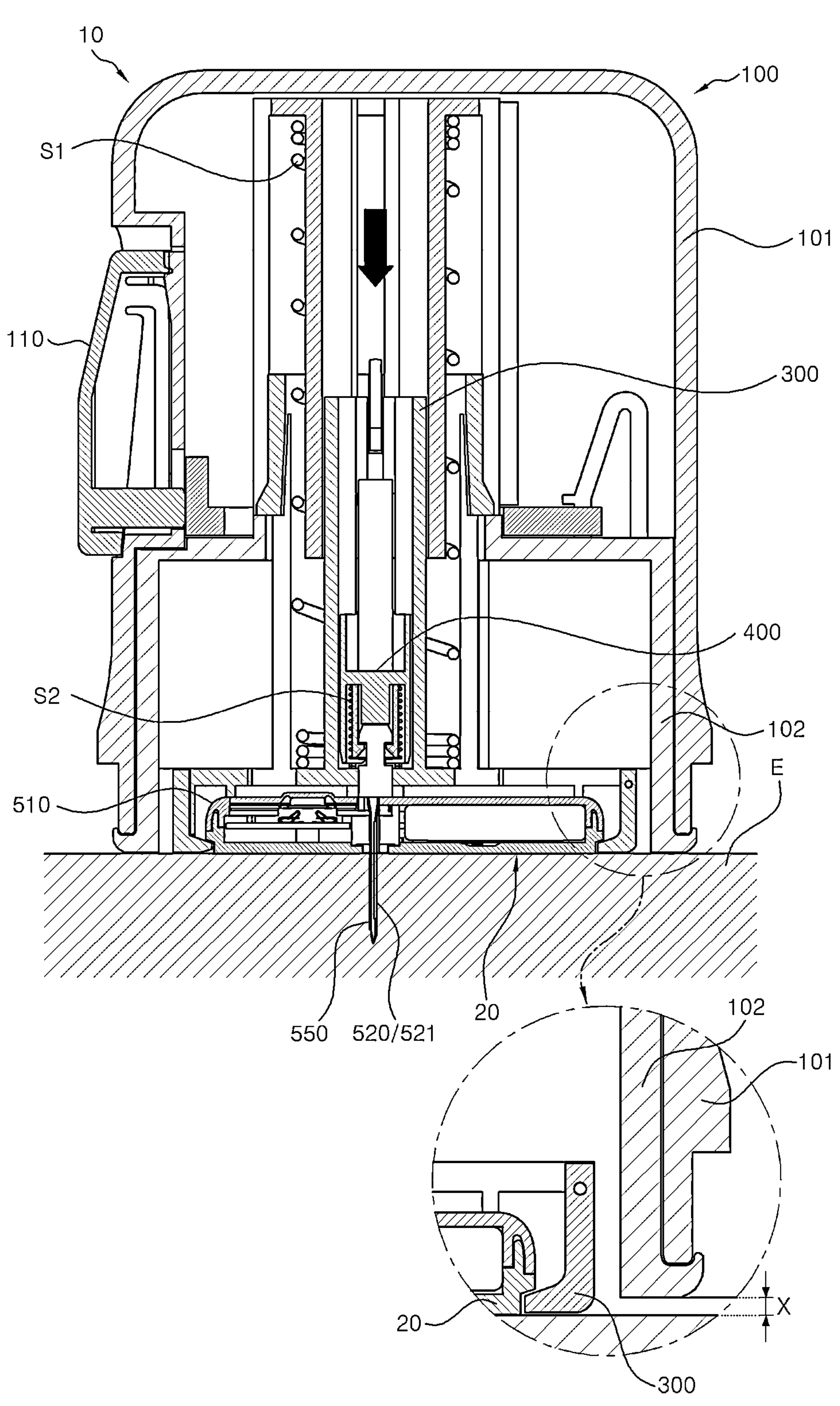
Figure 23:
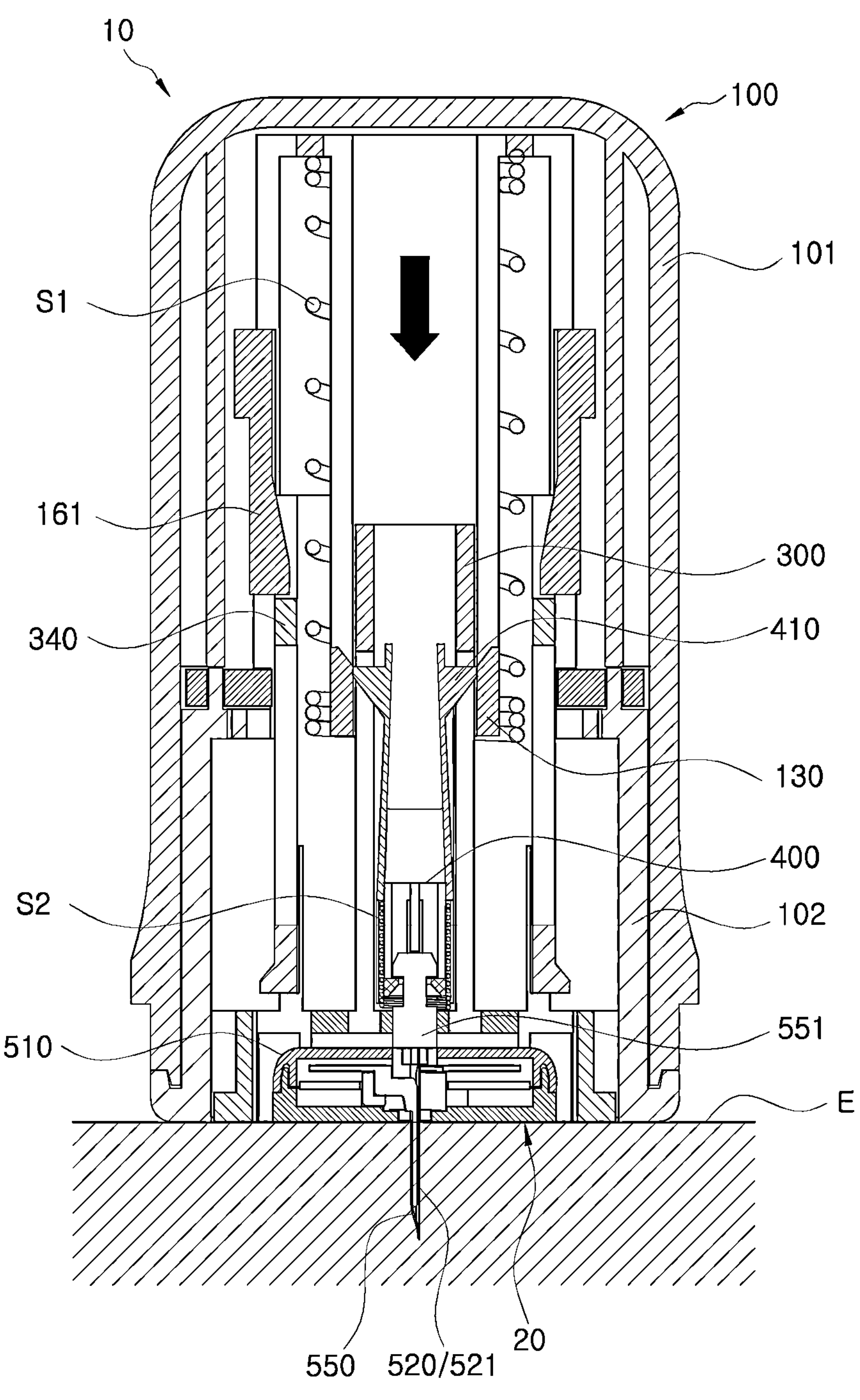

If the pressurizing operation is performed to the pressure button (110), the state interlocking with the plunger body (300) is released by the movement of the shooting plate (150), therefore the plunger body (300) is downwardly moved in a direction outwardly discharged by the plunger elastic spring (S1) as illustrated in FIGS. 22 and 23, and in this process, the needle unit (550) and the sensor probe (521) of the body attachable unit (20) is inserted into the human body (E). In this time, the body attachable unit (20) is adhered to a surface of the human body (E) by the bottom surface of the adhesive tape (560). Likewise, if the plunger body (300) is moved in an outwardly discharged direction, the plunger body (300) is interlocked by the return prevention hook (161) of the inner case (102) and therefore the plunger body (300) cannot upwardly move again as illustrated in FIG. 23. Accordingly, an applicator (10) which is already used cannot be reused again.

Meanwhile, according to an embodiment of the present disclosure, as illustrated in FIG. 22, in a state that the plunger body (300) is moved to the second location which is an outwardly discharging direction, the plunger body (300) and a lower surface of the body attachable unit (20) to which the plunger body (300) is coupled are formed to have the same height as the lower surface of the main case (100). However, as illustrated in the enlarged view of FIG. 22, the lower surface of the plunger body (300) may further downwardly protrude than the lower surface of the main case (100) by a distance X, and therefore the lower surface of the body attachable unit (20) coupled to the plunger body (300) also further protrudes than the lower surface of the main case (100) by the distance X.

Like this, the plunger body (300) is configured to further protrude from the opening of the main case (100) during the elastic movement of the plunger body (300), and therefore the body attachable unit (20) coupled to the plunger body (300) may be firmly attached to the surface of the human body, and specially, even when the user slightly moves the main case (100) upwardly because of fear during the process that the user operates the applicator, the body attachable unit (20) may be stably pressurized and contacted to the surface of the human body because the plunger body (300) further protrudes than the opening of the main case (100).

If the plunger body (300) is downwardly moved, the sensor fixing hook (330) of the sensor receiving unit (301) can be received from a state interlockedly coupled with the body attachable unit (20) as illustrated in FIG. 23. Additionally, the elastic hook (410) of the needle extracting body (400) is pressurized in an inward direction by the needle extracting pressurizing unit (130) of the inner case (102) and the state interlocked with the plunger body (300) is released.

Figure 24:
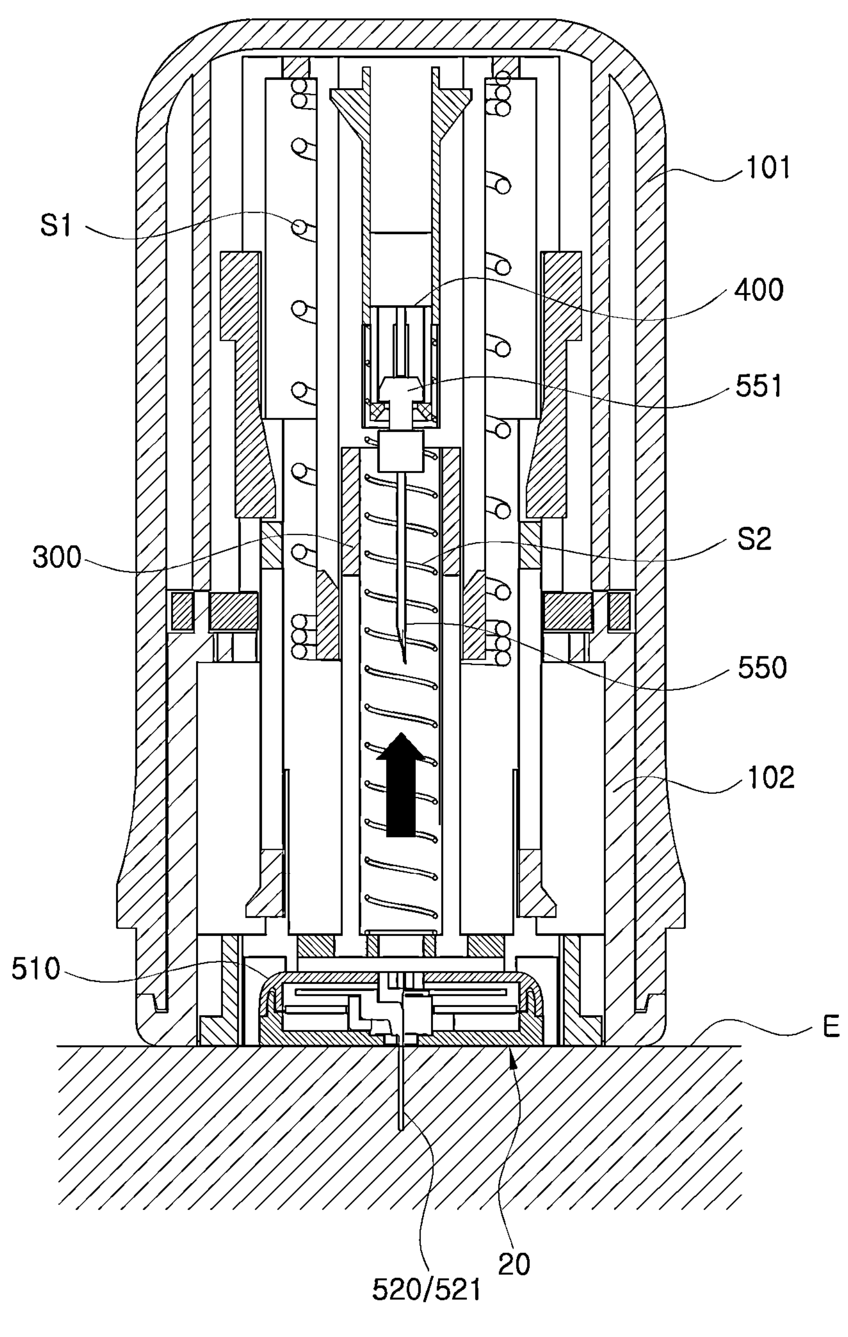

Accordingly, if the plunger body (300) is downwardly moved, at the same time the needle extracting body (400) is upwardly return-moved by the needle extracting elastic spring (S2) as illustrated in FIG. 24. In this time, because the needle unit (550) is upwardly moved together with the needle extracting body (400), the needle unit (550) is extracted and removed from the human body (E).

Figure 25:
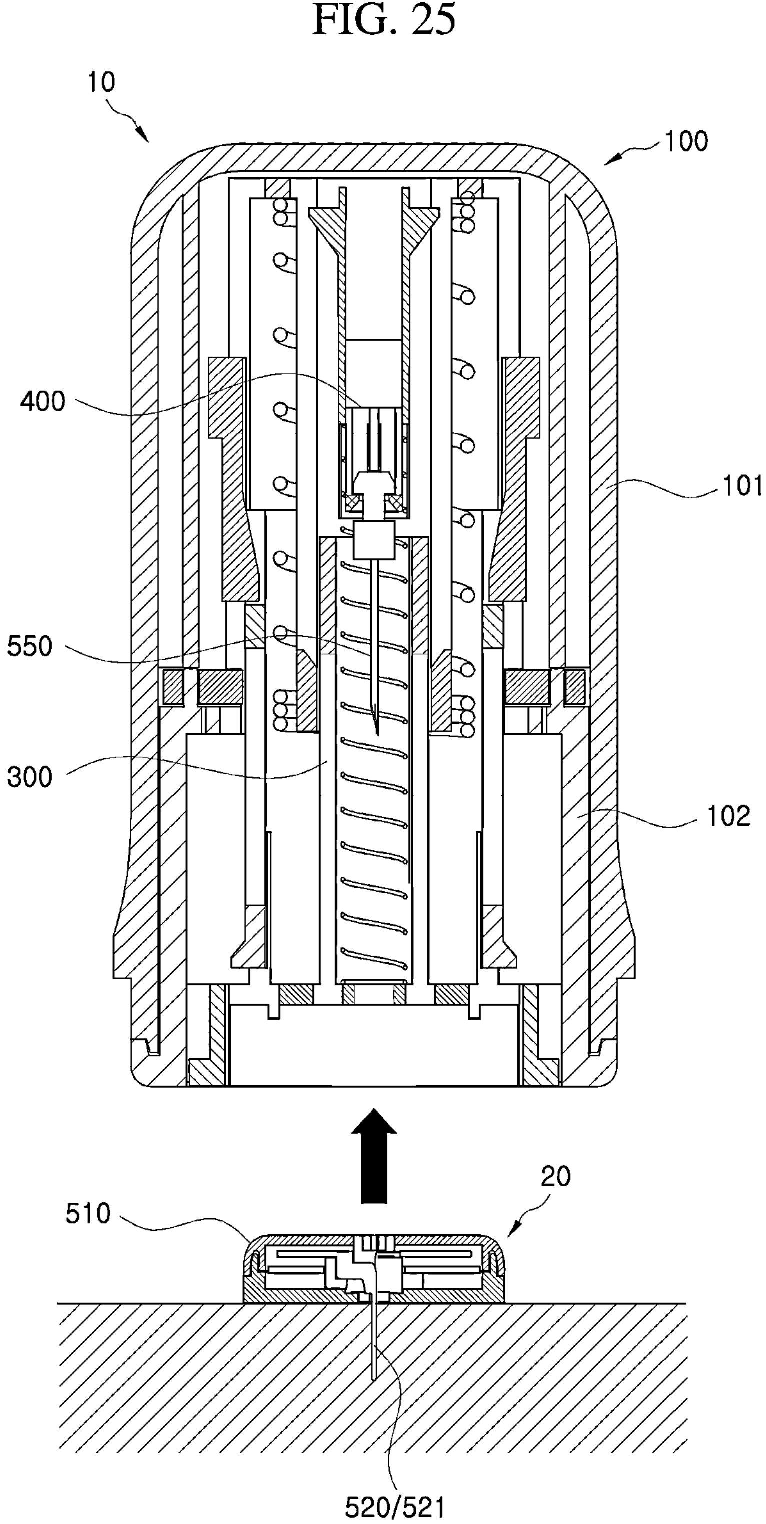

In this state, because the interlock between the sensor fixing hook (330) and the body attachable unit (20) is releasable as described above, the applicator (10) can be upwardly separated and removed as shown in FIG. 25, and if the applicator (10) is separated and removed in this way, only the body attachable unit remains in the state attached to the human body (E).

After that, the sensor unit (520) and the wireless communication chip (540) of the body attachable unit (20) can initiate operation by the operation of a pressurizing operation module (570) of the body attachable unit (20) and so on, and therefore the measurement result of the blood glucose by the body attachable unit (20) can be transmitted to a separate external terminal. According to an embodiment of the present disclosure, because both of the sensor unit (520) and the wireless communication chip (540) are installed to the body attachable unit (20), no additional work for connecting and coupling a separate transmitter is needed.

Next, details of the body attachable unit (20) will be described according to an embodiment of the present disclosure.

Figure 26:
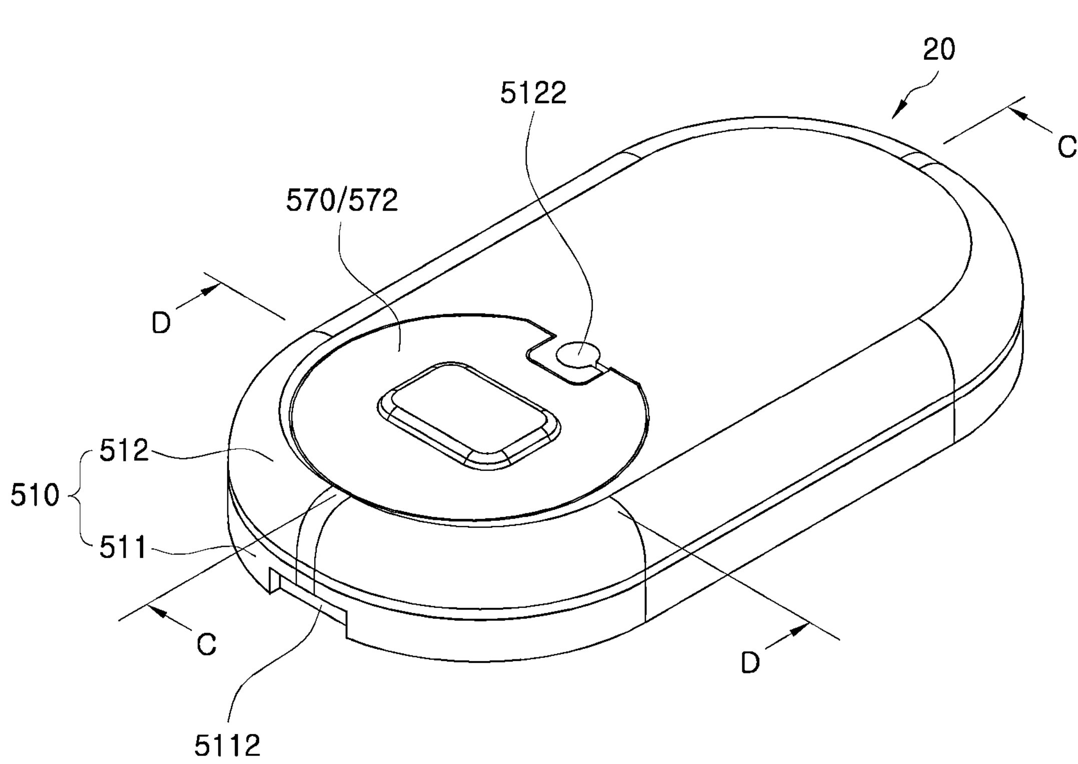
FIG. 26 is a perspective view conceptually illustrating an outer structure of a body attachable unit attached to a human body according to an embodiment of the present disclosure.
Figure 27:
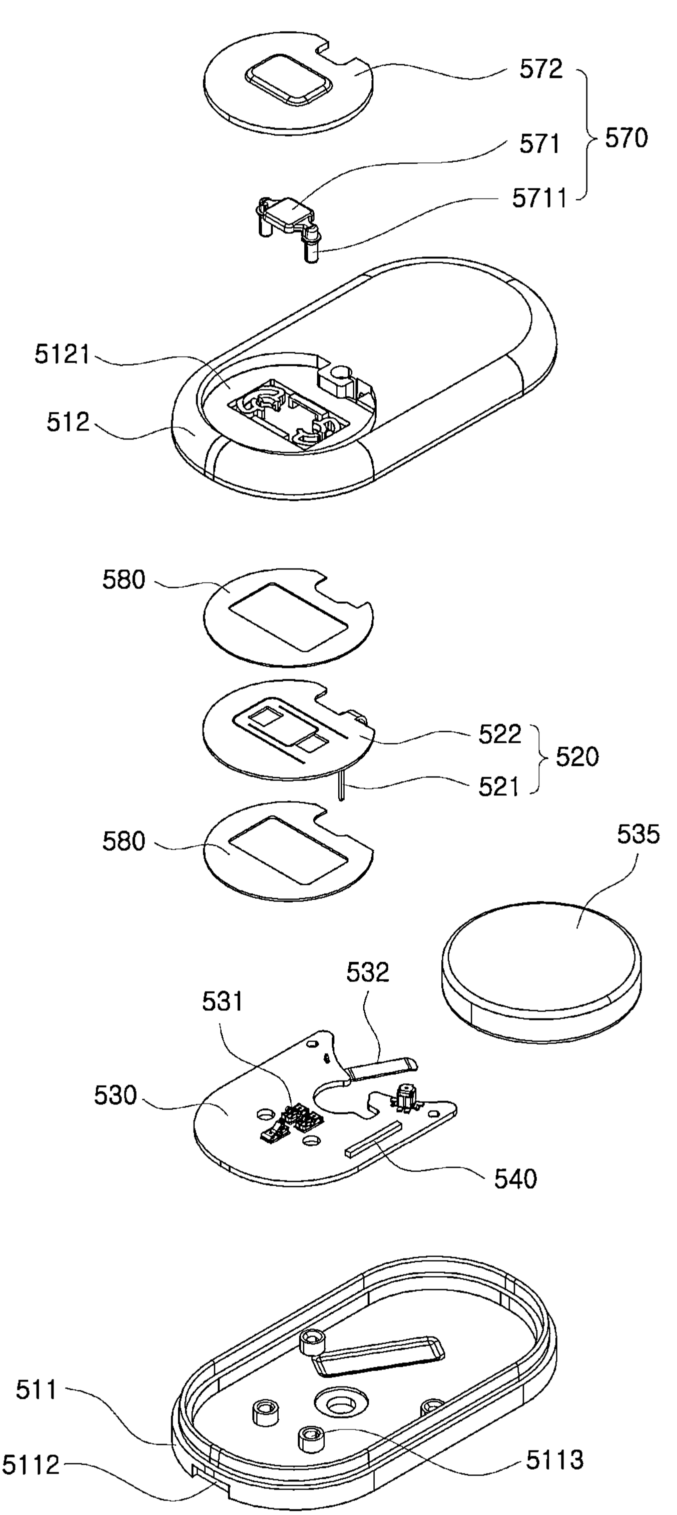
FIG. 27 is an exploded perspective view conceptually illustrating components of a body attachable unit.
Figure 28:
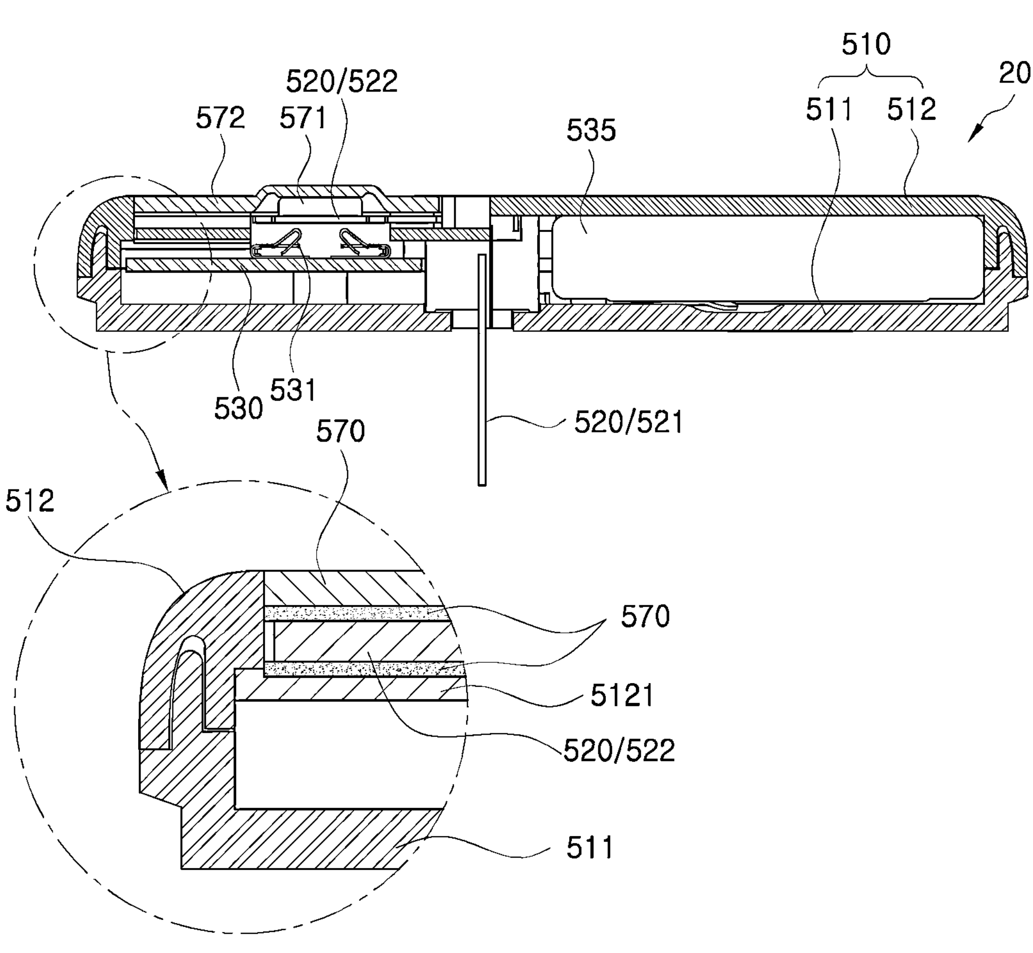
FIG. 28 is a cross-sectional view taken along line "C-C" of FIG. 26.
Figure 29:
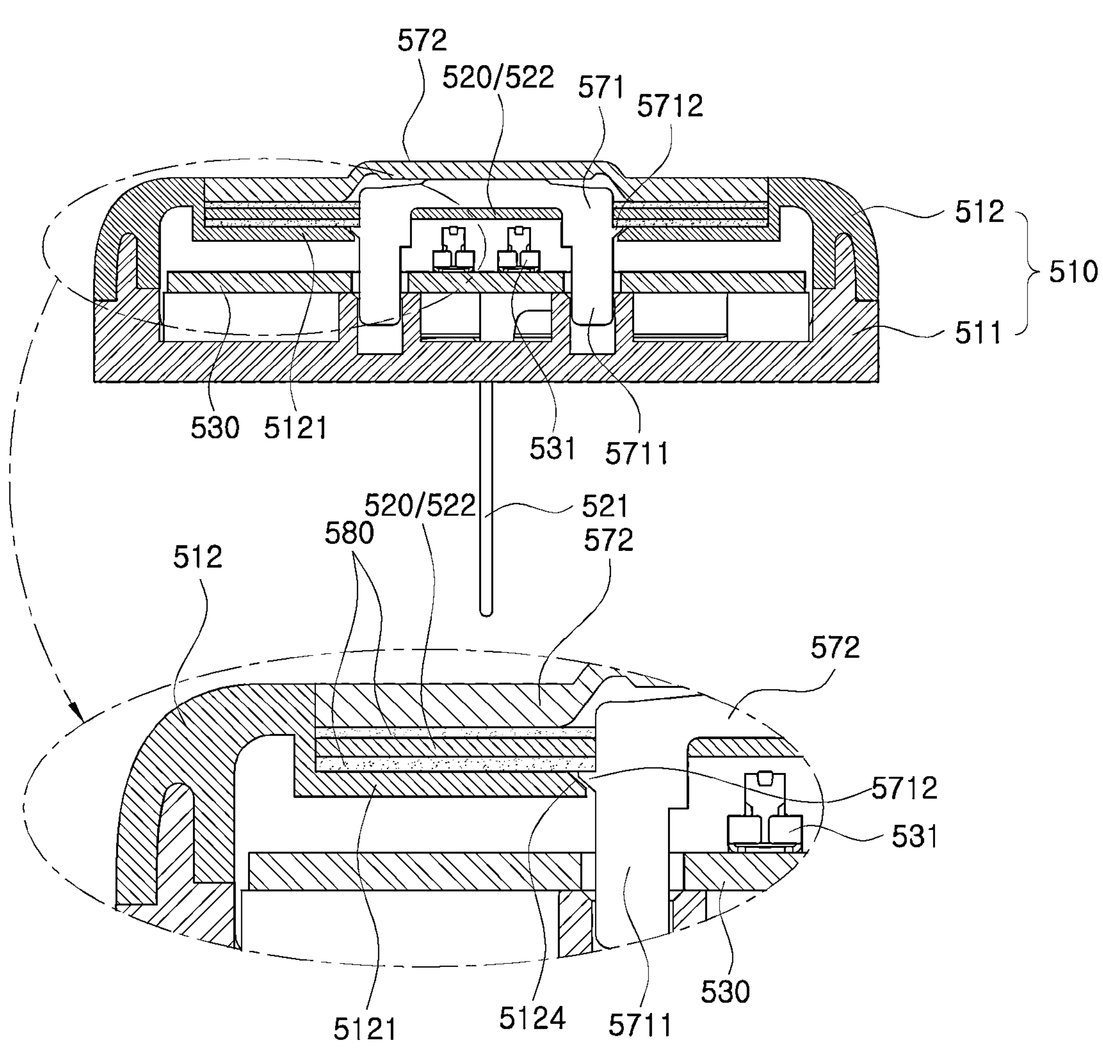
FIG. 29 is a cross-sectional view taken along line "D-D" of FIG. 26.
Figure 30:
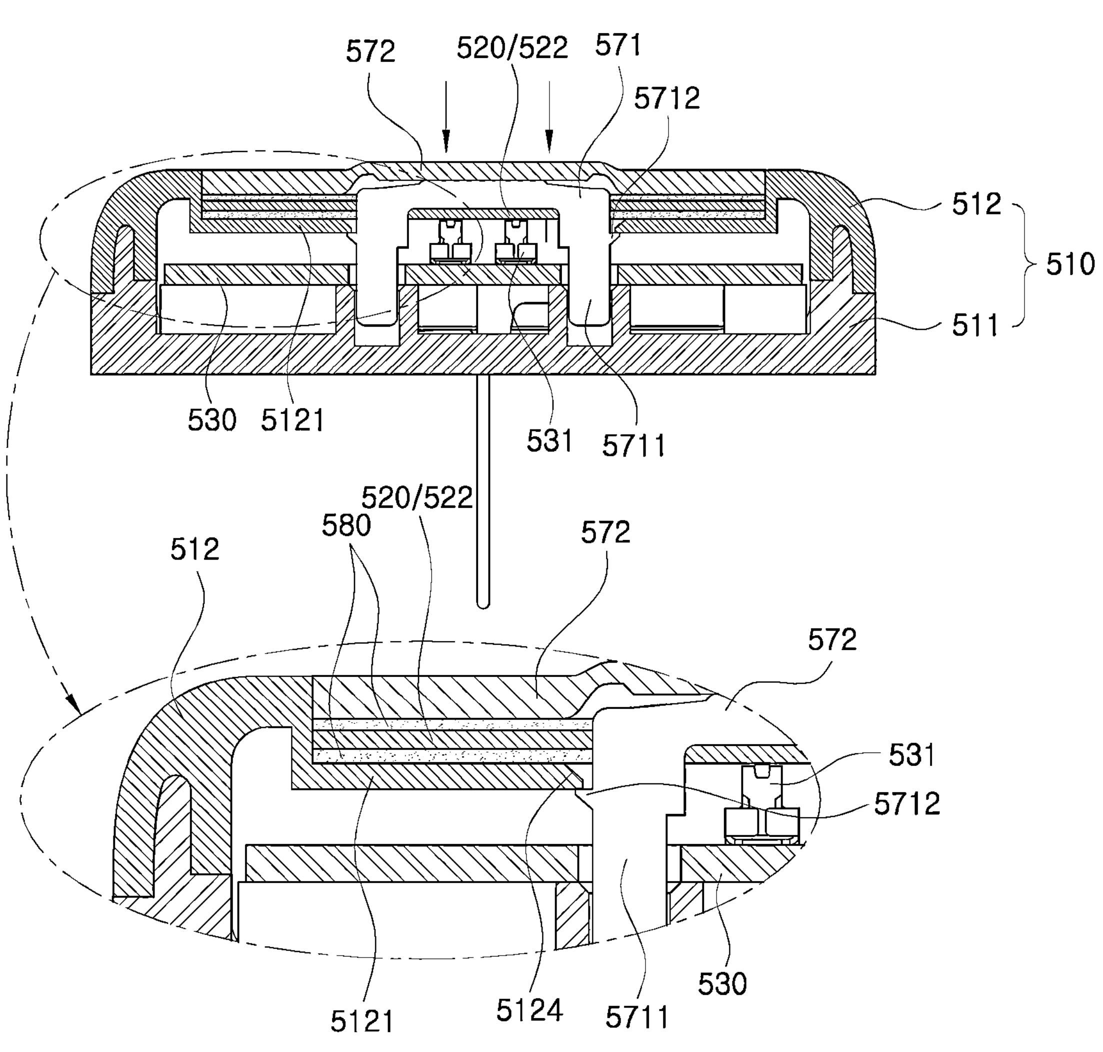
FIG. 30 is a conceptual view illustrating a operation state of a pressurizing operation module according to an embodiment of the present disclosure.

FIG. 26 is a perspective view conceptually illustrating an outer structure of a body attachable unit attached to a human body according to an embodiment of the present disclosure, FIG. 27 is an exploded perspective view conceptually illustrating components of a body attachable unit, FIG. 28 is a cross-sectional view taken along line "C-C" of FIG. 26, FIG. 29 is a cross-sectional view taken along line "D-D" of FIG. 26, and FIG. 30 is a conceptual view illustrating a operation state of a pressurizing operation module according to an embodiment of the present disclosure.

The body attachable unit (20) according to an embodiment of the present disclosure is configured to comprise the housing (510) to which the adhesive tape (560) is attached so that a bottom side of the housing (510) can be attached to skin, the sensor unit (520) disposed inside the housing (510) so that one end portion of the sensor unit (520) externally protrudes from the bottom side of the housing (10) and is inserted into the human body when the housing (510) is attached to the skin, and a PCB board (530) arranged inside the housing 510).

One end portion of the sensor unit (520) is formed to be inserted into the human body and the other end portion of the sensor unit (520) is formed to contact the PCB board (530), a sensor body unit (522) is formed at the other end of the sensor unit (520) to be contacted with an electrical contact point of the PCB board (530), and a sensor probe unit (521) is formed at the one end portion and the sensor probe unit (521) is formed to extend in the form of being bent from one side of the sensor body unit (522) and outwardly protrudes from the housing (510) and is inserted into the human body. The sensor body unit (522) is formed to have a structure with a relatively large area, and the sensor probe unit (521) is formed to have a relatively narrow and long structure.

The housing (510) may be formed to be divided into a upper housing (512) and a lower housing (511) to form an inner accommodating space, a sensor supporting unit (5121) supporting the sensor body unit (522) to be spaced apart from the electrical contact point (531) of the PCB board (530) at a certain distance is formed inside the housing (510), and a sensor guide unit (not shown) configured to support and guide a certain section of the sensor probe unit (521) is also formed inside the housing (510). Additionally, a board supporting unit (5113) for fixedly supporting the PCB board (530) at a certain location may be also formed inside the housing (510).

The electrical contact point (531) is formed at the PCB board (530) to be electrically connected with the sensor unit (520), and the wireless communication chip (540) is installed to the PCB board (530) to transmit the glucose measurement result measured by the sensor unit (520) to an external terminal. According to an embodiment of the present disclosure, by installing the wireless communication chip (540) at the inside of the body attachable unit (20), the communication with the external terminal can be easily performed without a work connecting a separate transmitter.

Further, a battery (535) configured to supply power to the PCB board (530) is installed at the inside of the housing (510), and the battery (535) is not installed at one side of the PCB board (530) but disposed at an area independent from the PCB board (530). Accordingly, the PCB board (530) and the battery (535) are independently arranged so that any area of the PCB board (530) and the battery (535) projecting into the bottom surface of the housing (530) cannot overlap each other. By arranging the PCB board (530) and the battery (535) to areas independent to each other, respectively, the thickness of the body attachable unit (20) may be reduced and the size of the body attachable unit (20) may be more minimized. In this embodiment, at the PCB board (530), a separate contact terminal (532) may be formed to extend to the battery (535) to be electrically contacted and connected to the battery (535).

The body attachable unit (20) according to an embodiment of the present disclosure is formed so that the other end portion of the sensor unit (520), i.e., the sensor body unit (522), is contacted to the electrical contact point (531) of the PCB board (530) by the manipulation or operation of the user, and according to this electrical contact, the operation of the body attachable unit (20) may be initiated. Accordingly, the embodiment of the present embodiment is configured to perform the power supply as well as the initiation of the operation of the sensor unit (520), the wireless communication chip (540) and other components by the electrical connection of the sensor unit (520) and the PCB board (530) by the manipulation of the user.

The housing (510) may have a separate pressurizing operation module (570) activated by the operation of the user to connect the other end portion of the sensor unit (520) and the electrical contact point (531) of the PCB board (530) by the operation of the user.

The pressurizing operation module (570) is movably connected to the housing (510) and may comprise a movable pressurizing body (571) configured to be movable in a pressurizing direction by the pressure applied by the user, and according to the movement of the movable pressurizing body (571) at least a partial area of the other end portion of the sensor unit (520) is transformed by the pressure of the movable pressurizing body (571) and contacted to the electrical contact point (531) of the PCB board (530).

Additionally, the pressurizing operation module (570) may further comprises a button cover (572) having flexible material and a structure covering an outer surface of the movable pressurizing body (571) and coupled to the housing (510) so that the button cover (572) can be exposed to the outside of the body attachable unit (20) in order to be capable of the pressurizing operation by the user, and the coupling portion between the button cover (572) and the housing (510) may be processed to be sealed.

In this embodiment, the seal processing means at the coupling portion between the button cover (572) and the housing (510) may be configured to use a double-side tape (580). For example, one side of the double-side tape (580) is adhered to the other portion of the sensor unit (520), such as one side of the sensor body unit (522), along its circumferential edge, the other side of the double-side tape (580) is adhered to the inner-side surface of the button cover (572) along its circumferential edge, and this double-side tape (580) can seal the circumferential edge of the button cover (572). In this embodiment, the double-side tape (580) may be adhered to the other side of the sensor body unit (522) along the circumferential edge as well, and by this, the sensor body unit (522) may be adhered and fixed to the sensor supporting unit (5121) along the circumferential edge of the sensor body unit (522) by using the double-side tape (580).

In a state that the circumferential edge of the sensor body (522) is adhered and fixed to the sensor supporting unit (5121) by the double-side tape (580), the center section of the sensor body unit (522) is transformed by the pressure of the movable pressurizing body (571) and may contact the electrical contact point of the PCB board (530) as illustrated in FIG. 30. Although the movable pressurizing body (571) is moved in the pressurized direction, because the button cover (572) is made of flexible material and the circumferential edge portion of the button cover (572) is adhered to the housing (510) by the double-side tape (580), only the center portion of the button cover (572) is transformed in the pressurized direction and the circumferential edge portion of the button cover (572) is adheredly fixed and remains the sealed state.

Meanwhile, it is preferred that after the sensor body unit (522) is contacted to the electrical contact point (531) of the PCB board (530) by the operation of the user the contact status can be stably maintained for stable measurement of blood glucose, and for this, the movable pressurizing body (571) is formed to be fixedly positioned in a state that the movable pressurizing body (571) is moved in a pressurized direction by the urging force.

Figure 31:
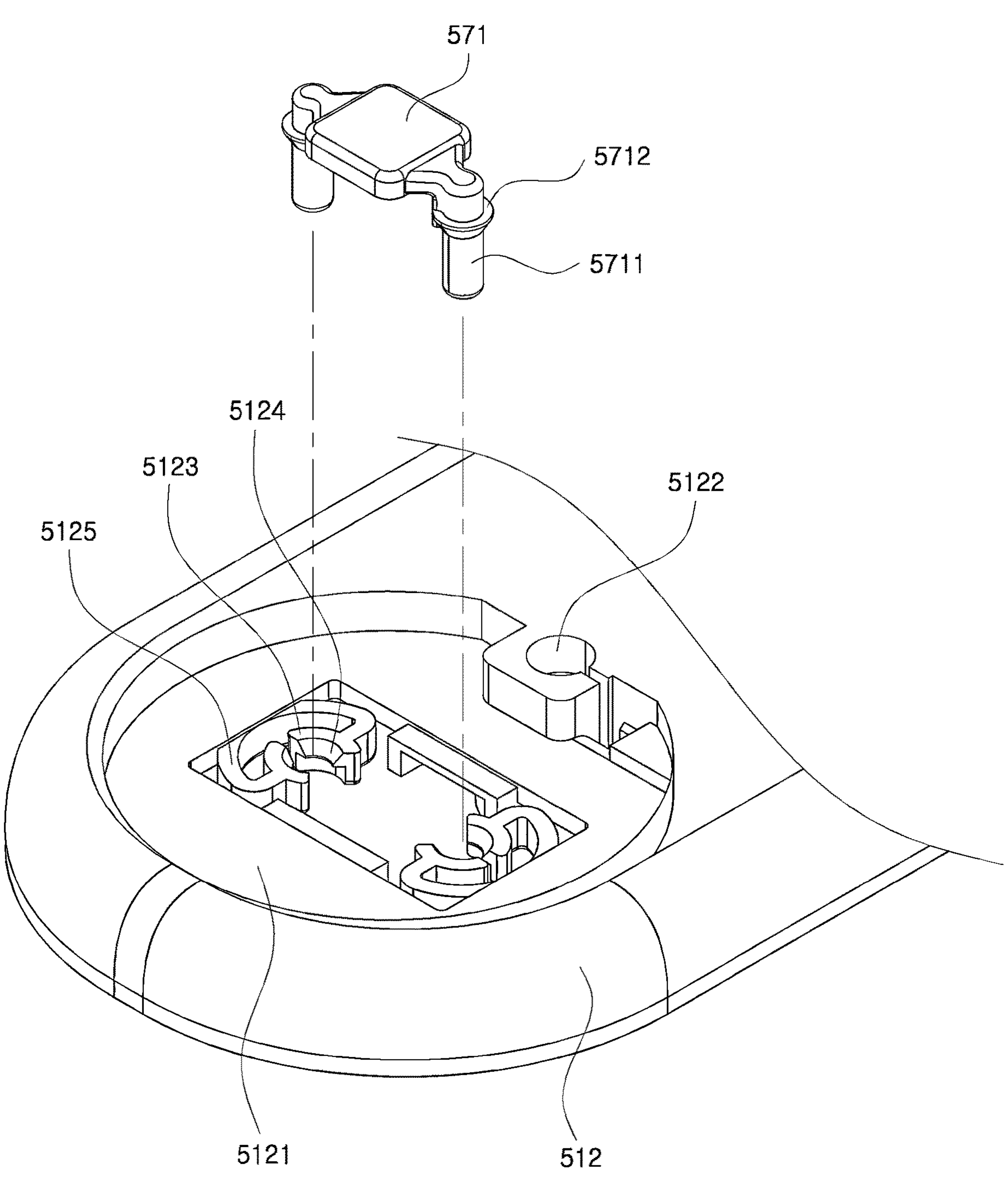
FIG. 31 is a perspective view of schematically illustrating detailed configuration of a pressurizing operation module according to an embodiment of the present disclosure.

For fixing the position of the movable pressurizing body (571), a protruding guide unit (5711) protruding along a movement direction of the movable pressurizing body (571) is formed at the movable pressurizing body (571) as illustrated in FIG. 31, and a locking hook (5712) may be formed at the outer circumferential surface of the protruding guide (5711). Additionally, an interlocking projection (5124) to which the locking hook (5712) of the protruding guide unit (5711) in a state that the movable pressurizing body (571) is moved in the pressurized direction may be formed at the housing (510). The position of the movable pressurizing body (571) may be fixed as the locking hook (5712) is interlockedly coupled to the interlocking projection (5124) as shown in FIG. 30.

In this embodiment, the interlocking projection (5124) may be formed at the sensor supporting unit (5121) of the housing (510), at least two guide fixing units (5123) separated to each other, formed along a circumferential direction and having a structure covering the protruding guide unit (5711) of the movable pressurizing body (571) are formed at the sensor supporting unit (5121) of the housing (510) as illustrated in FIG. 31, and the interlocking protrusion (5124) may be formed at each guide fixing unit (5123). Additionally, each guide fixing unit (5123) may be arranged in a structure being elastically supported by the elastic supporting unit (5125) which is configured to be elastically transformable.

Accordingly, during the process that the movable pressurizing body (571) is moved toward the pressurized direction the guide fixing unit (5123) is elastically transformed and makes the movement of the movable pressurizing body (571) smooth, after the movement of the movable pressuring body (571) is completed, the guide fixing unit (5123) is elastically returned and the locking hook (5712) is interlockedly coupled to the interlocking projection (5124), and because the guide fixing unit (5123) is elastically supported by the elastic supporting unit (5125), the interlocking coupling state between the locking hook (5712) and the interlocking projection (5124) is stably maintained.

Meanwhile, the sensor unit (520) may consist of the sensor body unit (522) and the sensor probe unit (521) as described above, and a pressure transforming unit (523) configured to be transformed by the pressurizing movement of the movable pressurizing body (571) and contacted to the electric contact point (531) of the PCB board (530) may be formed at the sensor body unit (522).

Figure 32:
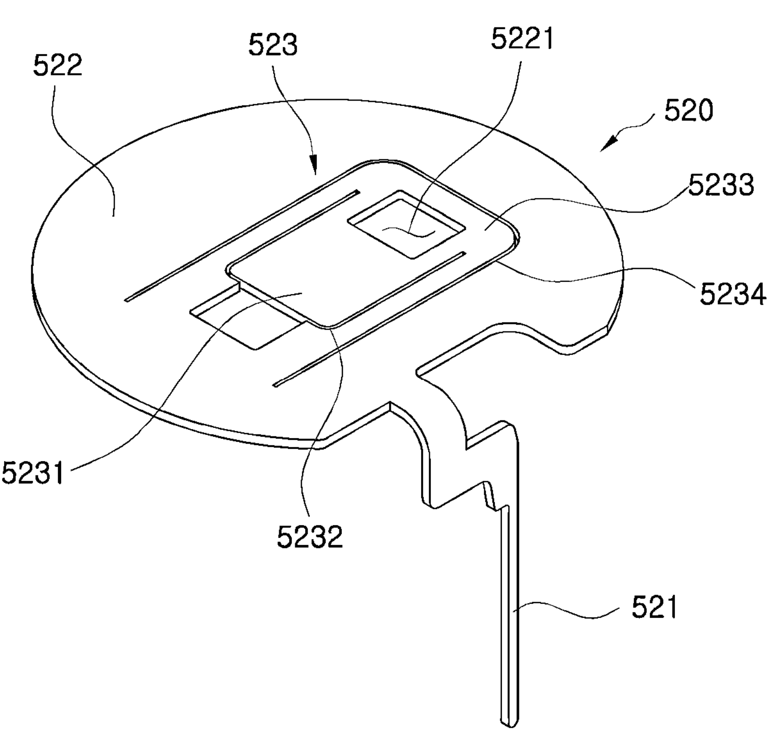
FIG. 32 is a perspective view of schematically illustrating detailed configuration of a sensor unit according to an embodiment of the present disclosure.

The pressure transforming unit (523) comprise a first cut area (5231) having a structure cut along a first cut line (5232) formed at the center section of the sensor body unit (522) as illustrated in FIG. 32, and the first cut area (5231) may be formed to be transformable by the pressure applied by the movable pressurizing body (571).

Additionally, the pressure transforming unit (523) further comprise a second cut section (5233) positioned at the center section of the sensor body unit (522) and having a structure cut along a second cut line (5234) formed at the outer section of the first cut line (5232), and the first cut area (5231) and the second cut area (5233) may be formed to be transformable by the pressure applied by the movable pressurizing body (571).

In this embodiment, the first cut line (5232) is formed as an partially opened structure in a closed loop, and the second cut line (5234) is formed to have an opened section at the position opposing to the opened section of the first cut line (5232) and formed in a closed-loop structure surrounding the opened section of the first cut line (5232).

Figure 33:
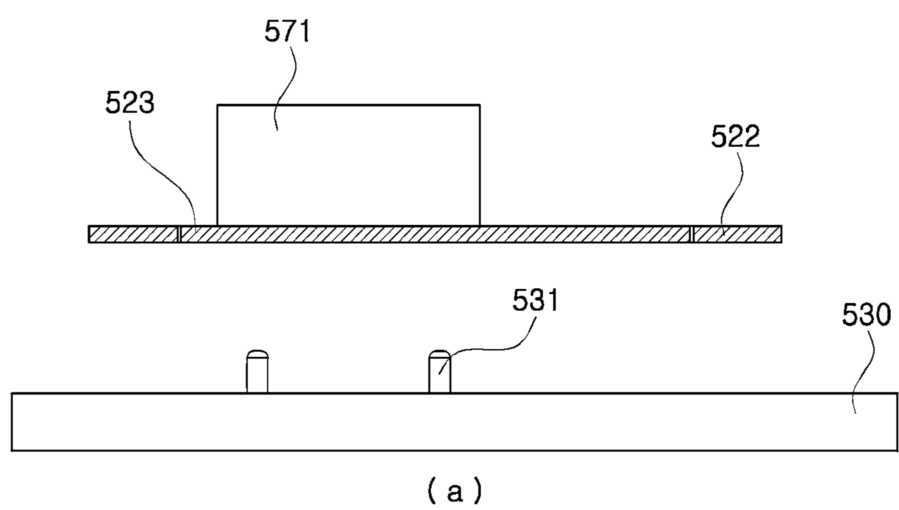
FIG. 33 is a view of conceptually illustrating a pressurizing operation state of a sensor unit according to an embodiment of the present disclosure.
Figure 33:
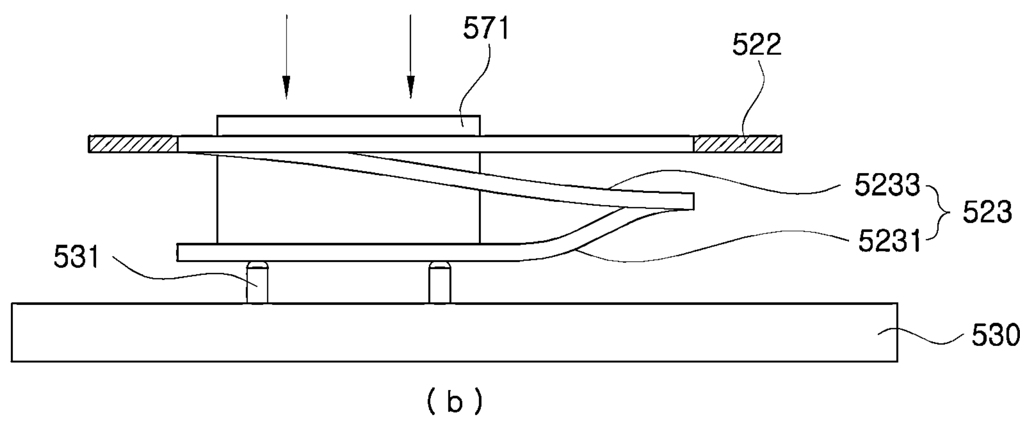

If the movable pressurizing body (571) is operated by the pressure according to the structure described above, a first cut section (5231) of the pressure transforming unit (523) is downwardly elastically transformed as illustrated in FIGS. 33 (*a*) and (*b*), then a second cut section (5233) formed at an outer section of the first cut are (5231) is downwardly elastically transformed sequentially, and therefore because the first cut section (5231) directly contacting the electric contact point (531) of the PCB board (530) contact the electric contact point (531) of the PCB board (530) in a relatively horizontal state, the contacting state to the electric contact point (531) of the sensor body unit (522) can be more stably maintained.

Meanwhile, at the PCB board (530), a plurality of electric contact points (531) electrically contacting the sensor body unit (522) may protrude toward the sensor body unit (522), and the protruding height of at least one of the plurality of electric contact points (531) may be higher than the rest.

Figure 34:
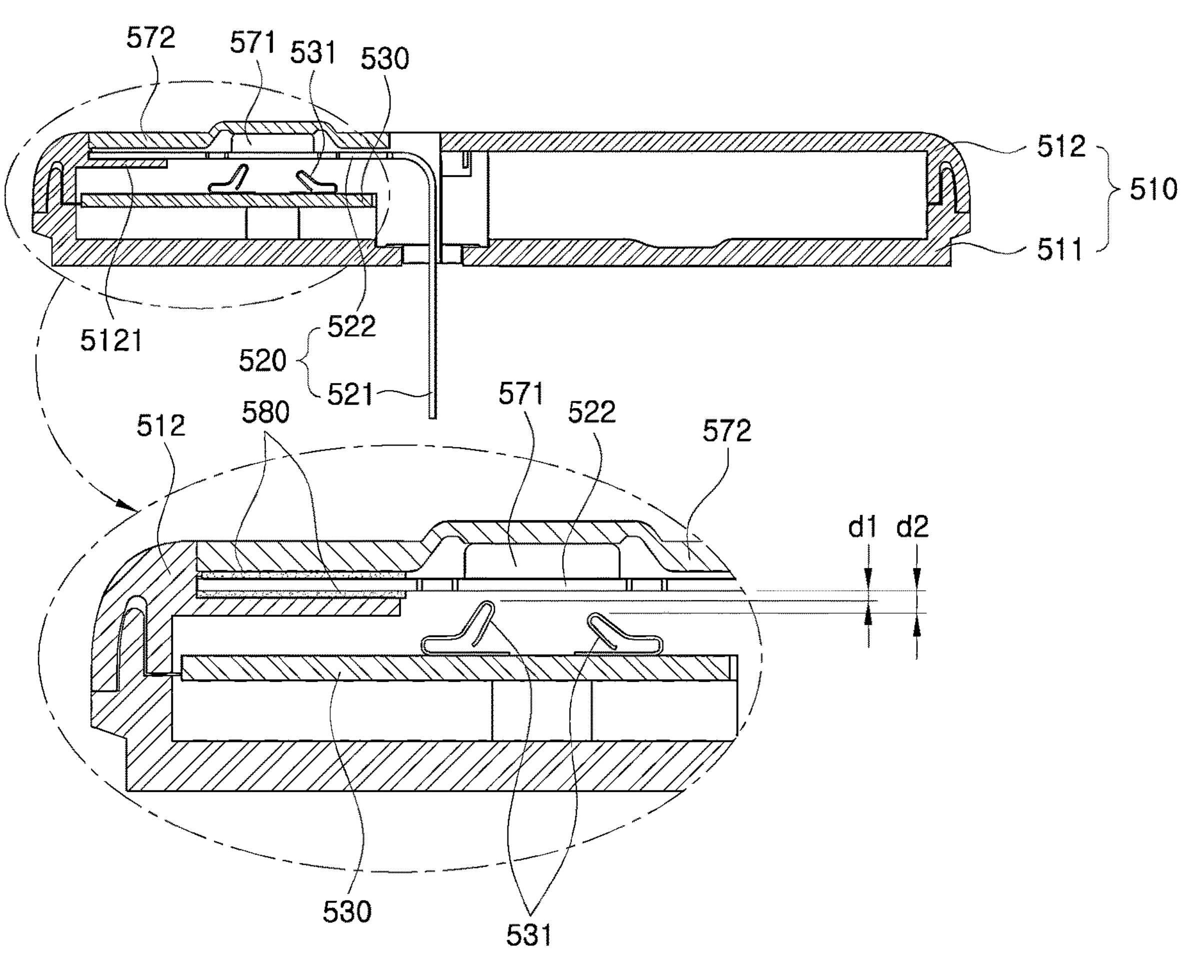
FIG. 34 is a view of conceptually illustrating arrangement relation between a sensor unit and an electrical contact point according to an embodiment of the present disclosure.

For example, when two electric contact points (531) are formed on the PCB board (530) as illustrated in FIG. 34, the protruding height of one of the electric contact points (531) is formed be higher than the other of the electric contact points (531), and therefore clearance distances d1, d2 are formed differently from each other.

By this arrangement structure, the contact of the sensor body unit (522) to the electric contact point (531) even without the pressure operation of the user due to the manufacture and assembly tolerance may be prevented.

Specifically, according to an embodiment of the present disclosure, in the housing (510), the sensor body unit (522) of the senor unit (520) and the electric contact point (531) of the PCB board are disposed to be separated from each other, but can contact each other by the pressure operation of the user. However, because the housing (531) may be formed in a very thin structure, it may be difficult of stably maintaining the separation state between the sensor body unit (522) and the electric contact point (531) in the housing (510). Specially, the sensor body unit (522) and the electric contact point (531) may be manufactured and distributed to customers in a state that the sensor body unit (522) and the electric contact point (531) contact each other by the manufacture and assembly tolerance and other reasons before the pressure operation of the user.

If the protruding height of at least one of the plurality of electric contact points (531) is higher that the rest of the electric contact points (531) as described above, only the electric contact point (531) having the highest protruding height may contact the sensor body unit (522) and the other electric contact points (531) may maintain a separation state from the sensor body nit (522). This is because the highest protruding contact point (531) can perform the function of upwardly supporting the sensor body unit (522). In this embodiment, the plurality of electric contact points (531) may be configured to elastically transformable and be formed to elastically protruding from the PCB board (530), and such an elastic force may perform the desired function of support and contact associated with the sensor body unit (522).

Even if the sensor body unit (522) and at least one of the electric contact points (531) contact each other but only one of the electric contact points (531) contacts the sensor body unit (522), the operation of the body attachable unit (20) is not initiated. Accordingly, the operation of the sensor unit (520), the wireless communication chip (540), and other components is not initiated, and the power supply by the battery (535) may not be initiated.

This operation initiation prevention function can result from simple means for setting the circuit pattern of the PCB board (530) to be activated only when all of the plurality of the electric contact points (531) contact the sensor body unit (522).

When the plurality of electric contact points (531) have different protruding heights from each other, the pressurizing operation module (570) may need to be formed so that the movement distance of the movable pressurizing body (571) can be greater than the separation distance between the lowest protruding electric contact point (531) among the plurality of the electric contact points (531) and the sensor body unit (522).

Although embodiments of configuration of the pressurizing operation module (570) operated by the pressure type with respect to the structure of contacting the sensor body unit (522) and the electric contact point (531) by the user's operation are described above, various types in addition to the pressure type may be implemented, and some exemplary configurations are described as follows.

Figure 35:
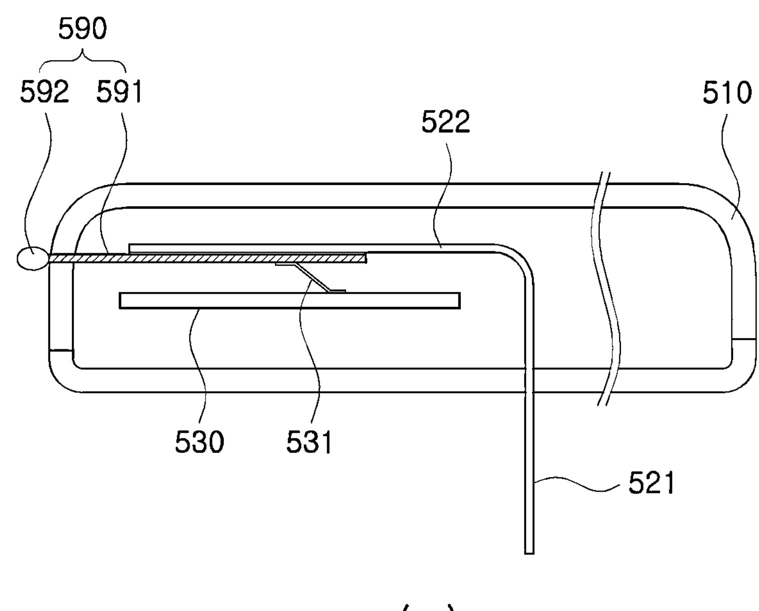
FIGS. 35 to 37 are views of conceptually illustrating various configurations of electrical contact points according to embodiments of the present disclosure.
Figure 35:
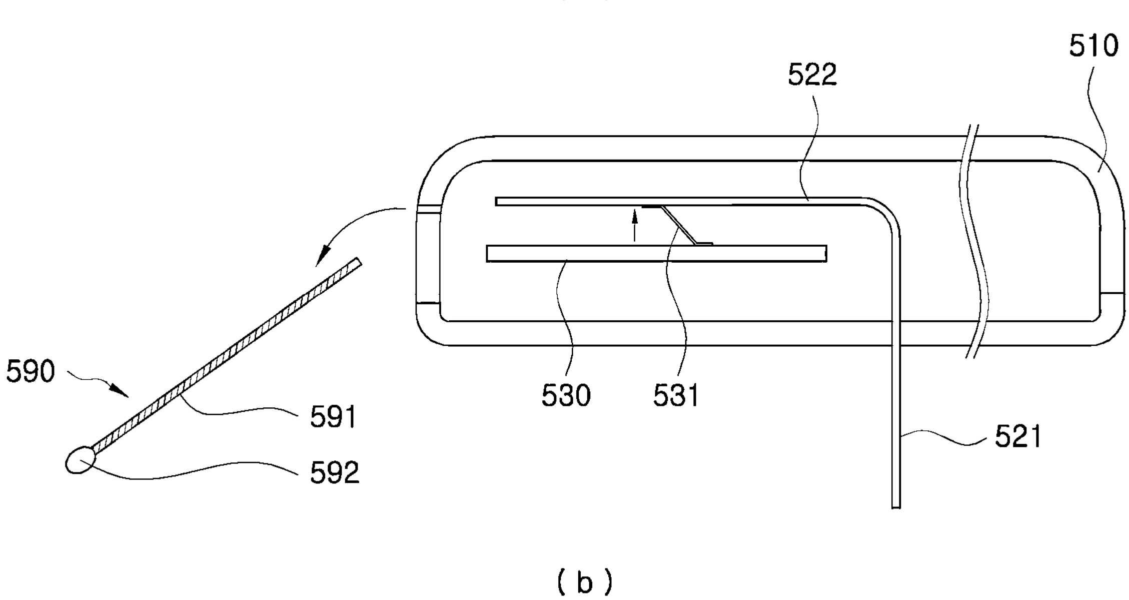
Figure 36:
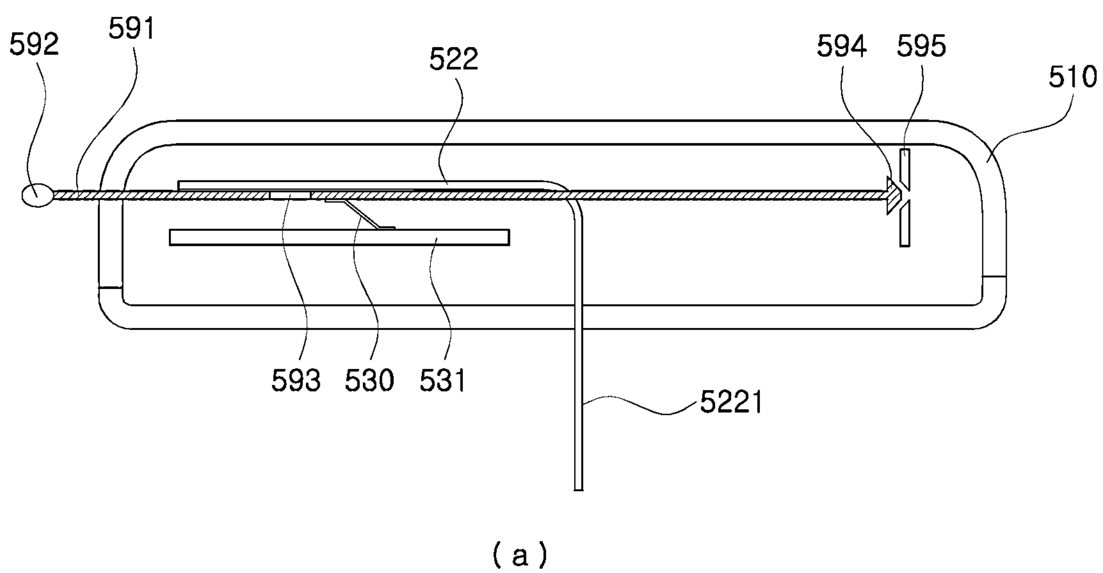
Figure 36:
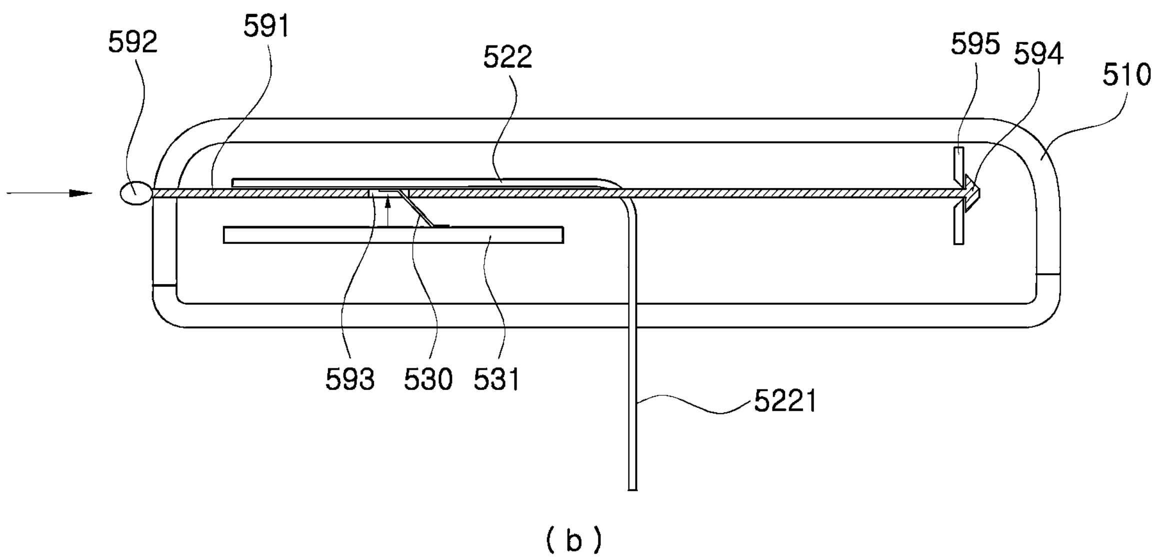
Figure 37:
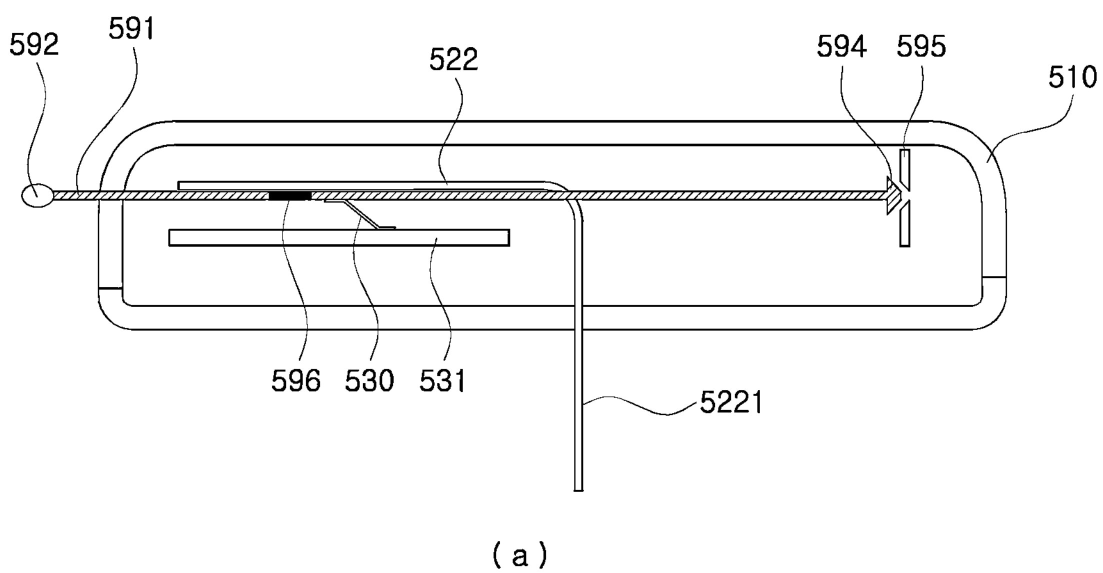
Figure 37:
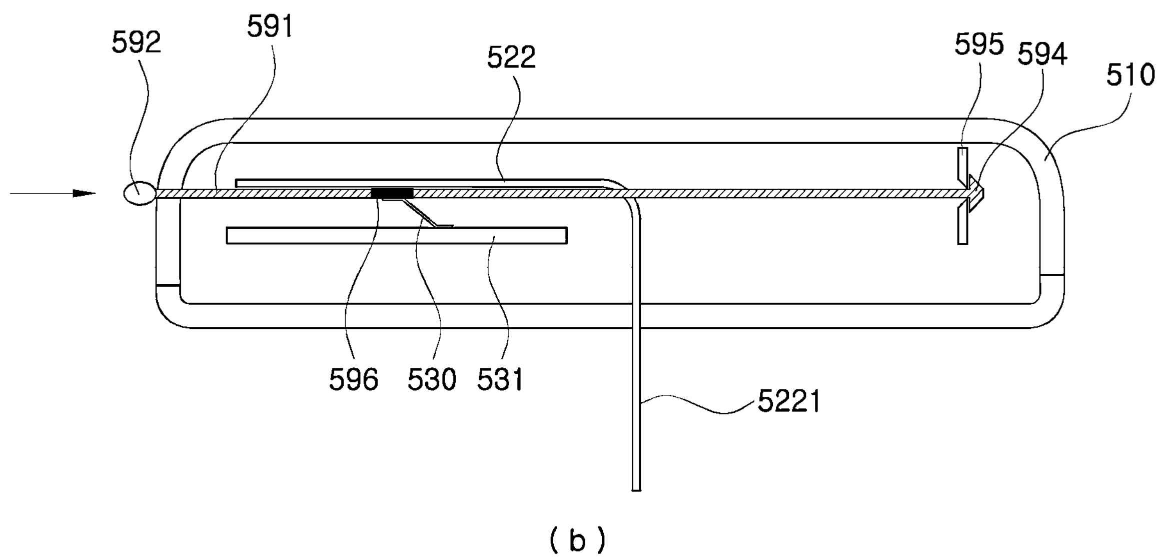

FIGS. 35 to 37 are conceptual views of various configuration of a contact point connection module according to embodiments of the present disclosure.

A contact point connection module (590) which is operated by the manipulation of the user so that the sensor body unit (522) and the electric contact point (531) of the PCB board (530) contact each other is illustrated in FIGS. 35 to 37, and this contact point connection module (590) may be configured to operate in a type that in a state that the contact point connection module (590) is positioned between the sensor body unit (522) and the electric contact point (531) of the PCB board (530) to block their contact the contact point connection module (590) may be moved by the operation of the user to release from blocking the contact between the sensor body unit (522) and the electric contact point (531) of the PCB board (530).

Specifically, the electric contact point (531) of the PCB board (530) is formed to elastically protrude in a direction that the electric contact point (531) can contact the sensor body unit (522), and as the contact point connection module (590) releases from blocking the contact between the sensor body unit (522) and the electric contact point (531) of the PCB board (530), the electric contact point (531) of the PCB board (530) is configured to be elastically moved by the elastic force and be contacted to the other end portion of the sensor unit (520).

In this embodiment, the contact point connection module (590) may be configured to comprise a movable plate (591) disposed between the sensor body unit (522) and the electric contact point (531) of the PCB board (530) and installed to be movable according to the operation of the user inside the housing as illustrated in FIG. 35.

As shown in FIG. 35(*a*), in the assembled state that the movable plate (591) is inserted into the inside of the housing (510), the movable plate (591) is positioned between the sensor body unit (522) and the electric contact point (531) to block the contact between the sensor body unit (522) and the electric contact point (531), and as illustrated in FIG. 35(*b*), if the movable plate (591) is moved in a direction of being extracted and removed from the housing (510) by the operation of the user, the electric contact point (531) is upwardly moved by the elastic force and contacted to the sensor body unit (522).

Meanwhile, as illustrated in FIG. 36, the movable plate (591) is installed to be movable from the first location to the second location by the operation of the user, and a penetrating hole (593) may be formed at one side of the movable plate (591) and the penetrating hole (593) is configured to pressurize the electric contact point (531) toward the PCB board (530) at the first location and release the pressurized state of the electric contact point (531) at the second location.

Accordingly, as shown in FIG. 36(*a*), in a state that the movable plate (591) is positioned at the first location inside the housing (510), the contact between the sensor body unit (522) and the electric contact point (531) is blocked by the movable plate (591), and as illustrated in FIG. 36(*b*), if the movable plate (591) is moved to the second location in the housing (510), the electric contact point (531) is elastically moved, penetrates the penetrating hole (593), and contact the sensor body unit (522) because the penetrating hole (593) of the movable plate (591) is positioned between the electric contact point (531) and the sensor body unit (510).

In this embodiment, a stopper unit (592) formed to limit a movable range of the movable plate (591) to between the first location and the second location may be formed at the movable plate (591).

Meanwhile, the movable plate (591) may be configured to be unable to return to the first location again so that the position of the movable plate (591) is fixed in a state that it is moved to the second location.

For example, a locking hook (594) is formed at one end portion of the movable plate (591), an interlocking projection (595) configured to be interlocked with the locking hook (594) in a state that the movable plate (591) is moved to the second location is formed in the housing (510), and as the locking hook (594) is interlockedly coupled to the interlocking projection (595), the position of the movable plate (591) is fixed to the second location.

Further, as illustrated in FIG. 37, a contact point connection unit (596) made of conductive material may be additionally installed to the movable plate (591). This may be configured in a structure that the contact point connection unit (596) is installed to a portion where the penetrating hole (593) of the movable plate (591) is formed, and the electric contact point (531) and the sensor body unit (522) are electrically connected and contacted to each other by the contact point connection unit (596) when the movable plate (591) is moved.

Figure 38:
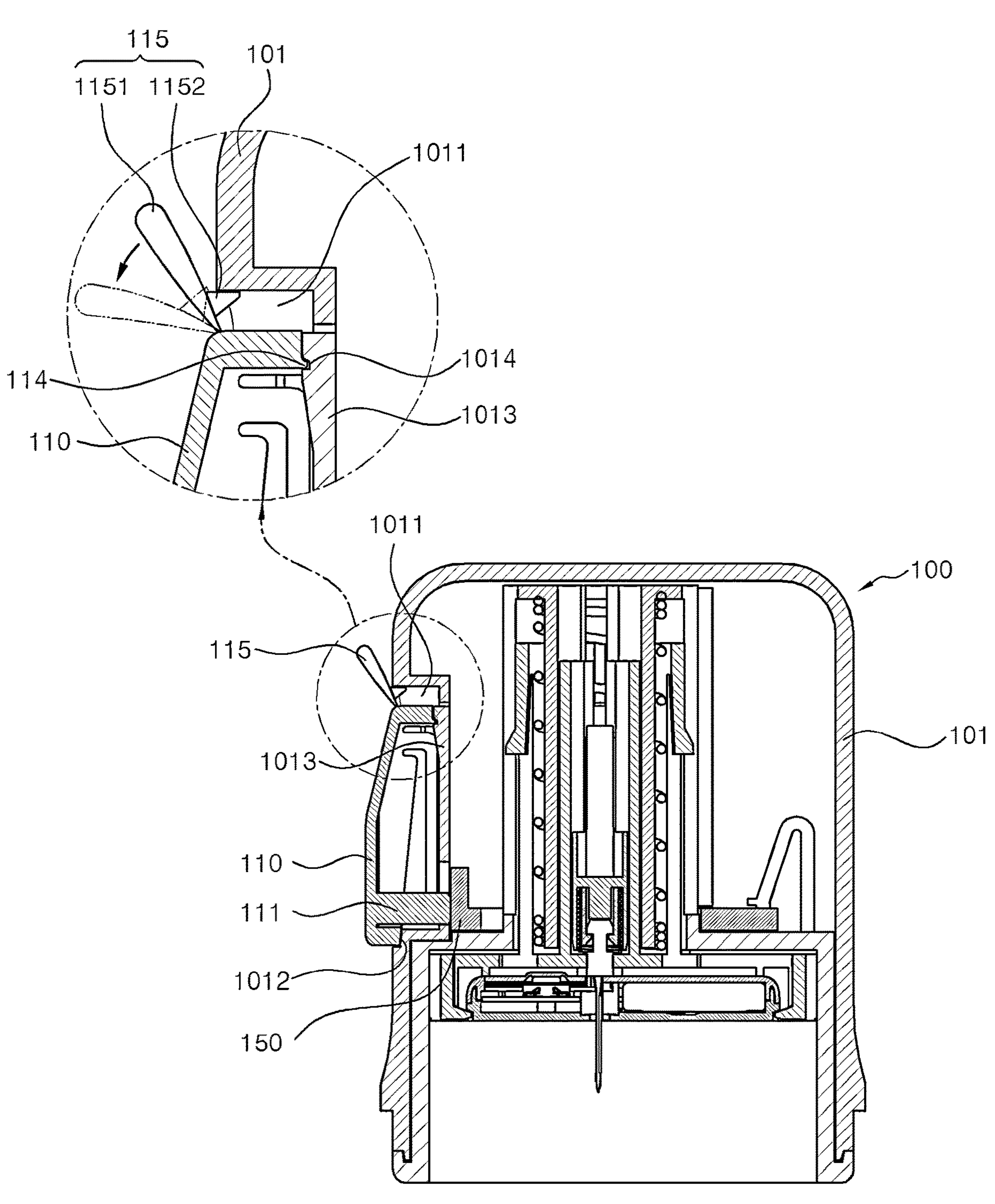
FIGS. 38 and 39 are views schematically illustrating a structure of a mode change locking unit of a pressure button according to an embodiment of the present disclosure.
Figure 39:
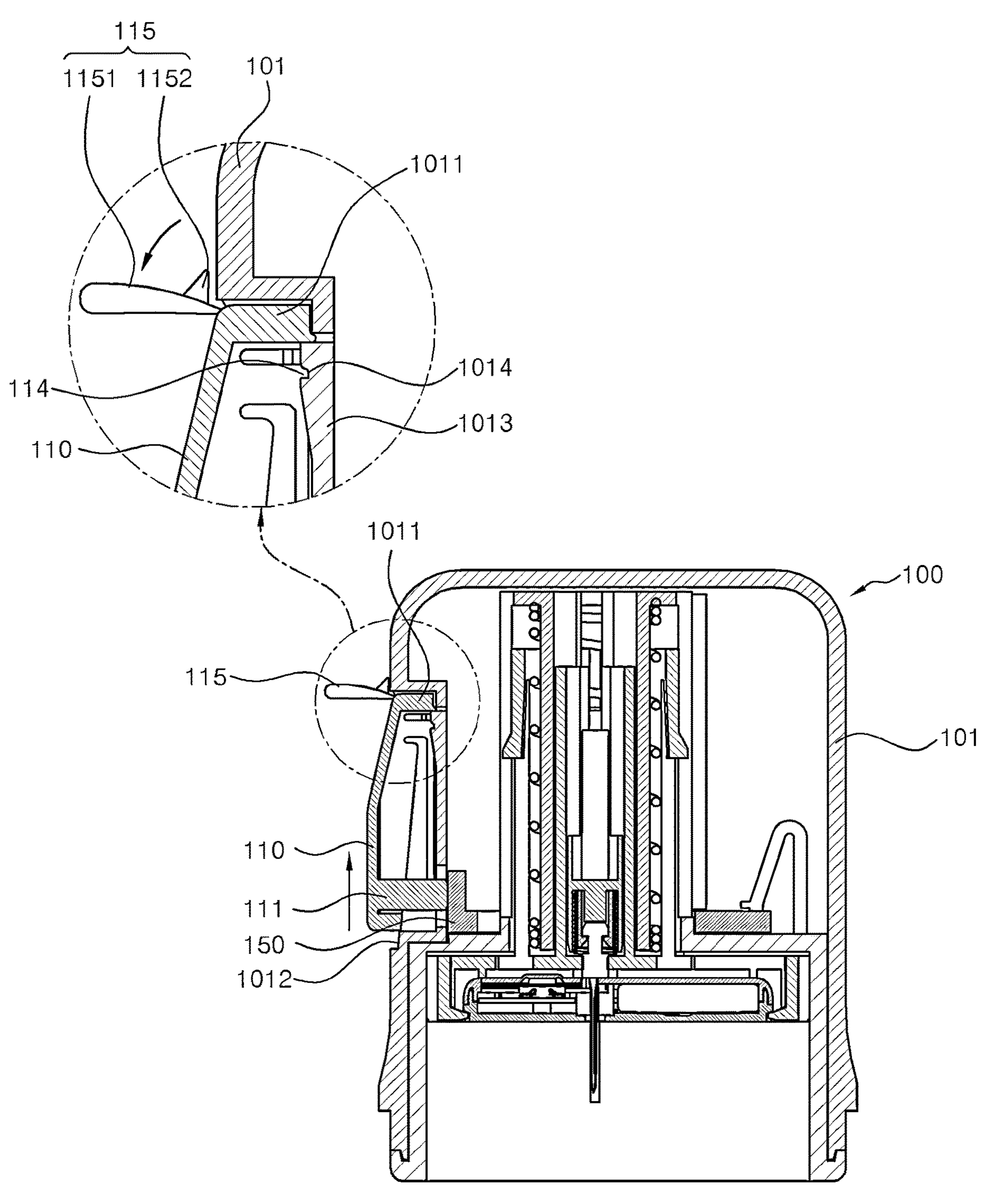

FIGS. 38 and 39 are views schematically illustrating a structure of a mode change locking unit of a pressure button according to an embodiment of the present disclosure.

The pressure button (110) according to an embodiment of the present disclosure may be configured to be mode-changeable between a safe mode preventing a pressurizing movement of a pressurizing manipulation and a pressurizing standby mode capable of performing the pressurizing movement according to the pressurizing manipulation as described above.

In this embodiment, the pressure button (110) comprises a locking unit (115) configured to block a mode change state of the pressure button (110) and release the block of the mode change state of the pressure button (110).

The locking unit (115) is configured to maintain the blocking of changing a mode state of the pressure button (110) to the pressurizing standby mode in the safe mode and be released from the blocking by the manipulation of the user.

The pressure button (110) is slidably movably installed to a button guide groove (1011) of the main case (100), and the status of the mode of the pressure button (110) is changed between the safe mode and the pressuring standby mode according to the sliding movement of the pressure button (110). Accordingly, the pressure button (110) maintains the safety mode in the button guide groove (1011), but the mode of the pressure button (110) may be changed to the pressurizing standby mode by the sliding movement caused by the manipulation of the user.

In this embodiment, the locking unit (115) is configured to block the mode change of the pressure button (110) in a way of limiting the sliding movement of the pressure button (110). For example, one end of the locking unit (115) is coupled to the pressure button (110) and the other end of the locking unit (115) is interlocked with the button guide groove (1011) to limit the sliding the movement of the pressure button (110).

More specifically, the locking unit (115) may be configured to comprise a locking main body (1151) of which one end is coupled to the pressure button (110) to be operated by the user as illustrated in FIG. 38, and a locking hook (1152) formed to protrude at one side of the locking main body (1151) to be interlocked with the inner circumferential surface of the button guide groove (1011).

In this embodiment, the locking main body (1151) is rotatably coupled to the pressure button (110), and the locking main body (1151) is configured to be releases from the interlock with the button guide groove (1011) of a locking hook (1152) by the user's manipulation of rotating the locking main body (1151). Although the rotatably movable structure of the locking main body (1151) consists of using a hinge and the like, the rotatably movable structure of the locking main body (1151) may be configured to be easily rotatable by the user by using a coupling unit with soft material as illustrated in FIGS. 38 and 39.

Additionally, the locking main body (1151) is formed to be elastically transformable, the locking main body (1151) is configured to be released from the interlock with the button guide groove (1011) of the locking hook (1152) as the user rotates the locking main body (1151) to be elastically transformed, the locking main body (1151) is coupled to the pressure button (110) while the locking main body (1151) is separatable and removable from the pressure button (110), and the locking main body (1151) may be configured to be released from the interlock with the button guide groove (1011) of the locking hook (1152) as the user separates and removes the locking main body (1151).

According to the embodiment, in the operation that the mode of the pressure button (110) is changed from the safe mode to the pressurizing standby mode, the mode change is performed through the separate locking unit (115), and therefore the user can more pay attention during the user's operation of the mode change and the operation of the applicator resulting from a malfunction or indeliberate behavior can be prevented.

Additionally, the locking unit (115) is formed so that the user can visually identify the mode change of operation states including a state blocking the mode change of the pressure button (110) and a state releasing from the blocking of the mode change of the pressure button (110), and as described above, if the locking body (1151) of the locking unit (115) is formed to extend to protrude from one side of the pressure button (110) and is configured in a way of being operated by rotation manipulation, the user can easily identify the locking unit (115), the operation state of the locking unit (115), i.e. whether the mode change is blocked or the blocking of the mode change is released, can be easily figured out so that safer use can be induced.

Figure 40:
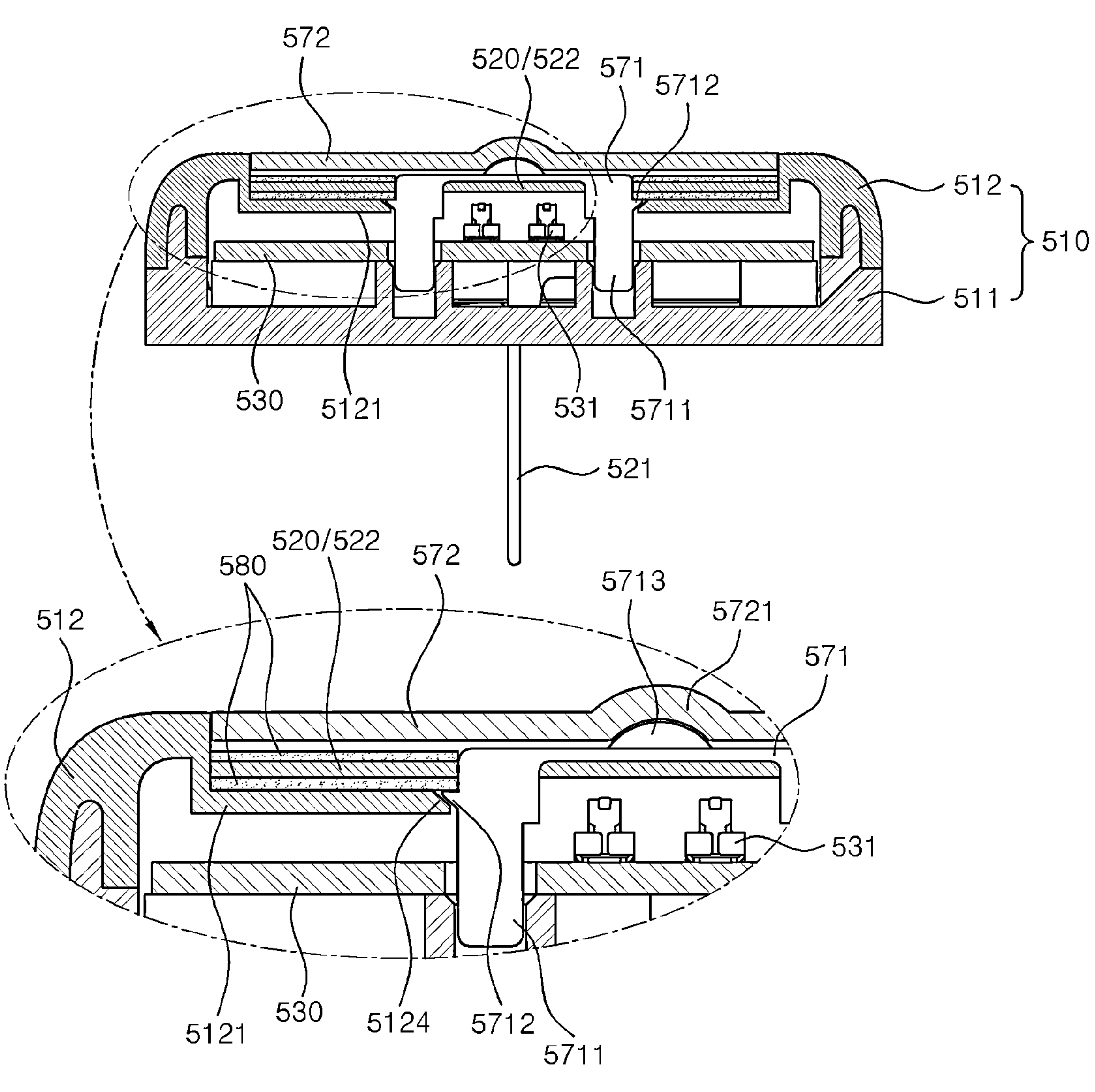
FIGS. 40 and 41 are views schematically illustrate a structure and operation status of a pressurizing operation module according to another embodiment of the present disclosure.
Figure 41:
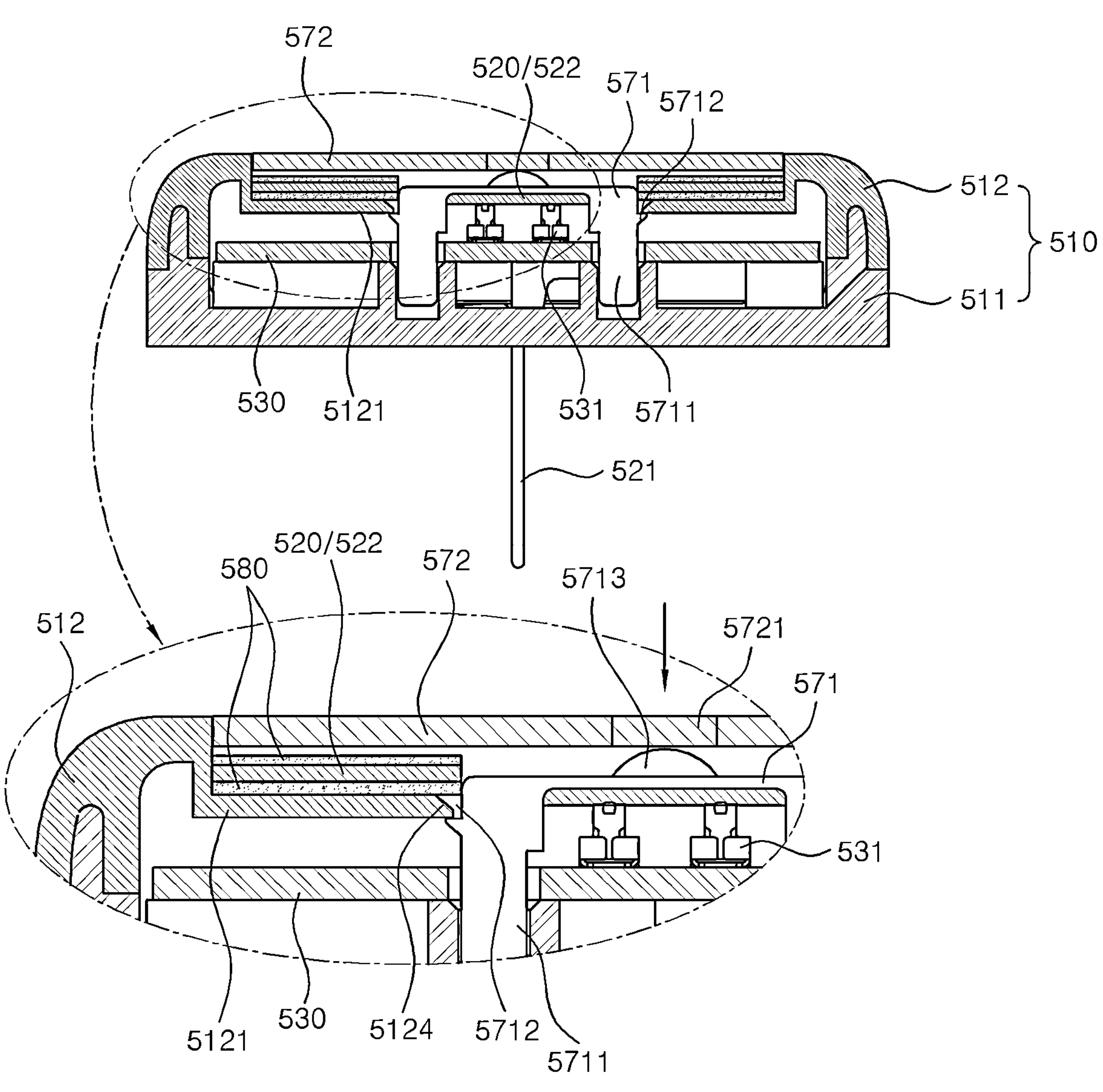

FIGS. 40 and 41 are views schematically illustrate a structure and operation status of a pressurizing operation module according to another embodiment of the present disclosure.

The pressurizing operation module (570) comprises a movable pressurizing body (571) configured to pressurize the other end portion of the sensor unit (520) by being moved by the pressure force of the user as discussed above, and a button cover (572) having soft material and covering an upper surface of the movable pressurizing body (571).

Because the button cover (572) made of soft material and having a structure of covering an upper surface of the movable pressurizing body (571) to be coupled to the housing (510), after the downward movement of the movable pressurizing body (571) according to the user's pressurizing manipulation is completed, the shape of the button cover (572) maintains a form of being freely transformable due to the character of soft material since there is no separate supporting structure. This embodiment looks unsightly and the user has difficulty in clearly identifying a state of whether the user operates to pressurize the pressurizing operation module (570) or not.

The pressurizing operation module (570) according to another embodiment of the present disclosure is configured that as the operation of the pressurizing operation module (570) is completed, a state of the pressuring operation module (570) different from a state before the operation is initiated is fixed, specially, the user can easily visually identify the state before the operation is initiated and the state after the operation is completed.

For this, as illustrated in FIG. 40, a pressurizing protruding portion (5713) upwardly protruding is formed on an upper surface of the movable pressurizing body (571), a button cover (572) is installed to be elastically transformable by being upwardly protruded by the pressurizing protruding portion (5713) in a state before the operation of the pressurizing operation module (570) is initiated. Accordingly, an elastically protruding unit (5721) configured to be elastically transformable to be upwardly protruded by the pressurizing protruding portion (5713) of the movable pressurizing body (571) is formed at the center portion of the button cover (572).

As shown in FIG. 41, as the pressurizing operation module (570) is operated to downwardly move the movable pressurizing body (571), the button cover (572) is released from a state directly contacting the pressurizing protruding portion and is return-transformed to a flat state.

According to this structure, in a state that the movable pressurizing body (571) is downwardly moved according to the operation of the pressurizing operation module (570), the upper surface of the button cover (572) becomes flat and the state of the button cover (572) is fixed by being elastically supported by its own elastic force. Additionally, before the pressurizing operation module (570) is operated, the elastically protruding unit (5721) is configured to protrude at the center portion of the button cover (572), but after the pressurizing operation module (570) is operated, the elastically protruding unit (5721) is configured to be return-transformed and become flat, and therefore the protrusion state and the release state released from the protrusion of the elastically protruding unit (5721) appear before and after the operation of the pressurizing operation module (570), respectively, and due to this the before operation state and the after operation state can be easily identified.

Figure 42:
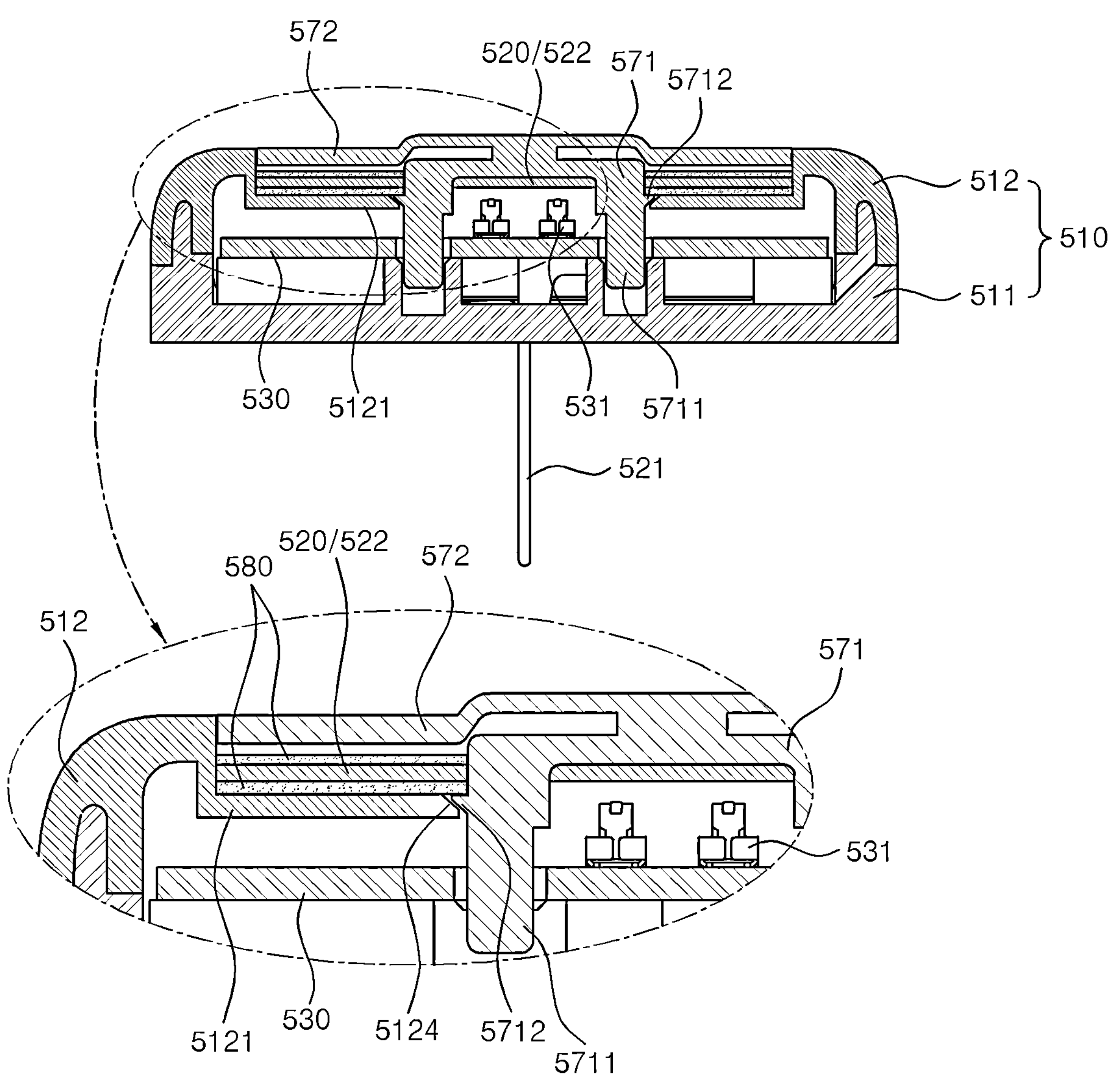
FIG. 42 is a view schematically illustrate a structure of a pressurizing operation module according to still another embodiment of the present disclosure.

FIG. 42 is a view schematically illustrate a structure of a pressurizing operation module according to still another embodiment of the present disclosure.

As shown in FIG. 42, the movable pressurizing body (571) and the button cover (572) of the pressurizing operation module (570) are formed to be integrated into one single body.

If the movable pressurizing body (571) is downwardly moved by the operation of the pressuring operation module as discussed above as the movable pressurizing body (571) with rigid material and the button cover (572) with soft material are independently formed, the button cover (572) may be freely transformable and there may be difficulty in manufacturing and increasing the cost because of their separate manufacturing processes.

To solve those issues, the movable pressurizing body (571) and the button cover (572) of the pressurizing operation module (570) may be formed to be integrated into one single body. In this embodiment, the pressurizing operation module (570) may be made of soft or flexible material like the button cover (572) to improve maneuverability, and the movable pressurizing body (571) may be formed to be thicker to have more stiffness relatively.

In this embodiment, the movable pressurizing body (571) and the button cover (572) of the pressurizing operation module (570) can be manufactured as one single piece by one single process, and it can improve maneuverability due to the character of the soft or flexible material and prevent the damages to the sensor unit (520) and other components caused by interference or wear.

Figure 43:
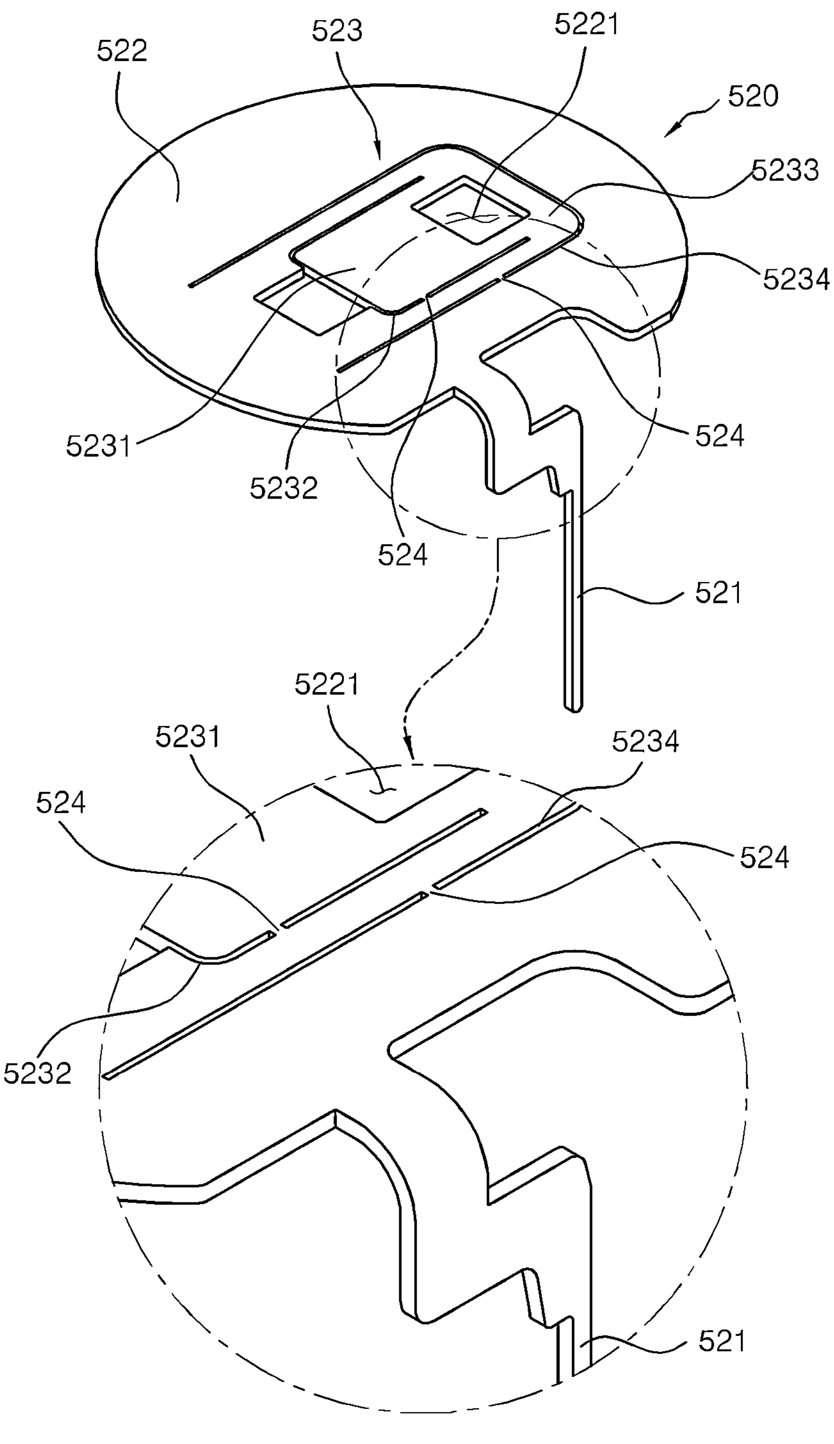
FIG. 43 is a perspective view of schematically illustrating detailed configuration of a sensor unit according to still another embodiment of the present disclosure.

FIG. 43 is a perspective view of schematically illustrating detailed configuration of a sensor unit according to still another embodiment of the present disclosure.

As discussed above, the sensor unit (520) may be configured to comprise a sensor body unit (522), wherein the pressure transforming unit (523) is formed at the center area of the sensor body unit (522) to contact a electric contact point of the PCB board, and a sensor probe unit (521) formed to be extended in a structure bent from one side of the sensor body unit (522) to be inserted into the human body.

In this embodiment, a partial area of the pressure transforming unit (523) may be formed to have a cut structure, but the sensor unit (520) according to still another embodiment of the present disclosure has a bridge unit (524) having a structure not being cut at a partial area on the cut line of the pressure transforming unit (523).

Specifically, as described above, the pressure transforming unit (523) comprise the first cut area (5231) having a structure cut along the first cut line (5232) and the second cut area (5233) having a structure cut along the second cut line (5234), but the bridge unit (524) may be formed at a plurality of points of partial sections of the first cut line (5232) and the second cut line (5234).

By having the bridge unit (524) having a structure not being cut at some sections of the pressure transforming unit (523), the cut section of the pressure transforming unit (523) may be prevented from being transformed by self-weight or mishandling fault during the assembling or manufacturing process.

Accordingly, if a portion of the pressure transforming unit (523) is formed as a cut section, the pressure transforming unit (523) may be easily transformed due to mistake such as mishandling fault of a manufacturer, but if the pressure transforming unit (523) is transformed regardless of the operation of the user, there may be a problem that the pressure transforming unit (523) can contact the electric contact point without the operation of the user. However, another embodiment of the present disclosure has the bridge unit (524) at some portions of the cut section of the pressure transforming unit (523) to support the pressure transforming unit (523) and prevent the pressure transforming unit (523) from being easily transformed, and therefore can maintain more precise and stable operation performance.

Figure 44:
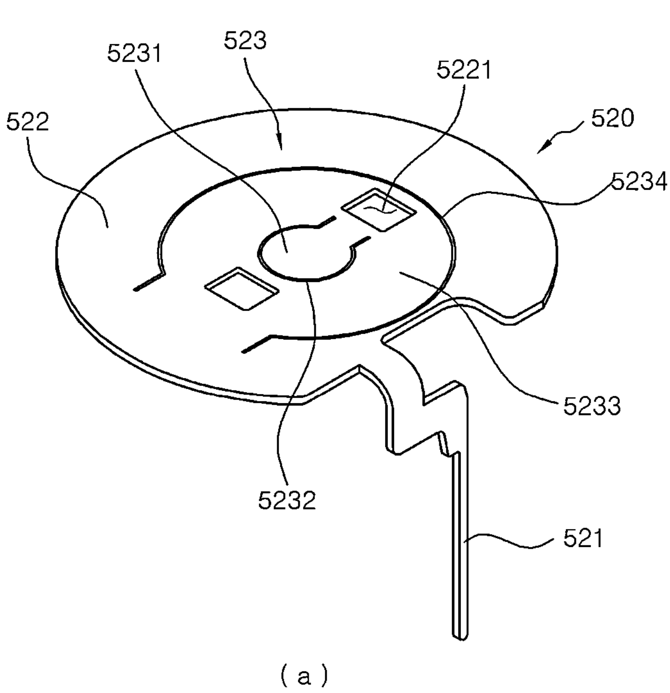
FIG. 44 is a perspective view of a structure of a pressure transforming unit of a sensor unit according to an embodiment of the present disclosure.
Figure 44:
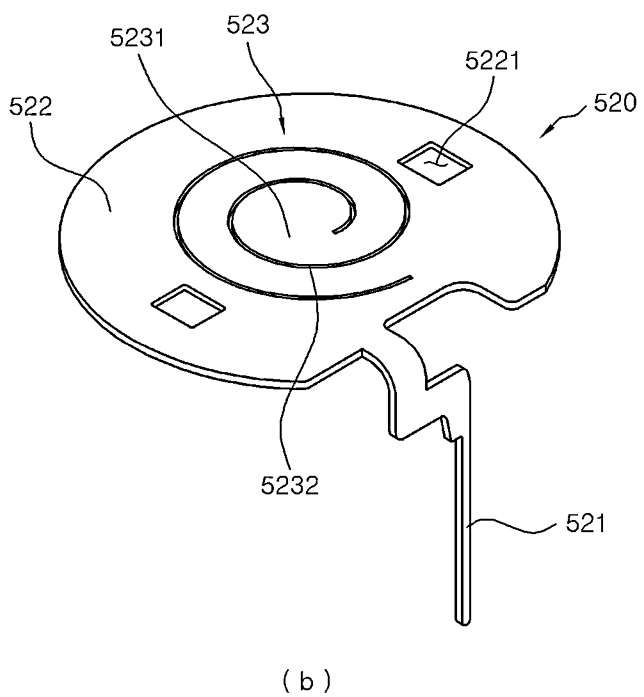

FIG. 44 is a perspective view of a structure of a pressure transforming unit of a sensor unit according to an embodiment of the present disclosure.

As described above, the pressure transforming unit (523) is formed at the sensor body unit (520) of the sensor unit (520) to have a cut structure along a cut line.

In this embodiment, the pressure transforming unit (523) is configured to comprise a first cut section (5231) having a structure cut along a first cut line (5232), and a second cut section (5233) having a structure cut along a second cut line (5234) formed at the outer section of the first cut line (5232).

These structures are examples only, and the cut lines can be variously changed. For example, as illustrated in the FIG. 44(*a*), the first cut line (5232) and the second cut line (5234) may be formed to have a curved structure.

Additionally, as shown in FIG. 44(*b*), the first cut line (5232) may be formed to have a spiral structure, in this embodiment, the movable pressurizing body (571) of the pressurizing operation module (570) may pressurize the center area along the first cut line (5232) with the spiral structure, if pressurized by the movable pressurizing body (571), the first cut section (5231) is transformed along the first cut line (5232) having the spiral structure from the center area to the outer area sequentially, and therefore it can be stably contacted to the electric contact point of the PCB board without a second cut line or a second cut section.

Figure 45:
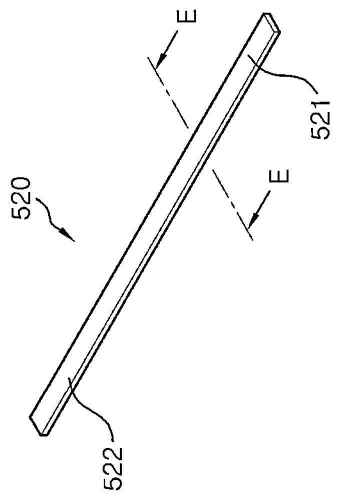
FIG. 45 is a view of showing various alternative examples of a sensor unit according to embodiments of the present disclosure.
Figure 45:
Figure 45:
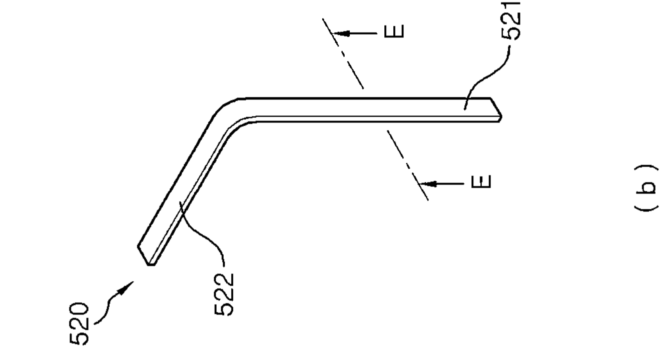
Figure 45:
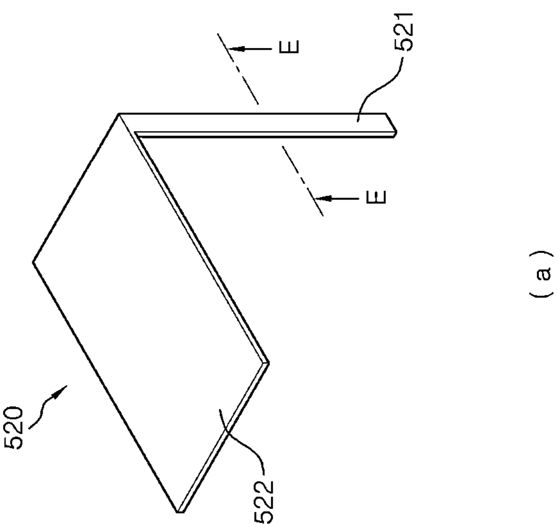
Figure 46:
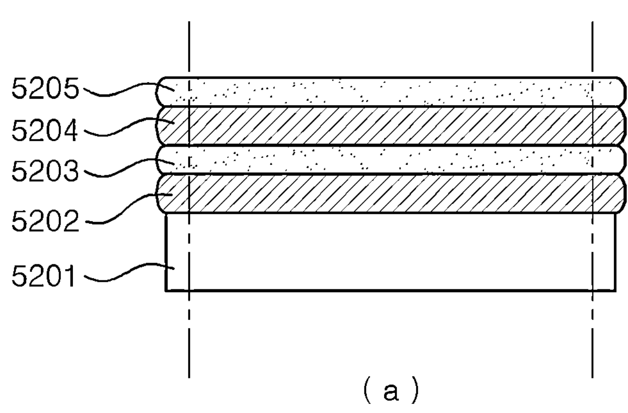
FIG. 46 is a cross-section view taken along line "E-E" of FIG. 45 for illustrating an electrode layer-built structure of a sensor unit according to an embodiment of the present disclosure.
Figure 46:
Figure 46:
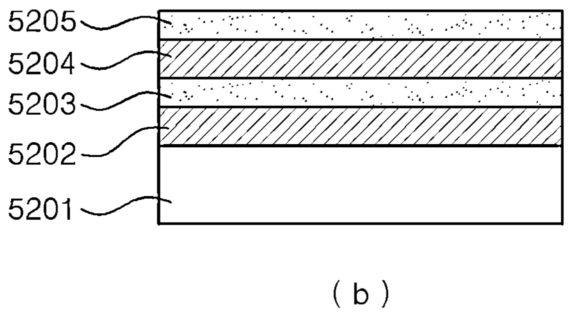
Figure 47:
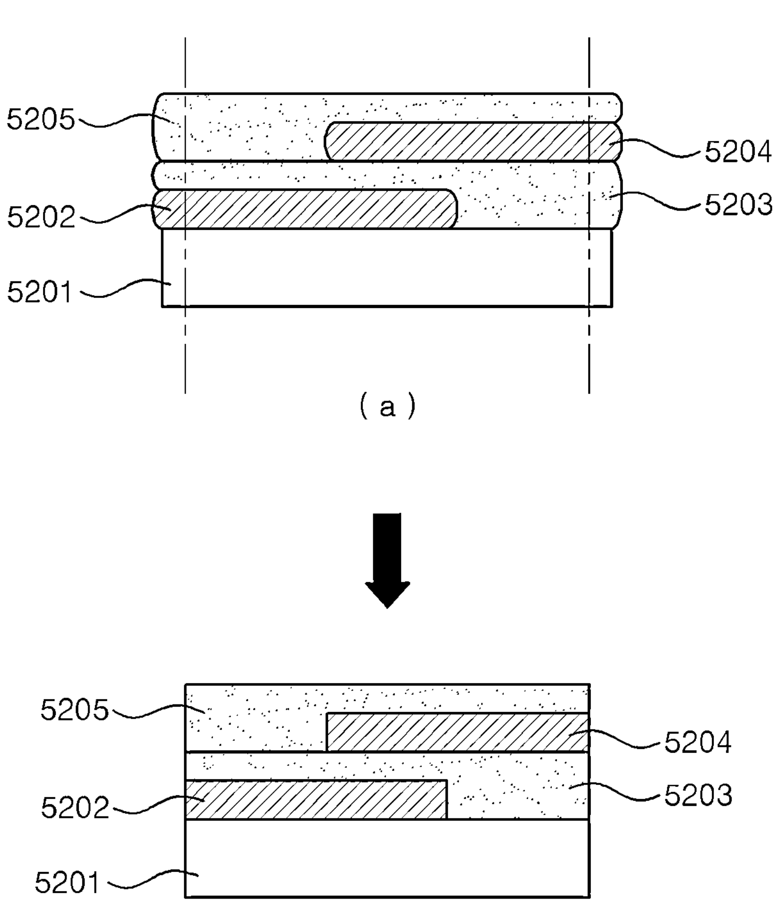
FIGS. 47 and 48 are cross-section views taken along line "E-E" of FIG. 45 for illustrating electrode layer-built structures of a sensor unit according to other embodiments of the present disclosure.
Figure 48:
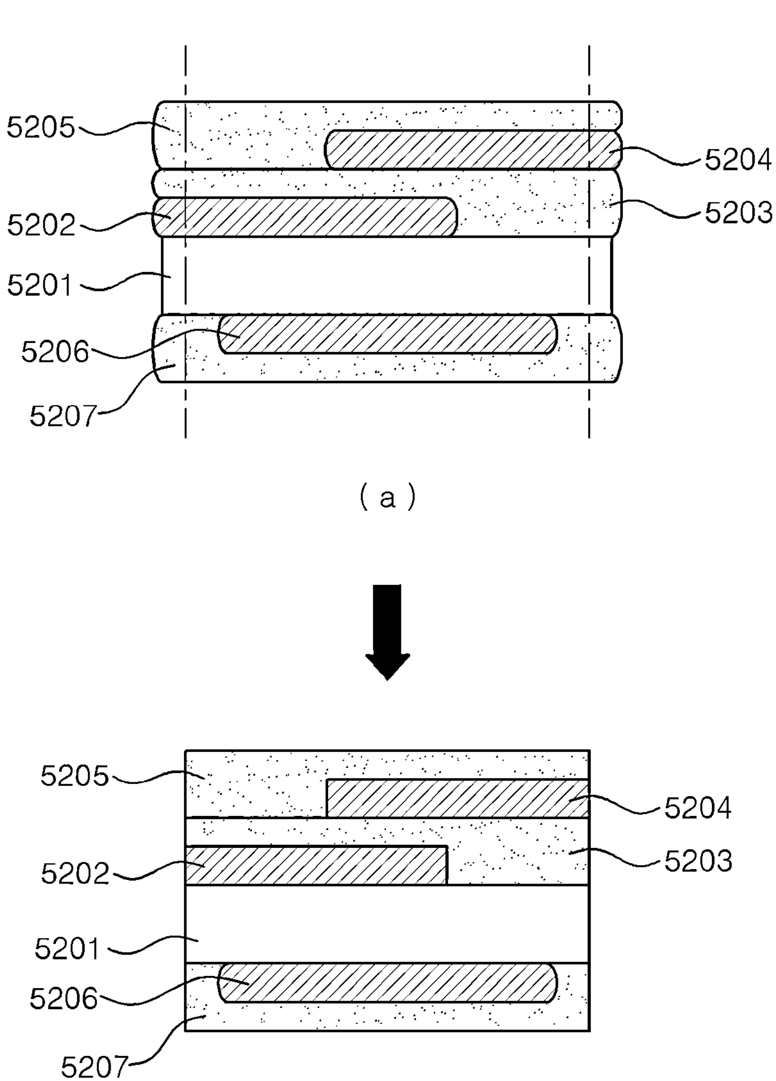

FIG. 45 is a view of showing various alternative examples of a sensor unit according to embodiments of the present disclosure, FIG. 46 is a cross-section view taken along line "E-E" of FIG. 45 for illustrating an electrode layer-built structure of a sensor unit according to an embodiment of the present disclosure, and FIGS. 47 and 48 are cross-section views taken along line "E-E" of FIG. 45 for illustrating electrode layer-built structures of a sensor unit according to other embodiments of the present disclosure.

On end portion of the sensor unit (520) is formed to extend in one direction to be inserted into the human body, and the other end portion of the sensor unit (520) is formed to be contactable with the electric contact point of the PCB board.

The sensor body unit (522) is formed so that the other end portion of the sensor unit (520) can contact the electric contact point, and the sensor probe unit (521) is formed to extend from one side of the sensor body unit (520) so that the one end portion of the sensor unit (520) can be inserted into the human body.

The structure of the sensor unit (520) may be implemented in various different ways, as shown in FIG. 45(*a*), the sensor body (522) is formed in a flat plate shape having a relatively large area, and as illustrated in FIGS. 45(*b*) and (*c*), the sensor body (522) is formed in a long and thin structure and may has a bent structure or unbent structure at a middle of the sensor body (522). However, the present disclosure is not limited thereto, and the sensor unit (520) may be formed to have various shapes.

The sensor probe unit (521) of the sensor unit (520) is formed to have multiple electrode layers so that the sensor probe unit (521) of the sensor unit (520) is inserted into the human body and information on various material from the body fluid can be measured.

Specifically, as illustrated in FIG. 46, the sensor unit (520) may be configured to comprise a substrate (5201) of which one end portion extends in one direction to be inserted into the human body, a first electrode layer (5202) formed to be stacked on an upper surface of the one end portion of the substrate (5201), a first insulation layer (5203) formed to be stacked to cover an upper surface of the first electrode layer (5202), a second electrode layer (5204) formed to be stacked on an upper surface of the first insulation layer (5203), and a second insulation layer (5205) formed to be stacked to cover an upper surface of the second electrode layer (5204).

According to the layering processes of the electrode layers, as illustrated in FIG. 46(*a*), the first electrode layer (5202), the first insulation layer (5203), the second electrode layer (5204) and the second insulation layer (5205) are stacked in order on the upper surface of the substrate (5201). Those electrode layers and insulation layers are formed fully or partially along the longitudinal direction of the sensor probe unit (521), and formed fully along the width direction of the senor probe unit perpendicular to the longitudinal direction. In the states that the electrode layers and insulation layers are stacked, both longitudinal direction side surfaces are finished by being cut along the cut lines illustrated with the dotted lines in FIG. 46(*a*). By this cutting process, both longitudinal direction side surfaces of the sensor probe unit (521) can be formed to have a smooth side surface as shown in FIG. 46(*b*).

However, in the actual manufacturing process, there is a problem in that the first electrode layer (5202) and the second electrode layer (5204) may contact each other and be electrically connected with each other due to being flowed out by a cutting blade during the process of cutting both longitudinal direction side surfaces. Specifically, because the electrode layers and the insulation layers are formed with minute thickness of micro unit, those problems can be occurred. The first electrode layer (5202) and the second electrode layer (5204) must be completely separated by the first insulation layer (5203) disposed therebetween for performing normal sensor function, but if the first electrode layer (5202) and the second electrode layer (5204) are contacted with each other during the side surface cutting process, it will be classified as a defective product because the sensor function cannot be properly performed.

To prevent this problem, an embodiment of the present disclosure may have a layered structure as illustrated in FIG. 47. Accordingly, one of the first electrode layer (5202) and the second electrode layer (5204) is exposed at one side surface of both longitudinal direction side surfaces of the sensor probe unit (521) and the other of the first electrode layer (5202) and the second electrode layer (5204) is exposed at the other side surface of both longitudinal direction side surfaces of the sensor probe unit (521) so that the first electrode layer (5202) and the second electrode layer (5204) are disposed to be exposed in opposite directions to each other.

In an example of the layering process, as illustrated in FIG. 47(*a*), the first electrode layer (5202) is stacked on the upper surface of the substrate (5201) to be sided toward the left side in the longitudinal direction, the first insulation layer (5203) is stacked on the substrate (5201) and the first electrode layer (5202) to cover the upper and side surfaces of the first electrode layer (5202). The second electrode layer (5204) is stacked on the upper surface of the first insulation layer (5203) to be sided toward the right side of the substrate (5201) in the longitudinal direction. The second insulation layer (5205) is stacked on the first insulation layer (5203) and the second electrode layer (5204) to cover the upper and side surfaces of the second electrode layer (5204).

In the states that the electrode layers and insulation layers are stacked, both longitudinal direction side surfaces are finished by being cut along the cut lines illustrated with the dotted lines in FIG. 47(*a*). By this cutting process, both longitudinal direction side surfaces of the sensor probe unit (521) may have one side surface to which the first electrode layer (5202) is exposed and the outer side surface to which the second electrode layer (5204) is exposed.

In this embodiment, unlike the layered structure illustrated in FIG. 46, the layered structure shown in FIG. 47 is stacked to be disposed in opposite directions to each other, and therefore even if the first electrode layer (5202) and the second electrode layer (5204) are flowed out by the cutting blade, the first electrode layer (5202) and the second electrode layer (5204) will not contact each other and the rate of defective products may be significantly decreased.

Meanwhile, as illustrated in FIG. 48, a third electrode layer (5206) may be formed on a lower surface of one end portion of the substrate (5201) as a separate layer, and a third insulation layer (5207) may be formed to be stacked at the substrate (5201) and the third electrode layer (5206) to cover a lower surface of the third electrode layer (5206). Unlike the first and second electrode layers (5202, 5204), the third electrode layer (5206) is formed to be stacked on the lower surface of the substrate (5201), therefore during the process of cutting both side surfaces the case of contacting the first and second electrode layers (5202, 5204) with the third electrode layer (5206) may not be occurred, and accordingly the third electrode layer (5206) may be formed on a entire lower surface of the substrate (5201) in the longitudinal direction or on only a center portion of the lower surface of the substrate (5201) as illustrated in FIG. 48.

If two electrode layers are stacked sequentially on the lower surface of the substrate (5201), they can be stacked in opposite directions to each other like the first electrode layer (5202) and the second electrode layer (5204).

If two electrode layers are stacked at the sensor unit, one of two electrode layers is configured as an operation electrode and the other of two electrode layers is configured as a counter electrode, and if three electrode layers are stacked at the sensor unit, three electrode layers are configured as an operation electrode, a counter electrode, and a reference electrode, respectively. Additionally, more than three electrode layers may be formed, and each electrode layers may be used for measuring different material.

Additionally, the first electrode layer (5202) and the second electrode layer (5204) are formed at an entire longitudinal direction area of the sensor probe unit (521) of the sensor unit, and are formed to extend to the sensor body unit (522) to contact the electrical contact points of the PCB board.

The foregoing descriptions have been presented in order to explain certain principles of the present disclosure by way of example, and a person having ordinary skill in the art which the present disclosure relates could make various modifications and variations without departing from the essential features of the present disclosure. Accordingly, the foregoing embodiments disclosed in the present disclosure shall be interpreted as being illustrative, while not being limitative, of the principle and scope of the present disclosure. It should be understood that the scope of the present disclosure shall be defined by the Claims and all of their equivalents fall within the scope of the present disclosure.

What is claimed is:

1. A continuous blood glucose measurement apparatus, comprising:

a body attachable unit configured to measure blood glucose;

an applicator comprising a main case and a plunger body disposed inside the main case, and configured to move the plunger body from a first location to a second location to attach the body attachable unit to a human body; and an adhesive layer attached to a lower surface of the body attachable unit to attach the lower surface of the body attachable unit to the human body, wherein the body attachable unit is coupled to one end of the plunger body in a state that the plunger body is in the first location, wherein the adhesive layer attached to the lower surface of the body attachable unit is spaced apart from the human body in a state that the plunger body is in the first location, wherein the body attachable unit and the adhesive layer are configured to be downwardly moved together with the plunger body to be attached to the human body as the plunger body is moved from the first location to the second location, wherein the main case comprises a return prevention unit configured to, after the plunger body is moved to the second location, block returning movement of the plunger body moving to return to the first location, wherein the return prevention unit comprises:

an interlocking body formed at one side of the plunger body; and a return prevention hook formed at the main case to prevent the returning movement of the plunger body by being engaged with an upper portion of the interlocking body when movement of the plunger body from the first location to the second location is completed.

2. The continuous blood glucose measurement apparatus of claim 1, wherein a press button is mounted to one side of the main case, wherein the plunger body is configured to be engagedly fixed at the first location inside the main case, and move to the second location by being released from fixation at the first location according to manipulation of the press button, and wherein the applicator further comprises a plunger elastic spring configured to apply an elastic force to the plunger body so that the plunger body moves from the first location to the second location.

3. The continuous blood glucose measurement apparatus of claim 1, wherein the return prevention hook is engaged by an elastic restoration force in a process of being engaged with the interlocking body.

4. The continuous blood glucose measurement apparatus of claim 1, wherein:

the main case comprises an outer case, wherein the press button is mounted to one side of the outer case, and an inner case coupled to an inside of the outer case and configured to guide a movement path of the plunger body, and the return prevention hook is formed at the inner case.

5. The continuous blood glucose measurement apparatus of claim 1, wherein an end of the plunger body is further protruded than an end of the main case in a state that the plunger body is moved from the first location to the second location.

6. The continuous blood glucose measurement apparatus of claim 1, wherein an end of the body attachable unit is further protruded than an end of the main case in a state that the body attachable unit is moved to the second location together with the plunger body.

7. The continuous blood glucose measurement apparatus of claim 1, wherein:

a protection cap is separably coupled to the applicator to block exposure of the body attachable unit from an outside of the applicator in a state that the body attachable unit is inserted into an inside of the applicator, and a release paper is attached to a lower surface of the adhesive layer which is configured to be contacted with the human body so that the body attachable unit is configured to be attached to the human body, and the release paper is configured to be separated and removed from the lower surface of the adhesive layer together with the protection cap in a process of separating the protection cap from the applicator.

8. The continuous blood glucose measurement apparatus of claim 1, wherein:

the applicator and the body attachable unit are manufactured to be assembled as one unit product in a state that the body attachable unit is inserted to an inside of the applicator, and the body attachable unit comprises a sensor unit, wherein one end portion of the sensor unit is insertable into the body, and a wireless communication chip configured to wireless communicate with an external terminal.

9. The continuous blood glucose measurement apparatus of claim 2, wherein:

a shooting plate configured to be movable according to press manipulation of the press button is coupled in the main case, and the plunger body is configured to be engagedly fixed by being engaged with the shooting plate at the first location and be released from engagement with the shooting plate according to movement of the shooting plate.

* * * * *